United States Patent
Klintz et al.

(10) Patent No.: US 6,239,074 B1
(45) Date of Patent: May 29, 2001

(54) SUBSTITUTED 3-PHENYLURACILS

(75) Inventors: Ralf Klintz, Dannstadt-Schauernheim; Peter Schaefer, Bad Duerkheim; Gerhard Hamprecht, Weinheim; Elisabeth Heistracher, Ludwigshafen; Hans-Josef Wolf, Maxdorf; Karl-Otto Westphalen, Speyer; Matthias Gerber, Mutterstadt; Uwe Kardorff, Mannheim; Helmut Walter, Obrigheim; Klaus Grossmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/774,722
(22) PCT Filed: Sep. 10, 1992
(86) PCT No.: PCT/EP92/02088
§ 371 Date: Mar. 18, 1994
§ 102(e) Date: Mar. 18, 1994
(87) PCT Pub. No.: WO93/06090
PCT Pub. Date: Apr. 1, 1993

Related U.S. Application Data

(63) Continuation of application No. 08/211,067, filed on Mar. 18, 1994, now abandoned.

(30) Foreign Application Priority Data

Sep. 20, 1991 (DE) ................................. 41 31 038

(51) Int. Cl.$^7$ ..................... A01N 43/54; C07D 239/54; C07D 239/545
(52) U.S. Cl. ................. 504/168; 504/243; 544/311; 544/312; 544/313; 544/314
(58) Field of Search .................. 504/243, 168; 544/311, 312, 313, 314

(56) References Cited

U.S. PATENT DOCUMENTS

| | | | |
|---|---|---|---|
| 4,927,451 | * 5/1990 | Brouwer et al. | 544/309 |
| 4,941,909 | * 7/1990 | Wenger et al. | 544/309 |
| 4,979,982 | * 12/1990 | Brouwer et al. | 544/309 |
| 5,041,156 | * 8/1991 | Suchy et al. | 544/309 |
| 5,066,657 | * 11/1991 | Hayashi et al. | . |
| 5,127,935 | * 7/1992 | Satow et al. | 544/309 |
| 5,154,755 | * 10/1992 | Satow et al. | 544/310 |
| 5,169,430 | * 12/1992 | Strunk et al. | 544/310 |
| 5,183,492 | * 2/1993 | Suchy et al. | 544/309 |

FOREIGN PATENT DOCUMENTS

| | | | |
|---|---|---|---|
| 397052 | * 11/1990 | (EP) | . |
| 408382 | * 1/1991 | (EP) | . |
| 9111442 | * 8/1991 | (WO) | . |

OTHER PUBLICATIONS

March, Advanced Org. Chem. 3rd Edition, (1985) p. 815.*

* cited by examiner

Primary Examiner—Patricia L. Morris
(74) Attorney, Agent, or Firm—Keil & Weinkauf

(57) ABSTRACT

A substituted 3-phenyluracil of the formula I

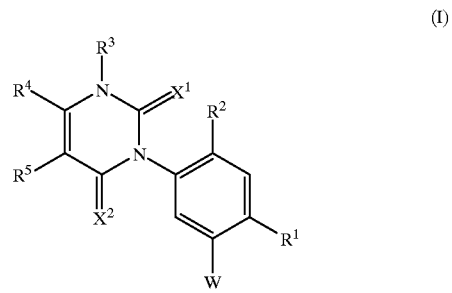

(I)

where $X^1$ and $X^2$ are each oxygen;

W is —$C(R^8)=X^5$, where $X^5$ is oxygen, sulfur, or a radical —$NR^{14}$;

$R^{14}$ is hydroxyl, alkoxy, alkenyloxy, alkynyloxy, cycloalkoxy, cycloalkenyloxy, haloalkoxy, haloalkenyloxy, hydroxyalkoxy, cyanoalkoxy, cycloalkylalkoxy, alkoxyalkoxy, alkoxyalkenyloxy, alkylcarbonyloxy, haloalkylcarbonyloxy, alkylcarbamoyloxy, haloalkylcarbamoyloxy, alkoxycarbonylalkoxy, alkylthioalkoxy, dialkylaminoalkoxy, $R^8$ is hydrogen, cyano or alkyl;

$R^1$ is halogen or cyano;

$R^2$ is hydrogen or halogen;

$R^3$ is hydrogen or alkyl;

$R^4$ is cyano, alkyl or haloalkyl;

$R^5$ is hydrogen, halogen or alkyl;

or a salt or enol ether of a compound I wherein $R^3$ is hydrogen, or its tautomeric forms, for the desiccation and defoliation of plants or as an insecticide or herbicide.

27 Claims, No Drawings

SUBSTITUTED 3-PHENYLURACILS

This application is a continuation of application Ser. No. 08/211,067, filed on Mar. 18, 1994, now abandoned, which is a 371 of PCT/EP92/02028 filed Sep. 10, 1992.

The present invention relates to novel substituted 3-phenyluracils of the general formula I

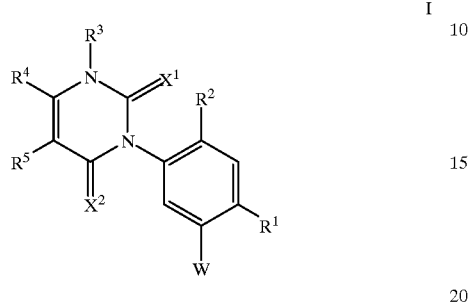

where
X$^1$ and X$^2$ are each oxygen or sulfur;
W is —C(R$^8$)=X$^5$, —C(R$^8$)(X$^3$R$^6$)(X$^4$R$^7$), —C(R$^8$)=C(R$^9$)—CN, —C(R$^8$)—C(R$^9$)—CO—R$^{10}$, —CH(R$^8$)—CH(R$^9$)—CO—R$^{10}$, —C(R$^8$)=C(R$^9$)—CH$_2$—CO—R$^{10}$, —C(R$^8$)=C(R$^9$)—C(R$^{11}$)=C(R$^{12}$)—CO—R$^{10}$ or —C(R$^8$)=C(R$^9$)—CH$_2$—CH (R$^{13}$)—CO—R$^{10}$
where
X$^3$ and X$^4$ are each oxygen or sulfur;
X$^5$ is oxygen, sulfur or a radical —NR$^{14}$;
R$^{14}$ is hydrogen, hydroxyl, C$_1$–C$_6$-alkyl, C$_3$–C$_6$-alkenyl, C$_3$–C$_6$-alkynyl, C$_3$–C$_7$-cycloalkyl, C$_1$–C$_6$-haloalkyl, C$_1$–C$_6$-alkoxy-C$_1$–C$_6$-alkyl, C$_1$–C$_6$-alkoxy, C$_3$–C$_6$-alkenyloxy, C$_3$–C$_6$-alkynyloxy, C$_5$–C$_7$-cycloalkoxy, C$_5$–C$_7$-cyclo-alkenyloxy, C$_1$–C$_6$-haloalkoxy, C$_3$–C$_6$-haloalkenyloxy, hydroxy-C$_1$–C$_6$-alkoxy, cyano-C$_1$–C$_6$-alkoxy, C$_3$–C$_7$-cycloalkyl-C$_1$–C$_6$-alkoxy, C$_1$–C$_6$-alkoxy-C$_1$–C$_6$-alkoxy, C$_1$–C$_6$-alkoxy-C$_3$–C$_6$-alkenyloxy, C$_1$–C$_6$-alkylcarbonyloxy, C$_1$–C$_6$-haloalkylcarbonyloxy, C$_1$–C$_6$-alkylcarbamoyloxy, C$_1$–C$_6$-haloalkylcarbamoyloxy-C$_1$–C$_6$-alkoxycarbonyl-C$_2$–C$_6$-alkoxy, C$_1$–C$_6$-alkylthio-C$_1$–C$_6$-alkoxy, di-C$_1$–C$_6$-alkyl-amino-C$_1$–C$_6$-alkoxy, phenyl which may carry from one to three of the following substituents: cyano, nitro, halogen, C$_1$–C$_6$-alkyl, C$_2$–C$_6$-alkenyl, C$_1$–C$_6$-haloalkyl, C$_1$–C$_6$-alkoxy and C$_1$–C$_6$-alkoxycarbonyl, phenyl-C$_1$–C$_6$-alkoxy, phenyl-C$_3$–C$_6$-alkenyloxy or phenyl-C$_3$–C$_6$-alkynyloxy, where one or two methylene groups of each of the carbon chains may be replaced with —O—, —S— or —N(C$_1$–C$_6$-alkyl)- and each phenyl ring may carry from one to three of the following substituents: cyano, nitro, halogen, C$_1$–C$_6$-alkyl, C$_2$–C$_6$-alkenyl, C$_1$–C$_6$-haloalkyl, C$_1$–C$_6$-alkoxy and C$_1$–C$_6$-alkoxycarbonyl, heterocyclyl, heterocyclyl-C$_3$–C6-alkoxy, heterocyclyl-C$_3$–C$_6$-alkenyloxy or heterocyclyl-C$_1$–C$_6$-alkynyloxy, where one or two methylene groups of each of the carbon chains may be replaced with —O—, —S— or —N(C$_1$–C$_6$-alkyl)- and the heterocyclyl ring may be from three-membered to seven-membered and saturated, unsaturated or aromatic and may contain from one to four hetero atoms selected from the group consisting of one or two oxygen or sulfur atoms and up to four nitrogen atoms and furthermore may carry from one to three of the following substituents: cyano, nitro, halogen, C$_1$–C$_6$-alkyl, C$_2$–C$_6$-alkenyl, C$_1$–C$_6$-haloalkyl, C$_1$–C$_6$-alkoxy or C$_1$–C$_6$-alkoxycarbonyl, or —N(R$^{15}$)R$^{16}$, where R$^{15}$ and R$^{16}$ are each hydrogen, C$_1$–C$_6$-alkyl, C$_3$–C$_6$-alkenyl, C$_3$–C$_6$-alkynyl, C$_3$–C$_6$-cycloalkyl, C$_1$–C$_6$-halo-alkyl, C$_1$–C$_6$-alkoxy-C$_1$–C$_6$-alkyl, C$_1$–C$_6$-alkylcarbonyl, C$_1$–C$_6$-alkoxycarbonyl, C$_1$–C$_6$-alkoxycarbonyl-C$_1$–C$_6$-alkyl or C$_1$–C$_6$-alkoxycarbonyl-C$_2$–C$_6$-alkenyl, where the alkenyl chain may additionally carry from one to three of the following radicals: halogen and cyano or phenyl which may carry from one to three of the following substituents: cyano, nitro, halogen, C$_1$–C$_6$-alkyl, C$_1$–C$_6$-haloalkyl, C$_3$–C$_6$,-alkenyl, C$_1$–C$_6$-alkoxy and C$_1$–C$_6$-alkoxycarbonyl, or R$^{15}$ and R$^{16}$ together with the common nitrogen atom form a saturated or unsaturated 4-membered to 7-membered heterocyclic structure, where one ring member may be replaced with —O—, —S—, —N—, —NH— or —N (C$_1$–C$_6$-alkyl)—;

R$^6$ and R$^7$ are each C$_1$–C$_6$-alkyl, C$_1$–C$_6$-haloalkyl, C$_3$–C$_6$-alkenyl, C$_3$–C$_6$-alkynyl or C$_1$–C$_6$-alkoxy-C$_1$–C$_6$-alkyl, or R$^6$ and R$^7$ together form a saturated or unsaturated, two-membered to four-membered carbon chain which may carry an oxo substituent, where one member of this chain may be replaced with an oxygen, sulfur or nitrogen atom which is not adjacent to X$^3$ and X$^4$, and where the chain may carry from one to three of the following radicals: cyano, nitro, amino, halogen, C$_1$–C$_6$-alkyl, C$_2$–C$_6$-alkenyl, C$_1$–C$_6$-alkoxy, C$_2$–C$_6$-alkenyloxy, C$_2$–C$_6$-alkynyloxy, C$_1$–C$_6$-haloalkyl, cyano-C$_1$–C$_6$-alkyl, hydroxy-C$_1$–C$_6$-alkyl, C$_1$–C$_6$-alkoxy-C$_1$–C$_6$-alkyl, C$_3$–C$_6$-alkenyloxy-C$_1$–C$_6$-alkyl, C$_3$–C$_6$-alkynyloxy-C$_1$–C$_6$-alkyl, C$_3$–C$_7$-cycloalkyl, C$_3$–C$_7$-cycloalkoxy, carboxyl, C$_1$–C$_6$-alkoxycarbonyl, C$_1$–C$_6$-alkylcarbonyl-oxy-C$_1$–C$_6$-alkyl and phenyl which may carry from one to three of the following radicals: halogen, cyano, nitro, amino, C$_1$–C$_6$-alkyl, C$_1$–C$_6$-haloalkyl, C$_1$–C$_6$-alkoxy and C$_1$–C$_6$-alkoxycarbonyl, and where the chain may furthermore be substituted by a fused-on or spiral-bonded three-membered to seven-membered ring, and one or two carbon atoms of this ring may be replaced with oxygen, sulfur and unsubstituted or C$_1$–C$_6$-alkyl-substituted nitrogen atoms and this ring may carry one or two of the following substituents: cyano, C$_1$–C$_6$-alkyl, C$_2$–C$_6$-alkenyl, C$_1$–C$_6$-alkoxy, C$_2$–C$_6$-cyanoalkyl, C$_1$–C$_6$-haloalkyl and C$_1$–C$_6$-alkoxycarbonyl;

R$^8$ is hydrogen, cyano, C$_1$–C$_6$-alkyl, C$_2$–C$_6$-alkenyl, C$_2$–C$_6$-alkynyl, C$_1$–C$_6$-haloalkyl, C$_3$–C$_7$-cycloalkyl, C$_1$–C$_6$-alkoxy-C$_1$–C$_6$-alkyl or C$_1$–C$_6$-alkoxycarbonyl;

R$^9$ and R$^{12}$ are each hydrogen, cyano, halogen, C$_1$–C$_6$-alkyl, C$_1$–C$_6$-alkoxy, halo-C$_1$–C$_6$-alkyl, C$_1$–C$_6$-alkylcarbonyl or C$_1$–C$_6$-alkoxycarbonyl;

R$^{10}$ is hydrogen, O—R$^{17}$, S—R$^{17}$ or C$_1$–C$_6$-alkyl which may furthermore carry one or two C$_1$–C$_6$-alkoxy substituents or R$^{10}$ is C$_3$—C$_6$-alkenyl, C$_3$—C$_6$-alkynyl, C$_1$–C$_6$-haloalkyl, C$_3$–C$_7$-cycloalkyl, C$_1$–C$_6$-alkylthio-C$_2$–C$_6$-alkyl, C$_2$–C$_6$-alkylimino-oxy, —N(R$^{15}$)R$^{16}$ or phenyl which may carry from one to three of the following substituents: cyano, nitro, halogen, C$_1$–C$_6$-alkyl, $C_2$–$C_6$-alkenyl, $C_1$–$C_6$-haloalkyl, $C_1$–$C_6$-alkoxy or $C_1$–$C_6$-alkoxycarbonyl;

$R^{17}$ is hydrogen, $C_1$–$C_6$-alkyl, $C_3$–$C_6$-alkenyl, $C_3$–$C_6$-alkynyl, $C_3$–$C_7$-cycloalkyl, $C_1$–$C_6$-haloalkyl, $C_3$–$C_6$-haloalkenyl, cyano-$C_1$–$C_6$-alkyl, $C_1$–$C_6$-alkoxy-$C_1$–$C_6$-alkyl, $C_1$–$C_6$-alkylthio-$C_1$–$C_6$-alkyl, $C_1$–$C_6$-alkyl-oximino-$C_1$–$C_6$-alkyl, $C_1$–$C_6$-alkylcarbonyl, $C_1$–$C_6$-alkoxycarbonyl, $C_1$–$C_6$-alkylcarbonyl-$C_1$–$C_6$-alkyl, $C_1$–$C_6$-alkoxycarbonyl-$C_1$–$C_6$-alkyl, phenyl or phenyl-$C_1$–$C_6$-alkyl, where each of the phenyl radicals in turn may carry from one to three of the following substituents: cyano, nitro, halogen, $C_1$–$C_6$-alkyl, $C_1$–$C_6$-haloalkyl, $C_3$–$C_6$-alkenyl, $C_1$–$C_6$-alkoxy and $C_1$–$C_6$-alkoxycarbonyl;

$R^{11}$ is hydrogen, cyano, halogen, $C_1$–$C_6$-alkyl, $C_3$–$C_6$-alkenyl, $C_3$–$C_6$-alkynyl, $C_1$–$C_6$-alkoxy-$C_1$–$C_6$-alkyl, $C_2$–$C_6$-alkylcarbonyl, $C_1$–$C_6$-alkoxycarbonyl, —$NR^{18}R^{19}$, where $R^{18}$ and $R^{19}$ have the same meanings as $R^{15}$ and $R^{16}$, or phenyl which may furthermore carry from one to three of the following substituents: cyano, nitro, halogen, $C_1$–$C_6$-alkyl, $C_1$–$C_6$-haloalkyl, $C_3$–$C_6$-alkenyl, $C_1$–$C_6$-alkoxy and $C_1$–$C_6$-alkoxycarbonyl;

$R^{13}$ is hydrogen, cyano, $C_1$–$C_6$-alkyl or $C_1$–$C_6$-alkoxycarbonyl;

or $R^9$ and $R^{10}$ together form a two-membered to five-membered carbon chain in which one carbon atom may be replaced with oxygen, sulfur or unsubstituted or $C_1$–$C_6$-alkyl-substituted nitrogen;

$R^1$ is halogen, cyano, nitro or trifluoromethyl;

$R^2$ is hydrogen or halogen;

$R^3$ is hydrogen, nitro, $C_1$–$C_6$-alkyl, $C_1$–$C_6$-alkenyl, $C_3$–$C_6$-alkynyl, $C_3$–$C_8$-cycloalkyl, $C_3$–$C_8$-cycloalkylcarbonyl, cyano-$C_1$–$C_6$-alkyl, $C_1$–$C_6$-haloalkyl, $C_1$–$C_6$-alkoxy-$C_1$–$C_6$-alkyl, formyl, $C_1$–$C_6$-alkanoyl, $C_1$–$C_6$-alkoxycarbonyl, $C_1$–$C_6$-haloalkylcarbonyl, $C_1$–$C_6$-alkylcarbonyl-$C_1$–$C_6$-alkyl, $C_1$–$C_6$-alkoxycarbonyl-$C_1$–$C_6$-alkyl;

a group —$N(R^{20})R^{21}$ where $R^{20}$ and $R^{21}$ have one of the meanings of $R^{15}$ and $R^{16}$; phenyl or phenyl-$C_1$–$C_6$-alkyl, where each phenyl ring may carry from one to three of the following radicals: cyano, nitro, halogen, $C_1$–$C_6$-alkyl, $C_6$–$C_6$-alkenyl, $C_1$–$C_6$-haloalkyl, $C_1$–$C_6$-alkoxy and $C_1$–$C_6$-alkoxycarbonyl;

$R^4$ is hydrogen, cyano, nitro, halogen, $C_1$–$C_6$-alkyl, $C_2$–$C_6$-alkenyl, $C_2$–$C_6$-alkynyl, $C_3$–$C_8$-cycloalkyl, $C_1$–$C_6$-haloalkyl, $C_1$–$C_6$-hydroxyalkyl, cyano-$C_1$–$C_6$-alkyl, $C_1$–$C_6$-alkoxy, $C_1$–$C_6$-alkylthio, $C_1$–$C_6$-alkoxy-$C_1$–$C_6$-alkyl, $C_1$–$C_6$-alkylthio-$C_1$–$C_6$-alkyl or phenyl which may carry from one to three of the following radicals: cyano, nitro, halogen, $C_1$–$C_6$-alkyl, $C_2$–$C_6$-alkenyl, $C_1$–$C_6$-haloalkyl, $C_1$–$C_6$-alkoxy and $C_1$–$C_6$-alkoxycarbonyl;

$R^5$ is hydrogen, cyano, nitro, halogen, $C_1$–$C_6$-alkyl, $C_2$–$C_6$-alkenyl, $C_2$–$C_6$-alkynyl, $C_3$–$C_7$-cycloalkyl, $C_1$–$C_6$-haloalkyl, $C_1$–$C_6$-hydroxyalkyl, cyano-$C_1$–$C_6$-alkyl, $C_1$–$C_6$-alkoxy-$C_1$–$C_6$-alkyl, $C_1$–$C_6$-alkylthio-$C_1$–$C_6$-alkyl, formyl, $C_1$–$C_6$-alkyl-carbonyl, $C_1$–$C_6$-haloalkylcarbonyl, $C_1$–$C_6$-alkoxycarbonyl, $C_1$–$C_6$-alkoxycarbonyl-$C_2$–$C_6$-alkenyl, —$N(R^{22})R^{23}$, where $R^{22}$ and $R^{23}$ have one of the meanings of $R^{15}$ and $R^{16}$, or phenyl which may carry from one to three of the following: cyano, nitro, halogen, $C_1$–$C_6$-alkyl, $C_2$–$C_6$-alkenyl, $C_1$–$C_6$-haloalkyl, $C_1$–$C_6$-alkoxy and $C_1$–$C_6$-alkoxycarbonyl, or $R^4$ and $R^5$ together form a saturated or unsaturated 3-membered or 4-membered carbon chain which may contain from one to three of the following hetero atoms: 1 or 2 oxygen atoms, 1 or 2 sulfur atoms and from 1 to 3 nitrogen atoms, and the chain may furthermore carry from one to three of the following radicals: cyano, nitro, amino, halogen, $C_1$–$C_6$-alkyl, $C_2$–$C_6$-alkenyl, $C_1$–$C_6$-alkoxy, $C_1$–$C_6$-alkylthio and $C_1$–$C_6$-alkoxycarbonyl;

with the proviso that $R^4$ may not be trifluoromethyl at the same time as $R^5$ is hydrogen when W is —CH=CH—CO—$R^{10}$ where $R^{10}$ is $C_1$–$C_6$-alkoxy or $C_3$–$C_7$-cycloalkoxy, and with the proviso that $R^4$ and $R^5$ are not simultaneously hydrogen when W is CE($R^8$)—CH($R^9$)—CO—$R^{10}$ and $R^9$ is not halogen, and the salts and enol ethers of those compounds I in which $R^3$ is hydrogen.

The present invention furthermore relates to herbicidal 3-phenyluracils of the general formulae Ia and Ib

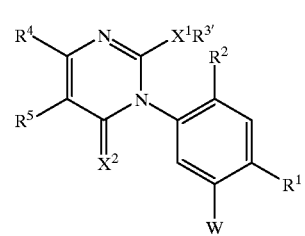

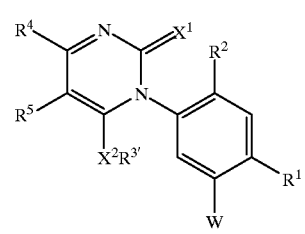

in which $R^{3'}$ is $C_1$–$C_6$-alkyl, $C_3$–$C_6$-alkenyl or $C_3$–$C_6$-alkynyl.

The present invention furthermore relates to herbicides, pesticides and plant growth-regulating agents which contain these compounds as active ingredients.

U.S. Pat. No. 4,979,982 discloses herbicidal 3-phenyluracils of the formula I'

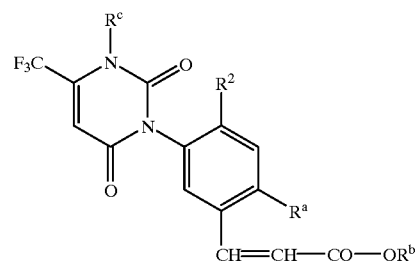

where $R^a$ is hydrogen or halogen, $R^b$ is $C_1$–$C_{12}$-alkyl or cycloalkyl and $R^c$ is $C_1$–$C_{12}$-alkyl or $C_3$–$C_{12}$-alkenyl.

Furthermore, EP-A 408 382 describes, inter alia, structures of the formula I",

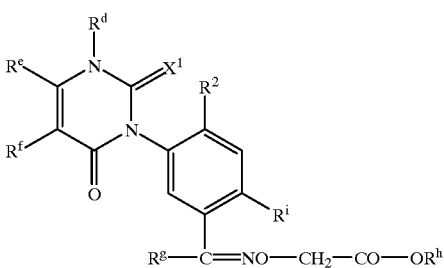

where $R^d$ is hydrogen, alkyl, hydroxymethyl or haloalkyl, $R^e$ is haloalkyl, $R^f$ is hydrogen, alkyl, haloalkyl, hydroxymethyl, halogen or nitro, $X^1$ is oxygen or sulfur, $R^g$ is hydrogen, alkyl, alkoxy or alkoxyalkyl and $R^h$ is hydrogen, alkyl, cycloalkyl, haloalkyl, phenyl or benzyl and $R^i$ is halogen, nitro or cyano.

Moreover, Swiss Patent 482,402 relates to weed killers which contain as active ingredients, inter alia, substituted uracils and thiouracils of the formula I'''

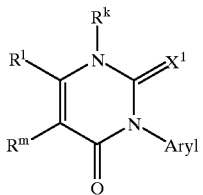

where Aryl is aryl which is unsubstituted or substituted by fluorine, chlorine, bromine, hydroxyl, alkoxy, cyano, alkylthio, alkyl or nitro, $R^k$ is dialkylphosphoryl, alkyl, alkenyl, cyano, hydrogen, unsubstituted or substitituted alkyl, unsubstituted or substituted carbamoyl, unsubstituted or substituted thiocarbamoyl, unsubstituted or substituted mercapto or acyl, $R^l$ is alkyl, alkoxy, hydrogen, chlorine or bromine and $R^m$ is alkylthio, alkoxy, alkylthioalkyl, alkenyl, cyano, thiocyano, nitro, halogen, hydrogen or unsubstituted or substituted alkyl or $R^l$ and $R^m$ together form a tri-, tetra- or penta-methylene chain.

Furthermore, WO-A 87/07 602 describes, inter alia, compounds of the formula $I^{IV}$

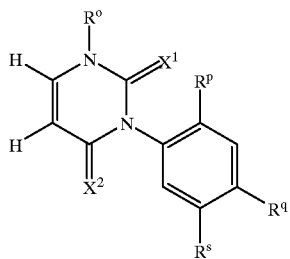

where $R^p$ and $R^q$ are each alkyl, alkenyl, alkynyl or halogen and $R^s$ is, inter alia, cyano or a substituted alkylcarbonyl-, carbonyl- or alkoxycarbonyl-alkyl group and $R^c$ is hydrogen, alkyl, alkylcarbonyl, alkenyl or alkynyl.

Other 3-aryluracils of the same type as compounds I are disclosed, for example, in the following publications: EP-A 195 346, EP-A 260 621,- EP-A 438 209, WO 88/10254, WO 89/02891 and WO 89/03825, EP-A 473 551, WO 91/00278, WO 90/15057, EP-A 255 047, EP-A 438 209, EP-A 408 382, EP-A 476 697, EP-A 420 194, U.S. Pat. No. 4,981,508, WO 91/07393, U.S. Pat. No. 3,981,715 and DE-A 37 12 782.

The selectivity of these known herbicides with respect to the weeds is, however, satisfactory only to a limited extent, so that it is an object of the present invention to provide novel herbicidal compounds with which the weeds can be selectively controlled more effectively than in the past (and which are well tolerated by the crops).

We have found that this object is achieved by the substituted 3-phenyluracils I, Ia and Ib defined at the outset.

We have also found herbicides which contain these substances and have a good herbicidal action. They are tolerated and hence selective in broad-leaved crops and in monocotyledon plants which are not members of the Gramineae.

The novel compounds I, Ia and Ib are also suitable as defoliants or desiccants in, for example, cotton, potato, rape, sunflower, soybean or field beans. Some compounds I can also be used for controlling pests, in particular insects.

The meanings stated above for $R^1$ to $R^{17}$ are general terms for an individual list of the specific group members. All alkyl, alkenyl, alkynyl, haloalkyl and haloalkoxy moieties may be straight-chain or branched. The haloalkyl and haloalkoxy radicals may carry identical or different halogen atoms.

Examples of specific meanings are as follows:

halogen: fluorine, chlorine, bromine and iodine, preferably fluorine and chlorine;

$C_1$–$C_6$-alkyl: methyl, ethyl, n-propyl, 1-methylethyl, n-butyl, 1-methylpropyl, 2-methylpropyl, 1,1-dimethyl-ethyl, n-pentyl, 1-methylbutyl, 2-methylbutyl, 3-methyl-butyl, 2,2-dimethylpropyl, 1-ethylpropyl, 1,1-dimethyl-propyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably methyl, ethyl, isopropyl, n-butyl and tert-butyl;

$C_2$–$C_6$-alkenyl: vinyl and $C_3$–$C_6$-alkenyl, such as prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methyl-prop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-l-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methyl-pent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2- dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl, preferably vinyl, prop-2-en-1-yl and but-2-en-2-yl;

$C_2$–$C_6$-alkynyl: ethynyl and $C_3$–$C_6$-alkynyl, such as prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pentyn-5-yl, pent-2-yn-1-yl, pent-2-yn-4-yl, pent-2-yn-5-yl, 3-methylbut-1-yn-1-yl, 3-methyl-but-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-ynyl;

$C_3$–$C_8$-cycloalkyl: cyclopropyl, cyclobutyl, cyclopentyl, cyclohexyl, cycloheptyl and cyclooctyl, preferably cyclopropyl, cyclopentyl and cyclohexyl;

$C_1$–$C_6$-haloalkyl: chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl;

hydroxy-$C_1$–$C_6$-alkyl: hydroxymethyl, 1-hydroxyeth-1-yl, 2-hydroxyeth-1-yl, 1-hydroxyprop-1-yl, 2-hydroxyprop-1-yl, 3-hydroxyprop-1-yl, 1-hydroxyprop-2-yl, 2-hydroxyprop-2-yl, 1-hydroxybut-1-yl, 2-hydroxybut-1-yl, 3-hydroxybut-1-yl, 4-hydroxybut-1-yl, 1-hydroxybut-2-yl, 2-hydroxybut-2-yl, 1-hydroxybut-3-yl, 2-hydroxybut-3-yl, 1-hydroxy-2-methylprop-3-yl, 2-hydroxy-2-methylprop-3-yl, 3-hydroxy-2-methylprop-3-yl and 2-hydroxymethylprop-2-yl, preferably hydroxymethyl;

cyano-$C_1$–$C_6$-alkyl: cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyano-but-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl, preferably cyanomethyl;

amino-$C_1$–$C_6$-alkyl: aminomethyl, 1-aminoethyl, 2-amino-ethyl, 1-aminoprop-1-yl, 2-aminoprop-1-yl, 3-aminoprop-1-yl, 1-aminobut-1-yl, 2-aminobut-1-yl, 3-aminobut-1-yl, 4-aminobut-1-yl, 1-aminobut-2-yl, 2-aminobut-2-yl, 3-aminobut-2-yl, 4-aminobut-2-yl, 1-(aminomethyl)-eth-1-yl, 1-(aminomethyl)-1-(methyl)-eth-1-yl and 1-(aminomethyl)-prop-1-yl, preferably aminomethyl;

phenyl-$C_1$–$C_6$-alkyl: benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 4-phenylbut-2-yl, 1-(phenylmethyl)-eth-1-yl, 1-(phenylmethyl)-1-(methyl)-eth-1-yl and 1-(phenyl-methyl)-prop-1-yl, preferably benzyl;

$C_1$–$C_6$-alkoxy: methoxy, ethoxy, n-propoxy, 1-methylethoxy, n-butoxy, 1-methylpropoxy, 2-methylpropoxy, 1,1-dimethyl-ethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, preferably $C_1$–$C_4$-alkoxy, such as methoxy and ethoxy;

$C_1$–$C_6$-haloalkoxy: 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and 3-bromoprop-1-yloxy;

$C_1$–$C_6$-alkylthio: methylthio, ethylthio, n-propylthio, 1-methylethylthio, n-butylthio, 1-methylpropylthio, 2-methylpropylthio, 1,1-dimethylethylthio, n-pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, n-hexylthio, 1-methylpentylthio, 2-methylpentylthio, 3-methylpentylthio 4-methylpentylthio, 1,1-dimethylbutylthio, 1,2-dimethyl-butylthio, 1,3-dimethylbutylthio, 2,2-dimethylbutylthio, 2,3-dimethylbutylthio, 3,3-dimethylbutylthio, 1-ethyl-butylthio, 2-ethylbutylthio, 1,1,2-trimethylpropylthio, 1,2,2-trimethylpropylthio, 1-ethyl-1-methylpropylthio and 1-ethyl-2-methylpropylthio, preferably $C_1$–$C_4$-alkylthio, such as methylthio and ethylthio;

$C_1$–$C_6$-alkoxy-$C_1$–$C_6$-alkyl: methoxymethyl, ethoxymethyl, n-propoxymethyl, (1-methylethoxy)-methyl, n-butoxymethyl, (1-methylpropoxy)-methyl, (2-methylpropoxy)-methyl, (1,1-dimethylethoxy)-methyl, methoxyethyl, ethoxyethyl, n-propoxyethyl, (1-methylethoxy)-ethyl, n-butoxyethyl, (1-methylpropoxy)-ethyl, (2-methylpropoxy)-ethyl, (1,1-dimethylethoxy)-ethyl, 3-methoxypropyl, 2-methoxypropyl and 2-ethoxypropyl, preferably $C_1$–$C_4$-alkoxy-$C_1$- or -$C_2$-alkyl, such as methoxymethyl, ethoxymethyl, 2-methoxy-ethyl and 2-ethoxyethyl;

$C_1$–$C_6$-alkylamino: methylamino, ethylamino, n-propylamino, 1-methylethylamino, n-butylamino, 1-methylpropylamino, 2-methylpropylamino, 1,1-dimethylethylamino, n-pentylamino, 1-methylbutylamino, 2-methylbutylamino, 3-methylbutyl-amino, 2,2-dimethylpropylamino, 1-ethylpropylamino, n-hexylamino, 1,1-dimethylpropylamino, 1,2-dimethylpropyl-amino, 1-methylpentylamino, 2-methylpentylamino, 3-methylpentylamino, 4-methylpentylamino, 1,1-dimethyl-amino, butylamino, 1,2-dimethylbutylamino, 1,3-dimethylbutyl-amino, 2,2-dimethylbutylamino, 2,3-dimethylbutylamino, 3,3-dimethylbutylamino, 1-ethylbutylamino, 2-ethylbutyl-amino, 1,1,2-trimethylpropylamino, 1,2,2-trimethylpropyl-amino, 1-ethyl-1-methylpropylamino and 1-ethyl-2-methyl-propylamino, preferably $C_1$–$C_4$-alkylamino, such as methyl-amino and ethylamino;

di-$C_1$–$C_6$-alkylamino: N,N-dimethylamino, N,N-diethylamino, N,N-dipropylamino, N,N-di-(1-methylethyl)-amino, N,N-dibutylamino, N,N-di-(1-methylpropyl)-amino, N,N-di-(2-methylpropyl)-amino, N,N-di-(1,1-dimethylethyl)-amino, N-ethyl-N-methylamino, N-methyl-N-propylamino, N-methyl-N-(1-methylethyl)-amino, N-butyl-N-methylamino, N-methyl-N-(1-methylpropyl)-amino, N-methyl-N-(2-methylpropyl)-amino, N-(1,1-dimethylethyl)-N-methylamino, N-ethyl-N-propylamino, N-ethyl-N-(1-methylethyl)-amino, N-butyl-N-ethylamino, N-ethyl-N-(1-methylpropyl)-amino, N-ethyl-N-(2-methylpropyl)-amino, N-ethyl-N-(1,1-dimethylethyl)-amino, N-(1-methylethyl)-N-propylamino, N-butyl-N-propyl-amino, N-(1-methylpropyl)-N-propylamino, N-(2-methyl-propyl)-N-propylamino, N-(1,1-dimethylethyl)-N-propyl-amino, N-butyl-N-(1-methylethyl)-amino, N-(1-methyl-ethyl)-N-(1-methylpropyl)-amino, N-(1-methylethyl)-N-(2-methylpropyl)-amino, N-(1,1-dimethylethyl)-N-(1-methyl-ethyl)-amino, N-butyl-N-(1-methylpropyl)-amino, N-butyl-N-(2-methylpropyl)-amino, N-butyl-N-(1,1-dimethyl-ethyl)-amino, N-(1-methylpropyl)-N-(2-methylpropyl)-amino, N-(1,1-dimethylethyl)-N-(1-methylpropyl)-amino and N-(1,1-dimethylethyl)-N-(2-methylpropyl)-amino, preferably dimethylamino and diethylamino;

$C_1$–$C_6$-alkylcarbonyl: methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutyl-carbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentyl-carbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-tri-methylpropylcarbonyl, 1,2,2-trimethylpropylcarbonyl, 1-ethyl-1-methylpropylcarbonyl and 1-ethyl-2-methylpropyl-carbonyl, preferably $C_1$–$C_4$-alkylcarbonyl, such as methyl-carbonyl and ethylcarbonyl;

$C_1$–$C_6$-alkylcarbonyloxy: methylcarbonyloxy, ethylcarbonyl-oxy, n-propylcarbonyloxy, 1-methylethylcarbonyloxy, n-butylcarbonyloxy, 1-methylpropylcarbonyloxy, 2-methyl-propylcarbonyloxy, 1,1-dimethylethylcarbonyloxy, n-pentylcarbonyloxy, 1-methylbutylcarbonyloxy, 2-methyl-butylcarbonyloxy, 3-methylbutylcarbonyloxy, 1,1-dimethyl-propylcarbonyloxy, 1,2-dimethylpropylcarbonyloxy, 2,2-dimethylpropylcarbonyloxy, 1-ethylpropylcarbonyloxy, n-hexylcarbonyloxy, 1-methylpentylcarbonyloxy, 2-methyl-pentylcarbonyloxy, 3-methylpentylcarbonyloxy, 4-methyl-pentylcarbonyloxy, 1,1-dimethylbutylcarbonyloxy, 1,2-dimethylbutylcarbonyloxy, 1,3-dimethylbutylcarbonyloxy, 2,2-dimethylbutylcarbonyloxy, 2,3-dimethylbutylcarbonyloxy, 3,3-dimethylbutylcarbonyloxy, 1-ethylbutylcarbonyloxy, 2-ethylbutylcarbonyloxy, 1,1,2-trimethylpropyl-carbonyloxy, 1,2,2-trimethylpropylcarbonyloxy, 1-ethyl-1-methylpropylcarbonyloxy and 1-ethyl-2-methylpropyl-carbonyloxy, preferably $C_1$–$C_4$-alkylcarbonyloxy, such as methylcarbonyloxy and ethylcarbonyloxy;

$C_1$–$C_6$-alkylcarbamoyloxy, such as methylcarbamoyloxy, ethylcarbamoyloxy, propylcarbamoyloxy, 1-methylethyl-carbamoyloxy, butylcarbamoyloxy, 1-methylpropylcarbamoyloxy, 2-methylpropylcarbamoyloxy, 1,1-dimethylethyl-carbamoyloxy, pentylcarbamoyloxy, 1-methylbutylcarbamoyloxy, 2-methylbutylcarbamoyloxy, 3-methylbutylcarbamoyloxy, 1,1-dimethylpropylcarbamoyloxy, 1,2-dimethylpropyl-carbamoyloxy, 2,2-dimethylpropylcarbamoyloxy, 1-ethyl-propylcarbamoyloxy, hexylcarbamoyloxy, 1-methylpentyl-carbamoyloxy, 2-methylpentylcarbamoyloxy, 3-methylpentyl-carbamoyloxy, 4-methylpentylcarbamoyloxy, 1,1-dimethyl-butylcarbamoyloxy, 1,2-dimethylbutyl-carbamoyloxy, 1,3-dimethylbutylcarbamoyloxy, 2,2-dimethylbutylcarbamoyloxy, 2,3-dimethylbutylcarbamoyloxy, 3,3-dimethylbutyl-carbamoyloxy, 1-ethylbutylcarbamoyloxy, 2-ethylbutyl-carbamoyloxy, 1,1,2-trimethylpropylcarbamoyloxy, 1,2,2-trimethylpropylcarbamoyloxy, 1-ethyl-1-methylpropyl-carbamoyloxy and 1-ethyl-2-methylpropylcarbamoyloxy, preferably $C_1$–$C_4$-alkylcarbamoyloxy, in particular methyl-carbamoyloxy and ethylcarbamoyloxy;

$C_1$–$C_6$-haloalkylcarbamoyloxy, in particular $C_1$- or $C_2$-haloalkylcarbamoyloxy, such as chloromethylcarbaimoyloxy, dichloromethylcarbamoyloxy, trichloromethylcarbamoyloxy, fluoromethylcarbamoyloxy, difluoromethylcarbamoyloxy, trifluoromethylcarbamoyloxy, chlorofluoromethylcarbamoyloxy, dichlorofluoromethylcarbamoyloxy, chlorodifluoro-methylcarbamoyloxy, 1-fluoroethylcarbamoyloxy, 2-fluoro-ethylcarbamoyloxy, 2,2-difluoroethylcarbamoyloxy, 2,2,2-trifluoroethylcarbamoyloxy, 2-chloro-2-fluoroethyl-carbamoyloxy, 2-chloro-2,2-difluoroethylcarbamoyloxy, 2,2-dichloro-2-fluoroethylcarbamoyloxy, 2,2,2-trichloroethylcarbamoyloxy and pentafluoroethylcarbamoyloxy;

$C_1$- or $C_2$-haloalkylcarbonyloxy: chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, α-fluoropropionyl, β-fluoropropionyl, β,β,-difluoropropionyl, β,β,β-trifluoropropionyl, β-chloro-β,β-fluoropropionyl, β-chloro-β,β-difluoropropionyl, β,β-dichloro-β-fluoropropionyl, β,β,β-trichloropropionyl and pentafluoropropionyl, preferably trichloroacetyl and trifluoroacetyl;

$C_1$–$C_6$-alkoxycarbonyl-$C_1$–$C_6$-alkyl: methoxycarbonylmethyl, ethoxycarbonylmethyl, n-propoxycarbonylmethyl, (1-methylethoxycarbonyl)-methyl, n-butoxycarbonylmethyl,(1-methylpropoxycarbonyl)-methyl, (2-methylpropoxycarbonyl)-methyl, (1,1-dimethylethoxycarbonyl)-methyl, methoxycarbonylethyl, ethoxycarbonylethyl, n-propoxycarbonyl-ethyl, (1-methylethoxycarbonyl)-ethyl-, n-butoxycarbonyl-ethyl, (1-methylpropoxycarbonyl)-ethyl, (2-methylpropoxy-carbonyl)-ethyl, (1,1-dimethylethoxycarbonyl)-ethyl, 3-(methoxycarbonyl)-propyl, 2-(methoxycarbonyl)-propyl and 2-(ethoxycarbonyl)-propyl, preferably $C_1$–$C_4$-alkoxy-carbonyl-$C_1$- or -$C_2$-alkyl, such as methoxycarbonylmethyl, ethoxycarbonylmethyl, 2-methoxycarbonylethyl and 2-ethoxycarbonylethyl;

di-$C_1$–$C_6$-alkylamino-$C_1$–$C_6$-alkoxy: N,N-dimethylaminoethoxy, N,N-diethylaminoethoxy, N,N-di(n-propyl)-aminoethoxy, N,N-di-(1-methylethyl)-aminoethoxy, N,N-dibutylamino-ethoxy, N,N-di-(1-methylpropyl)-aminoethoxy, N,N-di-(2-methylpropyl)-aminoethoxy, N,N-di-(1,1-dimethylethyl)-aminoethoxy, N-ethyl-N-methylaminoethoxy, N-methyl-N-propylaminoethoxy, N-methyl-N-(l-methylethyl)-aminoethoxy, N-butyl-N-methylaminoethoxy, N-methyl-N-(1-methylpropyl)-aminoethoxy, N-methyl-N-(2-methylpropyl)-aminoethoxy, N-(1,1-dimethylethyl)-N-methylaminoethoxy, N-ethyl-N-propylaminoethoxy, N-ethyl-N-(1-methylethyl)-aminoethoxy, N-butyl-N-ethylaminoethoxy, N-ethyl-N-(1-methylpropyl)-aminoethoxy, N-ethyl-N-(2-methylpropyl)-aminoethoxy, N-ethyl-N-(1,1-dimethylethyl)-aminoethoxy, N-(1-methylethyl)-N-propylaminoethoxy, N-butyl-N-propyl-aminoethoxy, N-(-methylpropyl)-N-propylaminoethoxy, N-(2-methylpropyl)-N-propylaminoethoxy, N-(1,1-dimethylethyl)-N-propylaminoethoxy, N-butyl-N-(1-methyl-ethyl)-aminoethoxy, N-(1-methylethyl)-N-(1-methylpropyl)-aminoethoxy, N-(1-methylethyl)-N-(2-methylpropyl)-amino-ethoxy, N-(1,1-dimethylethyl)-N-(1-methylethyl)-amino-ethoxy, N-butyl-N-(1-methylpropyl)-aminoethoxy, N-butyl-N-(2-methylpropyl)-aminoethoxy, N-butyl-N-(1,1-dimethyl-ethyl)-aminoethoxy, N-(1-methylpropyl)-N-(2-methyl-propyl)-aminoethoxy, N-(1,1-dimethylethyl)-N-(1-methyl-propyl)-aminoethoxy and N-(1,1-dimethylethyl)-N-(2-methylpropyl)-aminoethoxy.

The substituted phenyluracils I may be in the form of their agriculturally useful salts or enol ethers where $R^3$ is hydrogen.

Suitable agriculturally useful salts are in general the salts of bases which do not adversely affect the herbicidal action of I.

Particularly suitable basic salts are those of the alkali metals, preferably the sodium and potassium salts, those of the alkaline earth metals, preferably calcium, magnesium and barium salts, and those of the transition metals, preferably manganese, copper, zinc and iron salts, as well as the ammonium salts, which may carry from one to three $C_1$–$C_4$-alkyl or hydroxy-$C_1$–$C_4$-alkyl substituents and/or one phenyl or benzyl substituent, preferably diisopropylammonium, tetramethylammonium, tetrabutylammonium, trimethylbenzylammonium and tri-methyl-2-hydroxyethylammonium salts, the phosphonium salts, the sulfonium salts, preferably tri-$C_1$–$C_4$-alkyl-sulfonium salts, and the sulfoxonium salts, preferably tri-$C_1$–$C_4$-alkylsulfoxonium salts.

With regard to the use of the novel 3-phenyl-uracils I, Ia and Ib as herbicidal, plant growth-regulating and insecticidal compounds, the variables preferably have the following meanings:

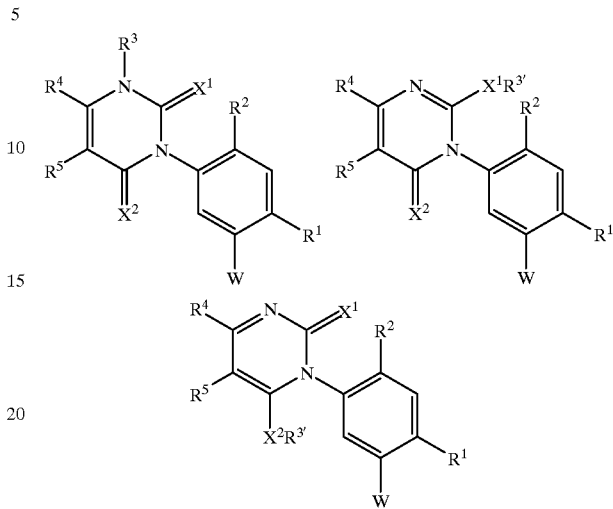

where $X^1$ and $X^2$ independently of one another are each sulfur or oxygen and X, W, $R^1$, $R^2$, $R^3$, $R^4$, $R^{23}$, $R^5$ and $R^{56}$ may be freely combined with one another, with the proviso that $R^4$ cannot be 4.27 if at the same time $R^5$ is 5.01 and W is —$C(R^8)$=$C(R^9)$—CO—$R^{10}$, where $R^8$ is 8.01, $R^9$ is 9.01 and $R^{10}$ is 10.03–10.12 or 10.20–10.23.

$R^1$ is particularly preferably a radical selected from the group consisting of 1.01–1.07, $R^2$ is particularly preferably a radical selected from the group consisting of 2.01–2.05, $R^3$ is particularly preferably a radical selected from the group consisting of 3.01–3.97, $R^{3'}$ is particularly preferably a radical selected from the group consisting of 3'0.01–3'0.17, $R^4$ is particularly preferably a radical selected from the group consisting of 4.01–4.72, $R^5$ is particularly preferably a radical selected from the group consisting of 5.001–5.105 or $R^4$ and $R^5$ together particularly preferably form a radical selected from the group consisting of 45.01–45.54 and W is particularly preferably one of the following radicals W1–W7:

w1 —$C(R^8)(X^3R^6)(R^4R^7)$
w2 —$C(R^8)$=$x^5$,
w3 —$C(R^8)$=$C(R^9)$—CO—$R^{10}$,
w4 —$CR^8$=$CR^9$—$C_2$—CO—$R^{10}$,
w5 —$CR^8$=$CR^9$—$CR^{11}$=$CR^{12}$—CO—$R^{10}$,
w6 —$CR^8$=$CR^9$—$CH_2$—$CHR^{13}$—CO—$R^{10}$;
w7 —$CR^8$=$CR^9$—CN;

where $X^3$ and $X^4$ independently of one another are each 0 or S, $X^5$ is O, S or $NR^{14}$, $R^6$ and $R^7$ independently of one another are each a radical selected from the group consisting of 6.01–6.19, or $R^6$ and $R^7$ together form a radical selected from the group consisting of 67.01–67.63, $R^8$ is a radical selected from the group consisting of 8.01–8.22, $R^9$ and $R^{12}$ are each a radical selected from the group consisting of 9.01–9.23, $R^{10}$ is a radical selected from the group consisting of 10.01–10.144, $R^{11}$ is a radical selected from the group consisting of 11.01–11.25, $R^{13}$ is a radical selected from the group consisting of 13.01–13.08 and $R^{14}$ is a radical selected from the group consisting of 14.001–14.162, and all these radicals may be combined freely with one another.

TABLE 1

| No. | $R^1$ |
|---|---|
| 1.01 | F |
| 1.02 | Cl |
| 1.03 | Br |
| 1.04 | I |
| 1.05 | CN |
| 1.06 | $NO_2$ |
| 1.07 | $CF_3$ |

TABLE 2

| No. | $R^2$ |
|---|---|
| 2.01 | H |
| 2.02 | F |
| 2.03 | Cl |
| 2.04 | Br |
| 2.05 | I |

TABLE 3

| No. | $R^3$ |
|---|---|
| 3.01 | H |
| 3.02 | $CH_3$ |
| 3.03 | $C_2H_5$ |
| 3.04 | n-$C_3H_7$ |
| 3.05 | i-$C_3H_7$ |
| 3.06 | n-$C_4H_9$ |
| 3.07 | i-$C_4H_9$ |
| 3.08 | s-$C_4H_9$ |
| 3.09 | tert.-$C_4H_9$ |
| 3.10 | cyclopropyl |
| 3.11 | cyclobutyl |
| 3.12 | cyclopentyl |
| 3.13 | cyclohexyl |
| 3.14 | cycloheptyl |
| 3.15 | cyclooctyl |
| 3.16 | $CH_2$—CN |
| 3.17 | $CH_2CH_2$—CN |
| 3.18 | $CH(CH_3)CH_2$—CN |
| 3.19 | $C(CH_3)_2$—CN |
| 3.20 | $C(CH_3)_2CH_2$—CN |
| 3.21 | $CH_2Cl$ |
| 3.22 | $CH_2$—$CH_2Cl$ |
| 3.23 | $CH(CH_3)$—$CH_2Cl$ |
| 3.24 | $C(CH_3)_2$—Cl |
| 3.25 | $CHCl_2$ |
| 3.26 | $CF_2Cl$ |
| 3.27 | $CF_3$ |
| 3.28 | $C_2F_5$ |
| 3.29 | $CF_2H$ |
| 3.30 | $CH_2$—CH=$CH_2$ |
| 3.31 | $CH(CH_3)CH=CH_2$ |
| 3.32 | $CH_2$—CH=CH—$CH_3$ |
| 3.34 | $CH_2$-phenyl |
| 3.35 | $CH_2$—C≡CH |
| 3.36 | $CH(CH_3)C≡CH$ |
| 3.37 | $C(CH)_2C≡CH$ |
| 3.38 | phenyl |

TABLE 3-continued

| No. | $R^3$ |
|---|---|
| 3.39 | 2-F-phenyl |
| 3.40 | 3-F-phenyl |
| 3.41 | 4-F-phenyl |
| 3.42 | 2-Cl-phenyl |
| 3.43 | 3-Cl-phenyl |
| 3.44 | 4-Cl-phenyl |
| 3.45 | 2-$CH_3$-phenyl |
| 3.46 | 3-$CH_3$-phenyl |
| 3.47 | 4-$CH_3$-phenyl |
| 3.48 | 2-$CF_3$-phenyl |
| 3.49 | 3-$CF_3$-phenyl |
| 3.50 | 4-$CF_3$-phenyl |
| 3.51 | 2-$OCH_3$-phenyl |
| 3.52 | 3-$OCH_3$-phenyl |
| 3.53 | 4-$OCH_3$-phenyl |
| 3.54 | 4-$COOCH_3$-phenyl |
| 3.56 | 4-$COOC_2H_5$-phenyl |
| 3.57 | 4-$NO_2$-phenyl |
| 3.58 | 4-CN-phenyl |
| 3.59 | 2,4-$Cl_2$-phenyl |
| 3.60 | 2,4-$(CH_3)_2$-phenyl |
| 3.61 | CHO |
| 3.62 | CO—$CH_3$ |
| 3.63 | CO—$C_2H_5$ |
| 3.64 | CO-n-$C_3H_7$ |
| 3.65 | CO-i-$C_3H_7$ |
| 3.66 | CO-n-$C_4H_9$ |
| 3.67 | CO-i-$C_4H_9$ |
| 3.68 | CO-s-$C_4H_9$ |
| 3.69 | CO-tert.-$C_4H_9$ |
| 3.70 | CO-cyclopropyl |
| 3.71 | CO-cyclopentyl |
| 3.72 | Co-cyclohexyl |
| 3.73 | CO—$CF_3$ |
| 3.74 | CO—$CCl_3$ |
| 3.75 | CO—$OCH_3$ |
| 3.76 | CO-$OC_2H_5$ |
| 3.77 | COO-n-$C_3H_7$ |
| 3.78 | COO-i-$C_3H_7$ |
| 3.79 | COO-n-$C_4H_9$ |
| 3.80 | COO-i-$C_4H_9$ |
| 3.81 | COO-s-$C_4H_9$ |
| 3.82 | COO-tert.-$C_4H_9$ |
| 3.83 | $CH_2$—$OCH_3$ |
| 3.84 | $CH(CH_3)$—$OCH_3$ |
| 3.85 | $CH(CH_3)$—$OC_2H_5$ |
| 3.86 | $CH(CH_3)CH_2$—$OCH_3$ |
| 3.87 | $CH_2OC_2H_5$ |
| 3.88 | $NH_2$ |
| 3.89 | $NHCH_3$ |
| 3.90 | $NHC_2H_5$ |
| 3.91 | $N(CH_3)_2$ |
| 3.92 | $N(CH_3)C_2H_5$ |
| 3.93 | NH—CH—CH=$CH_2$ |
| 3.94 | NH—$CH_2C≡CH$ |
| 3.95 | NH-cyclopropyl |
| 3.96 | NH-cyclopentyl |
| 3.97 | NH-cyclohexyl |

TABLE 4

| No. | $R^4$ |
|---|---|
| 4.01 | H |
| 4.02 | F |
| 4.03 | Cl |
| 4.04 | Br |
| 4.05 | I |
| 4.06 | $CH_3$ |
| 4.07 | $C_2H_5$ |
| 4.08 | n-$C_3H_7$ |
| 4.09 | i-$C_3H_7$ |
| 4.10 | n-$C_4H_9$ |
| 4.11 | i-$C_4H_9$ |

TABLE 4-continued

| No. | R⁴ |
|---|---|
| 4.12 | s-$C_4H_9$ |
| 4.13 | tert.-$C_4H_9$ |
| 4.14 | cyclopropyl |
| 4.15 | cyclobutyl |
| 4.16 | cyclopentyl |
| 4.17 | cyclohexyl |
| 4.18 | cycloheptyl |
| 4.19 | cyclooctyl |
| 4.20 | CN |
| 4.21 | $CH_2Cl$ |
| 4.22 | $CHCH_2Cl$ |
| 4.23 | $CH(CH_2Cl$ |
| 4.24 | $CHCl_2$ |
| 4.25 | $CCl_3$ |
| 4.26 | $CF_2Cl$ |
| 4.27 | $CF_3$ |
| 4.28 | $C_2F_5$ |
| 4.29 | $CF_2H$ |
| 4.30 | $CH=CH_2$ |
| 4.31 | $CH_2-CH=CH_2$ |
| 4.32 | $CH_2-CH=CH-CH_3$ |
| 4.33 | C≡CH |
| 4.34 | $CH_2-C≡CH$ |
| 4.35 | $CH(CH_3)-C≡CH$ |
| 4.36 | phenyl |
| 4.37 | 2-F-phenyl |
| 4.38 | 3-F-phenyl |
| 4.39 | 4-F-pnenyl |
| 4.40 | 2-Cl-phenyl |
| 4.41 | 3-Cl-phenyl |
| 4.42 | 4-Cl-phenyl |
| 4.43 | 2-$CH_3$-phenyl |
| 4.44 | 3-$CH_3$-phenyl |
| 4.45 | 4-$CH_3$-phenyl |
| 4.46 | 2-$CF_3$-phenyl |
| 4.47 | 3-$CF_3$-phenyl |
| 4.48 | 4-$CF_3$-phenyl |
| 4.49 | 2-$OCH_3$-phenyl |
| 4.50 | 3-$OCH_3$-phenyl |
| 4.51 | 4-$OCH_3$-phenyl |
| 4.52 | 4-$COOCH_3$-phenyl |
| 4.53 | 4-$COOC_2H_5$-phenyl |
| 4.54 | 4-$NO_2$-phenyl |
| 4.55. | 4-CN-phenyl |
| 4.56 | 2,-J-$Cl_2$-phenyl |
| 4.57 | 2,6-$Cl_2$-phenyl |
| 4.58 | 2,4-$(CH_3)_2$-phenyl |
| 4.59 | $CH_2-OCH_3$ |
| 4.60 | $CH_2-OC_2H_5$ |
| 4.61 | $CH_2CH_2-OCH_3$ |
| 4.62 | $CH_2CH_2-OC_2H_5$ |
| 4.63 | $CH(CH_3)-OCH_3$ |
| 4.64 | $CH_2-OH$ |
| 4.65 | $CH_2CH_2-OH$ |
| 4.66 | $CH_2CN$ |
| 4.67 | $CH_2CH_2-CN$ |
| 4.68 | $CH_2SCH_3$ |
| 4.69 | $CH_2CH_2-SCH_3$ |
| 4.70 | $CH_2CH_2-SC_2H_5$ |
| 4.71 | $CH_2CH_2-S-i-C_3H_7$ |
| 4.72 | $CH_2-SC_2H_5$ |

TABLE 5

| No. | R⁵ |
|---|---|
| 5.001 | H |
| 5.002 | F |
| 5.003 | Cl |
| 5.004 | Br |
| 5.005 | I |
| 5.006 | $CH_3$ |
| 5.007 | $C_2H_5$ |
| 5.008 | n-$C_3H_7$ |
| 5.009 | i-$C_3H_7$ |
| 5.010 | n-$C_4H_9$ |
| 5.011 | i-$C_4H_9$ |
| 5.012 | s-$C_4H_9$ |
| 5.013 | tert.-$C_4H_9$ |
| 5.014 | n-$C_5H_{11}$ |
| 5.015 | n-$C_6H_{13}$ |
| 5.016 | cyclopropyl |
| 5.017 | cyclobutyl |
| 5.018 | cyclopentyl |
| 5.019 | cyclohexyl |
| 5.020 | cycloheptyl |
| 5.021 | cyclooctyl |
| 5.022 | CN |
| 5.023 | $CH_2Cl$ |
| 5.024 | $CH_2CH_2-Cl$ |
| 5.025 | $CH(CH_3)CH_2-Cl$ |
| 5.026 | $CHCl_2$ |
| 5.027 | $CCl_3$ |
| 5.028 | $CF_2Cl$ |
| 5.029 | $CF_3$ |
| 5.030 | $C_2F_5$ |
| 5.031 | $CF_2H$ |
| 5.032 | $CH=CH_2$ |
| 5.033 | $CH_2-CH=CH_2$ |
| 5.034 | $CH_2-CH=CH-CH_3$ |
| 5.035 | C≡CH |
| 5.036 | $CH_2-C≡CH$ |
| 5.037 | $CH(CH_3)-C≡CH$ |
| 5.038 | phenyl |
| 5.039 | 2-F-pheny |
| 5.040 | 3-F-phenyl |
| 5.041 | 4-F-phenyl |
| 5.042 | 2-Cl-phenyl |
| 5.043 | 3-Cl-phenyl |
| 5.044 | 4-Cl-phenyl |
| 5.045 | 2-$CH_3$—phenyl |
| 5.046 | 3-$CH_3$—phenyl |
| 5.047 | 4-$CH_3$—phenyl |
| 5.048 | 2-$CF_3$—phenyl |
| 5.049 | 3-$CF_3$—phenyl |
| 5.050 | 4-$CF_3$—phenyl |
| 5.051 | 2-$OCH_3$-phenyl |
| 5.052 | 3-$OCH_3$-phenyl |
| 5.053 | 4-$CoOCH_3$-phenyl |
| 5.054 | 4-$COOC_2H_5$-phenyl |
| 5.055 | 4-$SCF_3$-phenyl |
| 5.056 | 4-$NO_2$-phenyl |
| 5.057 | 4-CN-phenyl |
| 5.058 | 2,4-$C_{12}$-phenyl |
| 5.059 | 2,6-$Cl_2$-phenyl |
| 5.060 | 2,4-$(CH_3)_2$-phenyl |
| 5.061 | CHO |
| 5.062 | CO—$CH_3$ |
| 5.063 | CO—$C_2H_5$ |
| 5.064 | CO-n-$C_3H_7$ |
| 5.065 | CO-i-$C_3H_7$ |
| 5.066 | CO-n-$C_4H_9$ |
| 5.067 | CO-i-$C_4H_9$ |
| 5.068 | CO-s-$C_4H_9$ |
| 5.069 | CO-tert.-$C_4H_9$ |
| 5.070 | CO—$C_5H_{11}$ |
| 5.071 | CO—$C_6H_{13}$ |
| 5.072 | CO—$CF_3$ |
| 5.073 | CO—$CCl_3$ |
| 5.074 | COO—$CH_3$ |
| 5.075 | COO—$C_2H_5$ |
| 5.076 | COO-n-$C_3H_7$ |
| 5.077 | COO-i-$C_3H_7$ |
| 5.078 | COO-n-$C_4H_9$ |
| 5.079 | COO-i-$C_4H_9$ |
| 5.080 | COO-s-$C_4H_9$ |
| 5.081 | COO-tert.-$C_4H_9$ |
| 5.082 | $CH_2-OCH_3$ |
| 5.083 | $CH_2-OC_2H_5$ |
| 5.084 | $CH_2CH_2-OCH_3$ |
| 5.085 | $CH_2CH_2-OC_2H_5$ |

TABLE 5-continued

| No. | $R^5$ |
|---|---|
| 5.087 | $CH(CH_3)-OCH_3$ |
| 5.088 | $CH_2OH$ |
| 5.089 | $CH_2CH_2-OH$ |
| 5.090 | $CH_2CN$ |
| 5.091 | $CH_2CH_2-CN$ |
| 5.092 | $CH_2-SCH_3$ |
| 5.093 | $CH_2CH_2-SCH_3$ |
| 5.094 | $CH_2CH_2-SC_2H_5$ |
| 5.095 | $CH_2CH_2-S-i-C_3H_7$ |
| 5.096 | $CH_2-SC_2H_5$ |
| 5.097 | $NO_2$ |
| 5.098 | $NH_2$ |
| 5.099 | $NH(CH_3)$ |
| 5.100 | $N(CH_3)_2$ |
| 5.101 | $NH(C_2H_5)$ |
| 5.102 | $N(C_2H_5)_2$ |
| 5.103 | $N(CH_3)(C_2H_5)$ |
| 5.104 | $CH=CH-CO_2CH_3$ |
| 5.105 | $CH=CH-CO_2CH_2CH_3$ |

TABLE 6

| No. | $R^4 + R^5$ |
|---|---|
| 45.01 | $-(CH_2)_3-$ |
| 45.02 | $-(CH_2)_4-$ |
| 45.03 | $-CH(CH_3)-(CH_2)_3-$ |
| 45.04 | $-CH_2-CH(CH_3)-(CH_2)_2-$ |
| 45.05 | $-(CH_2)_2-CH(CH_3)-CH_2-$ |
| 45.06 | $-(CH_2)_3-CH(CH_3)-$ |
| 45.07 | $-CH_2-)-CH_2-$ |
| 45.08 | $-(CH_2)_2-O-$ |
| 45.09 | $-CH_2-O-(CH_2)_2-$ |
| 45.10 | $-(CH_2)_2-O-CH_2-$ |
| 45.11 | $-S-(CH_2)_2-$ |
| 45.12 | $-CH_2-S-CH_2-$ |
| 45.13 | $-(CH_2)_2-S-$ |
| 45.14 | $-S-(CH_2)_3-$ |
| 45.15 | $-CH_2-S-(CH_2)_2-$ |
| 45.16 | $-(CH_2)_2-S-CH_2-$ |
| 45.17 | $-(CH_2)_3-S-$ |
| 45.18 | $-O-CH=CH-$ |
| 45.19 | $-CH=CH-O-$ |
| 45.20 | $-S-CH=CH-$ |
| 45.21 | $-CH=CH-S-$ |
| 45.22 | $-NH-CH=CH-$ |
| 45.23 | $-NCH_3-CH=CH-$ |
| 45.24 | $-CH=CH-NH-$ |
| 45.25 | $-CH=CH-NCH_3-$ |
| 45.26 | $-N=CH-CH=CH-$ |
| 45.27 | $-CH=N-CH=CH-$ |
| 45.28 | $-CH=CH-N=CH-$ |
| 45.29 | $-CH=CH-CH=N-$ |
| 45.30 | $-CH=N-O-$ |
| 45.31 | $-O-N=CH-$ |
| 45.32 | $-O-CH=N-$ |
| 45.33 | $-N=CH-O-$ |
| 45.34 | $-CH=N-S-$ |
| 45.35 | $-S-N=CH-$ |
| 45.36 | $-S-CH=N-$ |
| 45.37 | $-N=CH-S-$ |
| 45.38 | $-N=CH-NH-$ |
| 45.39 | $-N=CH-NCH_3-$ |
| 45.40 | $-NH-CH=N-$ |
| 45.41 | $-N(CH_3)-CH=N-$ |
| 45.42 | $-CH=CH-CH=CH-$ |
| 45.43 | $-NH-CH=CH-NH-$ |
| 45.44 | $-N=N-CH=CH-$ |
| 45.45 | $-S-C(CH_3)=N-$ |
| 45.46 | $-C(NO_2)-CH-S-$ |
| 45.47 | $-C(CN)=CH-S-$ |
| 45.48 | $-C(NO_2)=CH-O-$ |
| 45.49 | $-C(CN)=CH-O-$ |
| 45.50 | $-N(CH_3)-CH-CH-N(CH_3)-$ |

TABLE 6-continued

| No. | $R^4 + R^5$ |
|---|---|
| 45.51 | $-CH=CH-N=N-$ |
| 45.52 | $-N=N-NH-$ |
| 45.53 | $-N=N-N(CH_3)-$ |
| 45.54 | $-CH-S-CH-$ |

TABLE 7

| No. | $R^6$ or $R^7$ |
|---|---|
| 6.01 | $CH_3$ |
| 6.02 | $C_2H_5$ |
| 6.03 | $n-C_3H_7$ |
| 6.04 | $i-C_3H_7$ |
| 6.05 | $n-C_4H_9$ |
| 6.06 | $i-C_4H_9$ |
| 6.07 | $s-C_4H_9$ |
| 6.08 | $tert.-C_4H_9$ |
| 6.09 | $n-C_5H_{11}$ |
| 6.10 | $n-C_6H_{13}$ |
| 6.11 | $CH_2CH=CH_2$ |
| 6.12 | $CH(CH_3)-CH=CH_2$ |
| 6.13 | $CH_2C\equiv CH$ |
| 6.14 | $CH(CH_3)C\equiv CH$ |
| 6.15 | $CH_2OCH_3$ |
| 6.16 | $C_2H_4OCH_3$ |
| 6.17 | $C_2H_4OC_2H_5$ |
| 6.18 | $(CH_2)_3-Cl$ |
| 6.19 | $CH_2CH_2-Cl$ |

TABLE 8

| No. | $R^6 + R^7$ |
|---|---|
| 67.01 | $-(CH_2)_2-$ |
| 67.02 | $-CH(CH_3)-CH_2-$ |
| 67.03 | $-CH(C_2H_5)-CH_2-$ |
| 67.04 | $-CH(CH_3)-CH-(CH_3)-$ |
| 67.05 | $-C(CH_3)_2-CH_2-$ |
| 67.06 | $-CH(CH=CH_2)-CH_2-$ |
| 67.07 | $-CH(CH_2Cl)-CH_2-$ |
| 67.08 | $-CH(CH_2Br)-CH_2-$ |
| 67.09 | $-CH(CH_2OH)-CH_2-$ |
| 67.10 | $-CH(CH_2OCH_3)-CH_2-$ |
| 67.11 | $-CH(CH_2OC_2H_5)-CH_2-$ |
| 67.12 | $-CH(CH_2OCH_2CH=CH_2)-CH_2-$ |
| 67.13 | $-CH(CH_2OCH_2C\equiv CH)-CH_2-$ |
| 67.14 | $-CH(COOH)-CH_2-$ |
| 67.15 | $-CH(COOCH_3)-CH_2-$ |
| 67.16 | $-CH(COOC_2H_5)-CH_2-$ |
| 67.17 | $-CH(COO-n-C_3H_7)-CH_2-$ |
| 67.18 | $-CH(COO-i-C_3H_7)-CH_2-$ |
| 67.19 | $-CH(COO-n-C_4H_9)-CH_2-$ |
| 67.20 | $-CH(COO-n-C_5H_{11})-CH_2-$ |
| 67.21 | $-CH(COO-n-C_6H_{13})-CH_2-$ |
| 67.22 | $-(CH_2)_3-$ |
| 67.23 | $-CH(CH_3)-(CH_2)_2-$ |
| 67.24 | $-CH_2-CH(CH_3)-CH_2-$ |
| 67.25 | $-CH(C_2H_5)-(CH_2)_2-$ |
| 67.26 | $-CH_2-CH(C_2H_5)-CH_2-$ |
| 67.27 | $-CH(CH_3)-CH_2-CH(CH_3)-$ |
| 67.28 | $-CH_2-C(CH_3)_2-CH_2-$ |
| 67.29 | $-CH(CH_2OH)-(CH_2)_2-$ |
| 67.30 | $-CH_2-CH(CH_2OH)-CH_2$ |
| 67.31 | $-CH(CH_2OCH_3)-(CH_2)_2-$ |
| 67.32 | $-CH(CH_2OCH_2CH=CH_2)-(CH_2)_2-$ |
| 67.33 | $-CH(CH_2O-CO-CH_3)-CH_2-$ |
| 67.33 | $-CH(CH_2OCH_2C\equiv CH)-(CH_2)_2-$ |
| 67.34 | $-CH(CH_2OC(O)CH_3)-(CH_2)_2-$ |
| 67.35 | $-CH_2-CH(CH_2OCH_3)-CH_2-$ |
| 67.36 | $-CH_2-CH(CH_2OCH_2CH=CH_2)-CH_2-$ |
| 67.37 | $-CH_2-CH(CH_2OCH_2C\equiv CH)-CH_2-$ |
| 67.38 | $-CH_2-CH(CH_2OC(O)CH_3)-CH_2-$ |

TABLE 8-continued

| No. | $R^6 + R^7$ |
|---|---|
| 67.39 | —CH(CH$_2$Cl)—(CH$_2$)$_2$— |
| 67.40 | —CH$_2$—CH(CH$_2$Cl)—CH$_2$— |
| 67.41 | —C(CH$_3$)—(COOCH$_3$)—CH$_2$— |
| 67.42 | —C(CH$_3$)—(COOC$_2$H$_5$)—CH$_2$— |
| 67.43 | —C(CH$_3$)(COO-n-C$_3$H$_7$)—CH$_2$— |
| 67.44 | —C(CH$_3$)(COO-n-C$_4$H$_6$)—CH$_2$— |
| 67.45 | —CH(CH$_2$CN)—CH$_2$— |
| 67.46 | —CH(CH$_2$CN)—(CH$_2$)$_2$— |
| 67.47 | —CH$_2$—CH(CH$_2$CN)—CH$_2$— |
| 67.48 | —CH$_2$—O—CH$_2$— |
| 67.49 | —CH$_2$—NH—CH$_2$— |
| 67.50 | —CH$_2$—N(CH$_3$)—CH$_2$ |
| 67.51 | —(CH$_2$)$_4$— |
| 67.52 | —CH$_2$—CH=CH—CH$_2$— |
| 67.53 | —CH$_2$—O—(CH$_2$)$_2$— |
| 67.54 | —CO—CH$_2$— |
| 67.55 | —CO—(CH$_2$)$_2$— |
| 67.56 | —CH$_2$—CO—CH$_2$— |
| 67.57 | —CO—C(CH$_3$)$_2$— |
| 67.58 | —CO—O—CH$_2$— |
| 67.59 | —CH$_2$—S—CH$_2$— |
| 67.60 | —CH(CH$_2$O—CO—CH$_3$)—CH$_2$— |
| 67.61 | 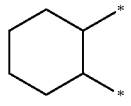 |
| 67.62 | 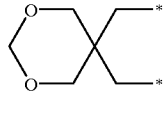 |
| 67.63 | 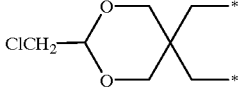 |

(— = bonding valency)

TABLE 9

| No. | $R^8$ |
|---|---|
| 8.01 | H |
| 8.02 | CH$_3$ |
| 8.03 | C$_2$H$_5$ |
| 8.04 | n-C$_3$H$_7$ |
| 8.05 | i-C$_3$H$_7$ |
| 8.06 | n-C$_4$H$_9$ |
| 8.07 | i-C$_4$H$_9$ |
| B.08 | s-C$_4$H$_9$ |
| 8.09 | tert.-C$_4$H$_9$ |
| 8.10 | n-C$_5$H$_{11}$ |
| 8.11 | n-C$_6$H$_{13}$ |
| 8.12 | CH$_2$—CH=CH$_2$ |
| 8.13 | CH$_2$—C≡CH |
| 8.14 | CF$_3$ |
| 8.15 | CCl$_3$ |
| 8.16 | cyclopropyl |
| 8.17 | cyclobutyl |
| 8.18 | cyclopentyl |
| 8.19 | cyclohexyl |
| 8.20 | CN |
| 8.21 | CO—OCH$_3$ |
| 8.22 | CO—OC$_2$H$_5$ |

TABLE 10

| No. | $R^9$ and $R^{12}$ |
|---|---|
| 9.01 | H |
| 9.02 | F |
| 9.03 | Cl |
| 9.04 | Br |
| 9.05 | I |
| 9.06 | CN |
| 9.07 | CH$_3$ |
| 9.08 | C$_2$H$_5$ |
| 9.09 | n-C$_3$H$_7$ |
| 9.10 | i-C$_3$H$_7$ |
| 9.11 | n-C$_4$H$_9$ |
| 9.12 | i-C$_4$H$_9$ |
| 9.13 | s-C$_4$H$_9$ |
| 9.14 | tert.-C$_4$H$_9$ |
| 9.15 | n-C$_5$H$_{11}$ |
| 9.16 | OCH$_3$ |
| 9.17 | OC$_2$H$_5$ |
| 9.18 | CF$_3$ |
| 9.19 | CO—CH$_3$ |
| 9.20 | CO—C$_2$H$_5$ |
| 9.21 | COOCH$_3$ |
| 9.22 | COOC$_2$H$_5$ |
| 9.23 | COO-n-C$_3$H$_7$ |

TABLE 11

| No. | $R^{10}$ |
|---|---|
| 10.01 | H |
| 10.02 | OH |
| 10.03 | OCH$_3$ |
| 10.04 | OC$_2$H$_5$ |
| 10.05 | O-n-C$_3$H$_7$ |
| 10.06 | O-i-C$_3$H$_7$ |
| 10.07 | O-n-C$_4$H$_9$ |
| 10.08 | O-i-C$_4$H$_9$ |
| 10.09 | O-s-C$_4$H$_9$ |
| 10.10 | O-tert.-C$_4$H$_9$ |
| 10.11 | O-n-C$_5$H$_{11}$ |
| 10.12 | O-n-C$_6$H$_{13}$ |
| 10.14 | O—CH$_2$CH=CH$_2$ |
| 10.15 | O—CH(CH$_3$)CH=CH$_2$ |
| 10.16 | O—CH—CH=CH—CH$_2$ |
| 10.17 | O—CH$_2$—C≡CH |
| 10.18 | O—CH(CH$_3$)—C≡CH |
| 10.19 | O—CH$_2$—CC—CH$_3$ |
| 10.20 | O-cyclopropyl |
| 10.21 | O-cyclobutyl |
| 10.22 | O-cyclopentyl |
| 10.23 | O-cyclohexyl |
| 10.24 | O—CH$_2$—CF$_3$ |
| 10.25 | O—CH$_2$—CCl$_3$ |
| 10.26 | O—(CH$_2$)$_3$—Br |
| 10.27 | O-phenyl |
| 10.28 | O-2F-phenyl |
| 10.29 | O-2Cl-phenyl |
| 10.30 | O-2Br-phenyl |
| 10.31 | O-3F-phenyl |
| 10.32 | O-3Cl-phenyl |
| 10.33 | O-3-Br-phenyl |
| 10.34 | O-4-F-phenyl |
| 10.35 | O-4-Cl-phenyl |
| 10.36 | O-4-Br-phenyl |
| 10.37 | O-4-OCH$_3$-phenyl |
| 10.38 | O-4-CN-phenyl |
| 10.39 | O-4-COOCH$_3$-phenyl |
| 10.40 | O-4-CH$_3$—phenyl |
| 10.41 | O-2,4-Cl$_2$-phenyl |
| 10.42 | O-2,4-(CH$_3$)$_2$-phenyl |
| 10.43 | O—CH$_2$CN |
| 10.44 | O—CH$_2$CH=CCl$_2$ |
| 10.45 | O—CH$_2$CH=CHCl |
| 10.46 | O—CH$_2$OCH$_3$ |
| 10.47 | O—CH$_2$OC$_2$H$_5$ |

TABLE 11-continued

| No. | R$^{10}$ |
|---|---|
| 10.48 | O—C$_2$H$_4$OCH$_3$ |
| 10.49 | O—C$_2$H$_4$OC$_2$H$_5$ |
| 10.50 | O—CH(CH$_3$)—OCH$_3$ |
| 10.51 | O—CH(CH$_3$)—OC$_2$H$_5$ |
| 10.52 | O—CH$_2$CH=NOCH$_3$ |
| 10.53 | O—C$_2$H$_4$CH=NOCH$_3$ |
| 10.54 | O—CH$_2$CH=NOC$_2$H$_5$ |
| 10.55 | O—C(O)CH$_3$ |
| 10.56 | O—C(O)C$_2$H$_5$ |
| 10.57 | O—C$_2$H$_4$CH=NOC$_2$H$_5$ |
| 10.58 | SCH$_3$ |
| 10.59 | SC$_2$H$_5$ |
| 10.60 | S-n-C$_3$H$_7$ |
| 10.61 | S-i-C$_3$H$_7$ |
| 10.62 | S—CH$_2$CH=CH$_2$ |
| 10.63 | S—CH$_2$C≡CH |
| 10.64 | S-phenyl |
| 10.65 | S—CH$_2$CN |
| 10.66 | S—CH$_2$OCH$_3$ |
| 10.67 | CH$_3$ |
| 10.68 | C$_2$H$_5$ |
| 10.69 | n-C$_3$H$_7$ |
| 10.70 | i-C$_3$H$_7$ |
| 10.71 | n-C$_4$H$_9$ |
| 10.72 | i-C$_4$H$_9$ |
| 10.73 | s-C$_4$H$_9$ |
| 10.74 | tert.-C$_4$H$_9$ |
| 10.75 | n-C$_5$H$_{11}$ |
| 10.76 | n-C$_6$H$_{13}$ |
| 10.77 | CH$_2$CH=CH$_2$ |
| 10.78 | CH$_2$C≡CH |
| 10.79 | CH(CH$_3$)CH=CH$_2$ |
| 10.80 | CH(CH$_3$)C≡CH |
| 10.81 | CH$_2$Cl |
| 10.82 | CH$_2$Br |
| 10.83 | CHCl$_2$ |
| 10.84 | CF$_3$ |
| 10.85 | cyclopropyl |
| 10.86 | cyclobutyl |
| 10.87 | cyclopentyl |
| 10.88 | cyclohexyl |
| 10.89 | phenyl |
| 10.90 | 2-F-phenyl |
| 10.91 | 3-F-phenyl |
| 10.92 | 4-F-phenyl |
| 10.93 | 2-Cl-phenyl |
| 10.94 | 4-Cl-phenyl |
| 10.95 | 2,4-Cl$_2$-phenyl |
| 10.96 | CH$_2$—OCH$_3$ |
| 10.97 | CH(OCH$_3$)$_2$ |
| 10.98 | CH$_2$—SCH$_3$ |
| 10.99 | NH$_2$ |
| 10.100 | NHCH$_3$ |
| 10.101 | NHCH$_3$ |
| 10.102 | NH-n-C$_3$H$_7$ |
| 10.103 | NH-i-C$_3$H$_7$ |
| 10.104 | NH-n-C$_4$H$_9$ |
| 10.105 | N(CH$_3$)$_2$ |
| 10.106 | N(C$_2$H$_5$)$_2$ |
| 10.107 | N(CH$_3$)C$_2$H$_5$ |
| 10.108 | N(n-C$_3$H$_7$)$_2$ |
| 10.109 | NH—CH$_2$CH=CH$_2$ |
| 10.110 | NH—CH(CH$_3$)—CH=CH$_2$ |
| 10.111 | NH—CH$_2$C≡CH |
| 10.112 | NH—CH(CH$_3$)—C≡CH |
| 10.113 | N(CH$_3$)—CH$_2$CH=CH |
| 10.114 | N(CH$_3$)—CH$_2$C≡CH |
| 10.115 | NH-cyclopropyl |
| 10.116 | NH-cyclobutyl |
| 10.117 | NH-cyclopentyl |
| 10.118 | NH-cyclohexyl |
| 10.119 | N(CH$_3$)-cyclohexyl |
| 10.120 | N(C$_2$H$_5$)-cyclohexyl |
| 10.121 | NH—COCH$_3$ |
| 10.122 | NH—COC$_2$H$_5$ |
| 10.123 | NH—COOCH$_3$ |
| 10.124 | NH—CH$_2$OCH$_3$ |
| 10.125 | NH—(CH$_2$)$_2$OCH$_3$ |
| 10.126 | N-piperindinyl |
| 10.127 | N-pyrrolidinyl |
| 10.128 | N-morpholino |
| 10.129 | N-piperazinyl |
| 10.130 | NH-phenyl |
| 10.131 | NH-2—CH$_3$—phenyl |
| 10.132 | NH-2-F-phenyl |
| 10.133 | NH-4-F-phenyl |
| 10.134 | NH-2-Cl-phenyl |
| 10.135 | NH-4-Cl-phenyl |
| 10.136 | NH-2,4-Cl$_2$-phenyl |
| 10.137 | O—CO—OCH$_3$ |
| 10.138 | O—CO—OC$_2$H$_5$ |
| 10.139 | CH$_2$—OC$_2$H$_5$ |
| 10.140 | CH(OC$_2$H$_5$)$_2$ |
| 10.141 | OCH$_2$COOCH$_3$ |
| 10.142 | OCH$_2$COOC$_2$H$_5$ |
| 10.143 | OCH(CH$_3$)COOCH$_3$ |
| 10.144 | OCH(CH$_3$)COOC$_2$H$_5$ |

TABLE 12

| No. | R$^{11}$ |
|---|---|
| 11.01 | H |
| 11.02 | F |
| 11.03 | Cl |
| 11.04 | Br |
| 11.05 | I |
| 11.06 | CN |
| 11.07 | CH$_3$ |
| 11.08 | C$_2$H$_5$ |
| 11.09 | n-C$_3$H$_7$ |
| 11.10 | i-C$_3$H$_7$ |
| 11.11 | n-C$_4$H$_9$ |
| 11.12 | i-C$_4$H$_9$ |
| 11.13 | s-C$_4$H$_9$ |
| 11.14 | tert.-C$_4$H$_9$ |
| 11.15 | CH$_2$—CH=CH$_2$ |
| 11.16 | CH$_2$—C≡CH |
| 11.17 | phenyl |
| 11.18 | 4-Cl-phenyl |
| 11.19 | N(CH$_3$)$_2$ |
| 11.20 | COOCH$_3$ |
| 11.21 | COOC$_2$H$_5$ |
| 11.22 | COCH$_3$ |
| 11.23 | COC$_2$H$_5$ |
| 11.24 | CH$_2$OCH$_3$ |
| 11.25 | (CH$_2$)$_2$—OCH$_3$ |

TABLE 13

| No. | R$^{13}$ |
|---|---|
| 13.01 | H |
| 13.02 | CN |
| 13.03 | CH$_3$ |
| 13.04 | C$_2$H$_5$ |
| 13.05 | n-C$_3$H$_7$ |
| 13.06 | i-C$_3$H$_7$ |
| 13.07 | COOCH$_3$ |
| 13.08 | COOC$_2$H$_5$ |

TABLE 14

| No. | R$^{14}$ |
|---|---|
| 14.01 | H |
| 14.02 | CH$_3$ |

TABLE 14-continued

| No. | R$^{14}$ |
|---|---|
| 14.03 | C$_2$H$_5$ |
| 14.04 | n-C$_3$H$_7$ |
| 14.05 | i-C$_3$H$_7$ |
| 14.06 | n-C$_4$H$_9$ |
| 14.07 | n-C$_5$H$_{11}$ |
| 14.08 | n-C$_6$H$_{13}$ |
| 14.10 | CH$_2$CH=CH$_2$ |
| 14.11 | CH(CH$_3$)—CH=CH$_2$ |
| 14.12 | CH$_2$—CH=CH—CH$_3$ |
| 14.13 | CH$_2$—C≡CH |
| 14.14 | CH(CH$_3$)—C≡CH |
| 14.15 | CH$_2$—C≡C—CH$_3$ |
| 14.16 | cyclopropyl |
| 14.17 | cyclobutyl |
| 14.18 | cyclopentyl |
| 14.19 | cyclohexyl |
| 14.20 | cycloheptyl |
| 14.22 | (CH$_2$)$_2$Cl |
| 14.23 | CH$_2$Cl |
| 14.25 | phenyl |
| 14.26 | 2-F-phenyl |
| 14.27 | 3-F-phenyl |
| 14.28 | 4-F-phenyl |
| 14.29 | 2-Cl-phenyl |
| 14.30 | 3-Cl-phenyl |
| 14.31 | 4-Cl-phenyl |
| 14.32 | 2-Br-phenyl |
| 14.33 | 3-Br-phenyl |
| 14.34 | 4-Br-phenyl |
| 14.35 | 2-CH$_3$-phenyl |
| 14.36 | 3-CH$_3$-phenyl |
| 14.37 | 4-CH$_3$-phenyl |
| 14.28 | 2-CF$_3$-phenyl |
| 14.39 | 3-CF$_3$-phenyl |
| 14.40 | 4-CF$_3$-phenyl |
| 14.41 | 2-OCH$_3$-phenyl |
| 14.42 | 3-OCH$_3$-phenyl |
| 14.43 | 4-OCH$_3$-phenyl |
| 14.44 | 4-NO$_2$-phenyl |
| 14.45 | 4-CN-phenyl |
| 14.46 | 2,4-Cl$_2$-phenyl |
| 14.47 | 2,4-(CH$_3$)$_2$-phenyl |
| 14.48 | CH$_2$—OCH$_3$ |
| 14.49 | (CH$_2$)$_2$—OC$_2$H$_5$ |
| 14.50 | OH |
| 14.51 | OCH$_3$ |
| 14.52 | OC$_2$H$_5$ |
| 14.53 | O-n-C$_3$H$_7$ |
| 14.54 | O-i-C$_3$H$_7$ |
| 14.55 | O-n-C$_4$H$_9$ |
| 14.56 | O-i-C$_4$H$_9$ |
| 14.57 | O-s-C$_4$H$_9$ |
| 14.58 | O-tert.-C$_4$H$_9$ |
| 14.59 | O—CH$_2$CH=CH$_2$ |
| 14.60 | O—CH(CH$_3$)CH=CH$_2$ |
| 14.61 | O—CH$_2$C≡CH |
| 14.62 | O—CH(CH$_3$)—C≡CH |
| 14.63 | O—CH$_2$—C≡C—CH$_3$ |
| 14.64 | O—CH$_2$—CH=CH—CH$_3$ |
| 14.65 | O-cyclopentyl |
| 14.66 | O-cyclohexyl |
| 14.67 | O-cyclopent-3-enyl |
| 14.68 | O-cyclohex-3-enyl |
| 14.69 | O—(CH$_2$)$_2$—Cl |
| 14.70 | O—(CH$_2$)$_2$—Cl |
| 14.71 | O—(CH$_2$)—F |
| 14.72 | O—(CH$_2$)$_2$—CF$_3$ |
| 14.73 | O—(CH$_2$)$_2$—Br |
| 14.74 | O—CH$_2$—CH=CHCl |
| 14.75 | O—CH$_2$—C(Cl)=CH$_2$ |
| 14.76 | O—CH$_2$—C(Br)=CH$_2$ |
| 14.77 | O—CH$_2$—CH=C(Cl)—CH$_3$ |
| 14.78 | O—CH$_2$—C(Cl)=CCl$_2$ |
| 14.79 | O—CH$_2$-cyclopropyl |
| 14.80 | O—CH$_2$-cyclobutyl |
| 14.81 | O—CH$_2$-cyclopentyl |
| 14.82 | O—CH$_2$-cyclohexyl |
| 14.83 | O—CH$_2$-cycloheptyl |
| 14.84 | O—CO—CH$_3$ |
| 14.85 | O—CO—C$_2$H$_5$ |
| 14.86 | O—CH$_2$—CN |
| 14.87 | O—(CH$_2$)$_3$—CN |
| 14.88 | O—CH$_2$—OCH$_3$ |
| 14.89 | O—CH$_2$—OC$_2$H$_5$ |
| 14.90 | O—(CH$_2$)$_2$—OCH$_3$ |
| 14.91 | O—(CH$_2$)$_2$—OC$_2$H$_5$ |
| 14.92 | O—(CH$_2$)$_3$—OC$_2$H$_5$ |
| 14.93 | O—(CH$_2$)$_2$—CO—OCH$_3$ |
| 14.94 | O—(CH$_2$)$_2$—CO—OC$_2$H$_5$ |
| 14.95 | O—C(CH$_3$)$_2$—CO—OCH$_3$ |
| 14.96 | O—C(CH$_3$)$_2$—CO—OC$_2$H$_5$ |
| 14.97 | O—(CH$_2$)$_2$—OH |
| 14.98 | O—CH$_2$—SCH$_3$ |
| 14.99 | O—(CH$_2$)$_2$—N(CH$_3$)$_2$ |
| 14.100 | O—(CH$_2$)$_2$—N(C$_2$H$_5$)$_2$ |
| 14.101 | O—CH$_2$-phenyl |
| 14.102 | O—(CH$_2$)$_2$-phenyl |
| 14.103 | O—(CH$_2$)$_3$-phenyl |
| 14.104 | O—(CH$_2$)$_4$-phenyl |
| 14.105 | O—(CH$_2$)$_4$-(4-Cl-phenyl) |
| 14.106 | O—(CH$_2$)$_4$-(4-CH$_3$-phenyl) |
| 14.107 | O—(CH$_2$)$_4$-(4-CH$_3$-phenyl) |
| 14.108 | O—(CH$_2$)$_4$-(4-F-phenyl) |
| 14.109 | O—CH$_2$CH=CH-phenyl |
| 14.110 | O—CH$_2$CH=CH-(4-F-phenyl) |
| 14.111 | O—CH$_2$CH=CH-(4-Cl-phenyl) |
| 14.112 | O—CH$_2$CH=CH-(3-OCH$_3$-phenyl) |
| 14.113 | O—(CH$_2$)$_2$—CH=CH-(4-F-phenyl) |
| 14.114 | O—(CH$_2$)$_2$—CH=CH-(4-Cl-phenyl) |
| 14.115 | O—(CH$_2$)—CH=CH-(3,4-Cl$_2$-phenyl) |
| 14.116 | O—CH$_2$—CH=C(CH$_3$)-(4-F-phenyl) |
| 14.117 | O—CH$_2$—C≡C—CH$_2$-phenyl |
| 14.119 | O—(CH$_2$)$_2$—O-phenyl |
| 14.120 | O—(CH$_2$)$_2$—OCH$_2$-phenyl |
| 14.121 | O—(CH$_2$)$_2$—OCH$_2$-(4-F-phenyl) |
| 14.122 | O—CH$_2$CH=CH—CH$_2$—O-phenyl |
| 14.123 | O—CH$_2$—C≡C—CH$_2$—O-phenyl |
| 14.124 | O—CH$_2$—C≡C—CH$_2$—O-(4-F-phenyl) |
| 14.125 | O—(CH$_2$)$_2$—SCH$_2$-phenyl |
| 14.126 | O—(CH$_2$)$_2$-SCH$_2$-(4-Cl-phenyl) |
| 14.127 | O—(CH$_2$)$_2$—N(CH$_3$)—CH$_2$-phenyl |
| 14.128 | NH$_2$ |
| 14.129 | NHCH$_3$ |
| 14.130 | NH—C$_2$H$_5$ |
| 14.131 | NH-n-C$_3$H$_7$ |
| 14.132 | NH-i-C$_3$H$_7$ |
| 14.133 | NH-n-C$_4$H$_9$ |
| 14.134 | NH-i-C$_4$H$_9$ |
| 14.135 | NH-s-C$_4$H$_9$ |
| 14.136 | NH-tert.-C$_4$H$_9$ |
| 14.137 | NH-cyclopropyl |
| 14.138 | NH-cyclobutyl |
| 14.139 | NH-cyclopentyl |
| 14.140 | NH-cyclohexyl |
| 14.141 | NH-cycloheptyl |
| 14.142 | N(CH$_3$)$_2$ |
| 14.143 | N(C$_2$H$_5$)$_2$ |
| 14.144 | NH—CH$_2$CH=CH$_2$ |
| 14.145 | NH—CH$_2$C≡CH |
| 14.146 | NH—CH$_2$—CF$_3$ |
| 14.147 | NH—CO—CH$_3$ |
| 14.148 | NH—COC$_2$H$_5$ |
| 14.149 | NH—CO—OCH$_3$ |
| 14.150 | NH—CO—OC$_2$H$_5$ |
| 14.151 | NH-CCO-tert.-C$_4$H$_9$ |
| 14.152 | N-pyrrolidinyl |
| 14.153 | N-piperdinyl |
| 14.154 | N-merpholino |
| 14.155 | N-piperazinyl |
| 14.156 | NH-phenyl |
| 14.157 | NH-(4-Cl-phenyl) |
| 14.158 | NH-(4-F-phenyl) |
| 14.159 | NH-(4-OCH$_3$-phenyl) |
| 14.160 | NH-(2,4-Cl$_2$-phenyl) |

TABLE 14-continued
| No. | $R^{14}$ |
|---|---|
| 14.161 | $CH_2-OCH_3$ |
| 14.162 | $(CH_2)_2-OCH_3$ |
TABLE 15
| No. | $R^{3'}$ |
|---|---|
| 3'.01 | $CH_3$ |
| 3'.02 | $C_2H_5$ |
| 3'.03 | $n-C_3H_7$ |
| 3'.04 | $i-C_3H_7$ |
| 3'.05 | $n-C_4H_9$ |
| 3'.06 | $i-C_4H_9$ |
| 3'.07 | $s-C_4H_9$ |
| 3'.08 | $tert.-C_4H_9$ |
| 3'.09 | $n-C_5H_{11}$ |
| 3'.10 | $i-C_5H_{11}$ |
| 3'.11 | $n-C_6H_{13}$ |
| 3'.12 | $i-C_6H_{13}$ |
| 3'.13 | $CH_2CH=CH_2$ |
| 3'.14 | $-CH(CH_3)-CH=CH_2$ |
| 3'.15 | $-CH_2-CH=CH-CH_3$ |
| 3'.16 | $-CH(CH_3)-C\equiv CH$ |
| 3'.17 | $-CH_2-C\equiv C-CH_3$ |
The following 3-phenyluracils I-1 to I-24 are particularly preferred:
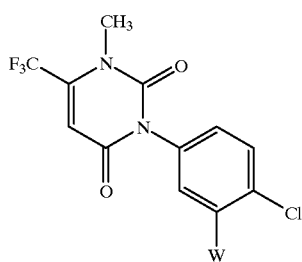
I-1
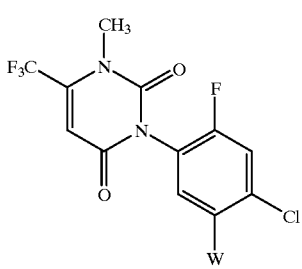
I-2
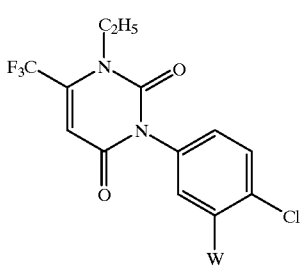
I-3
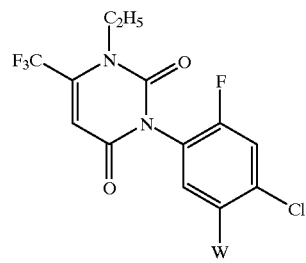
I-4
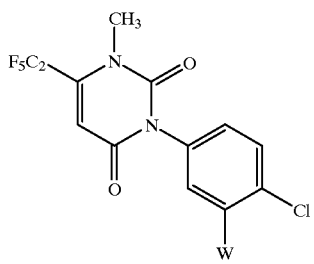
I-5
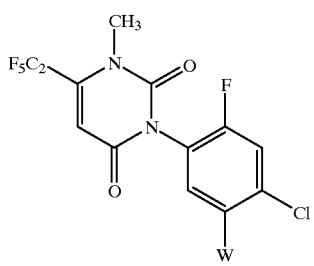
I-6
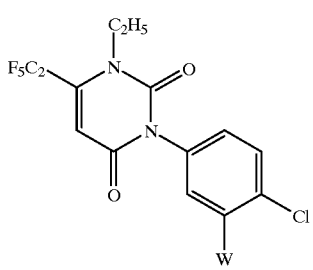
I-7
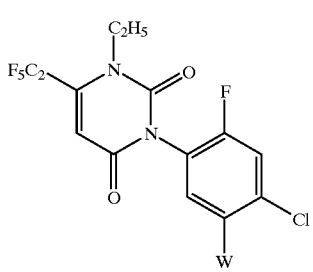
I-8
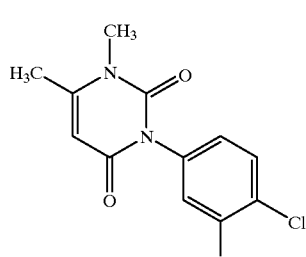
I-9

-continued
I-10
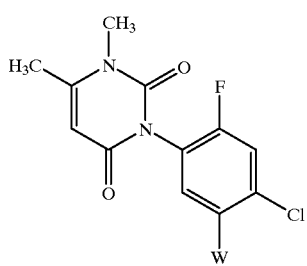
I-11
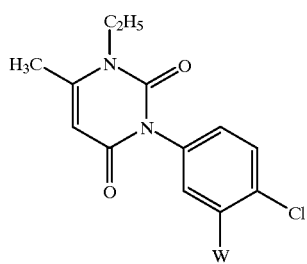
I-12
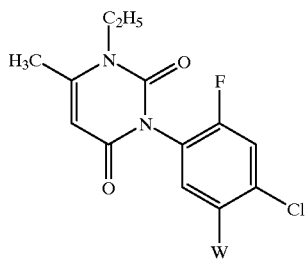
I-13
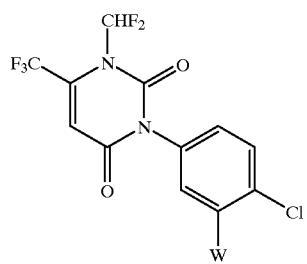
I-14
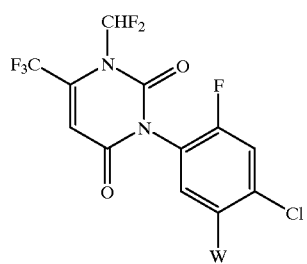
I-15
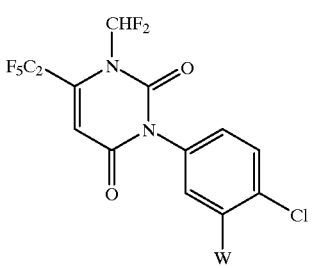
-continued
I-16
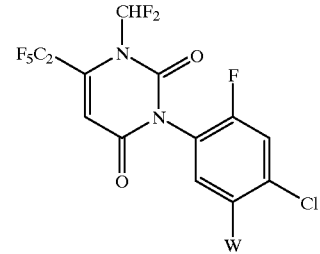
I-17
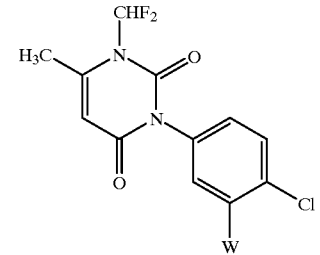
I-18
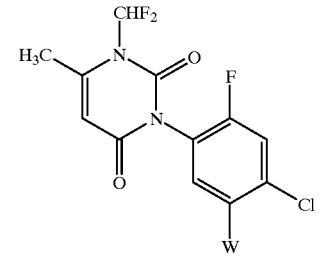
I-19
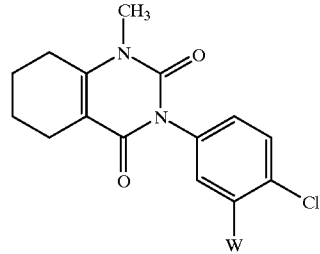
I-20
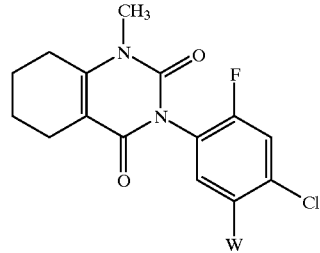
I-21
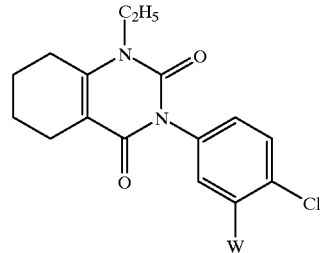

-continued

I-22

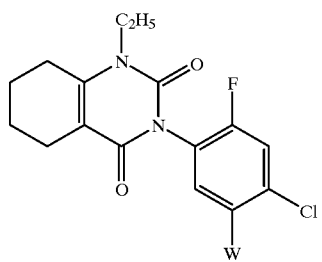

I-23

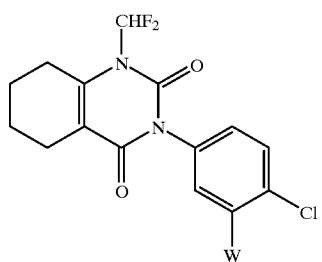

I-24

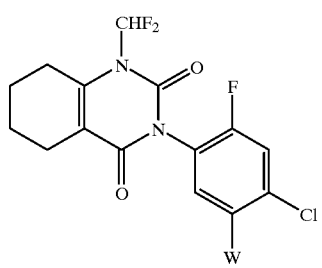

where W in each of the abovementioned formulae I-1 to I-2 has one of the following meanings:

—CHO, —COCH$_3$, —COC$_2$H$_5$, —CO-n-C$_3$H$_7$, —CO-i—C$_3$H$_7$, —CO-n-C$_4$H$_9$, —CO-i—C$_4$H$_9$, —CO-s-C$_4$H$_9$, —CO-tert.—C$_4$H$_9$, —CO—CH$_2$CH=CH$_2$, —CO—CF$_3$, —COCl$_3$, —COCH$_2$C≡CH, —CO-cyclopropyl, —CO-cyclobutyl, —CO-cyclopentyl, —CO-cyclohexyl, —CO—CN, —CO—COOCH$_3$, —CO—COOC$_2$H$_5$, —CH=NH, —CH=NCH$_3$, —CH—NC$_2$H$_5$, —CH=N-n-C$_3$H$_5$, —CH—N-i-C$_3$H$_5$, —CH=N-n-C$_4$H$_9$, —CH=NCH$_2$CH=CH$_2$, —CH=NCH$_2$CH=CH$_2$—CH$_3$, —CH=NCH$_2$C≡CH, —CH=NCH$_2$C≡C—CH$_3$, —CH=N-cyclopropyl, —CH=N-cyclobutyl, —CH=N-cyclopentyl, —CH=N-cyclohexyl, —CH=N-cycloheptyl, —CH=N—CH$_2$—CH$_2$Cl, —CH=N—CH$_2$Cl, —CH=N—C$_6$H$_5$, —CH=N-4—Br—C$_6$H$_4$, —CH=N-3—F—C$_6$H$_4$, —CH=N-4—F—C$_6$H$_4$, —CH=N-2-Cl—C$_6$H$_4$, —CH=N-3—Cl—C$_6$H$_4$, —CH=N-4—Cl—C$_6$H$_4$, —CH=N-2—Br—C$_6$H$_4$, —CH=N-2—F—C$_6$H$_4$, —CH=N-2—CH$_3$—C$_6$H$_4$, —CH=N-3—CH$_3$—C$_6$H$_4$, —CH=N-4—CH$_3$-C$_6$H$_4$, —CH=N-2—CF$_3$—C$_6$H$_4$, —CH—N-3—CF$_3$—C$_6$H$_4$, —CH=N-4—CF$_3$-C$_6$H$_4$, —CH=N-2—OCH$_3$—C$_6$H$_4$, —CH=N-3—OCH$_3$—C$_6$H$_4$, —CH=N-4—OCH$_3$—C$_6$H$_4$, —CH=N-4—NO$_2$—C$_6$H$_4$, —CH=N-4—CN-C$_6$H$_4$, —CH=N-2,4-(Cl, Cl)—C$_6$H$_4$, —CH=N-2,4—(CH$_3$,CH$_3$)—C$_6$H$_4$, —CH=N—CH$_2$OCH$_3$, —CH=N—CH$_2$OC$_2$H$_5$, —CH=N—CH$_2$CH$_2$OCH$_3$, —CH=N—CH$_2$CH$_2$OC$_2$H$_5$, —CH=N—OH, —CH=N—OCH$_3$, —CH=N—OC$_2$H$_5$, —CH=N—O-n-C$_3$H$_7$, —CH=N—O-i—C$_3$H$_7$, —CH=N—O-n-C$_4$H$_9$, —CH=N—O-i-C$_4$H$_9$, —CH=N—O-s-C$_4$H$_9$, —CH=N—O-tert.—C$_4$H$_9$, —CH=N—O—CH$_2$CH=CH$_2$, —CH=N—O—CH(CH$_3$)CH=CH$_2$, —CH=N—O—CH$_2$C≡CH, —CH=N—O—CH(CH$_3$)—C≡CH, —CH=N—O—CH$_2$—CH=CH—CH$_3$, —CH=N—O—CH$_2$—CH$_2$—Cl, —CH=N—O—CH$_2$—CH$_2$—F, —CH=N—O—CH$_2$—CF$_3$, —CH=N—O—CH$_2$—CH—CHCl, —CH=N—O—CH$_2$—CCl=CH$_2$, —CH=N—O—CH$_2$—CBr=CH$_2$, —CH=N—O—CH$_2$—C—H=Cl—CH$_3$, —CH=N—OC(O)CH$_3$, —CH=N—OC(O)C$_2$H$_5$, —CH=N—O—CH$_2$—CN, —CH=N—O—CH$_2$—CH=CH—CH$_2$—O—CH$_3$, —CH=N—O—CH$_2$—CH=CH—CH$_2$—O-tert.-C$_4$H$_9$, —CH=N—O—(CH$_2$)$_3$—C$_6$H$_5$, —CH=N—O—(CH$_2$)$_4$—C$_6$H$_5$, —CH=N—O—(CH$_2$)$_4$-4—Cl—C$_6$H$_4$, —CH=N—O—(CH$_2$)$_4$-4—OCH$_3$—C$_6$H$_4$, —CH=N—O—(CH$_2$)$_4$-4—CH$_3$—C$_6$H$_4$, —CH=N—O—(CH$_2$)$_4$-4—F—C$_6$H$_4$, —CH=N—O—CH$_2$CH=CH—C$_6$H$_5$, —CH=N—O—CH$_2$CH$_2$CH=CH-4—F—C$_6$H$_4$, —CH=N—CH$_2$CH=CH-4—Cl—C$_6$H$_4$, —CH=N—O—CH$_2$CH—CH-3—OCH$_3$—C$_6$H$_4$, —CH=N—O—(CH$_2$)$_2$CH=CH-4—F—C$_6$M$_4$, —CH=N—O—(CH$_2$)CH=CH-4—Cl—C$_5$H$_4$, —CH=N—O—CH$_2$CH=CHCH$_2$-4—OCH$_3$—C$_6$H$_4$, —CH=N—O—CH$_2$—CH=C(CH$_3$)—C$_6$H$_5$ —CH=N—O—(CH$_2$)$_2$CH=CH-3,4(Cl,Cl)-C$_6$H$_3$, —CH=N—O—(CH$_2$)$_3$C≡C-$_4$—F—C$_5$H$_4$, —CH$_2$—N—OCHOCH$_3$, —CH=N—OC$_2$H$_4$OCH$_3$, —CH=N—OCH$_2$OC$_2$H$_5$, —CH=N—OCH(CH$_3$)OCH$_3$, —CH=N—CH(CH$_3$)COOCH$_3$, —CH=N—OCH(CH$_3$)COO-n-C$_4$H$_9$, —CH=N—NH$_2$, —CH=N—NHCH$_3$, —CH=N—NHC$_2$H$_5$, —CH=N—NH-n-C$_3$H$_7$, —CH=N—NH-i-C$_3$H$_7$, —CH=N—NH-n-C$_4$H$_9$, —CH=N—NH-i-C$_4$H$_9$, —CH=N—NH—S—C$_4$H$_9$, —CH=N—NH-tert.-C$_4$H$_9$, —CH=N—NH-cyclopropyl, —CH=N—NH-cyclobutyl, —CH=N—NH-cyclopentyl, —CH=N—NH-cyclohexyl, —CH=N—NH-cycloheptyl, —CH=N—N(CH$_3$)$_2$, —CH=N—N(C$_2$H$_5$)$_2$, —CH=N—N(C$_3$H$_7$)$_3$, —CH=N—N(i-C$_3$H$_7$)(CH$_3$), —CH=N—NHCH$_2$—C≡CH, —CH=N—NHCH$_2$—C≡CH, —CH=N—N(CH$_3$)—CH$_2$—C≡CH, —CH=N—NHCH$_2$CF$_3$, —CH=N—NH—CO—CH$_3$, —CH=N—NH—CO—CH$_2$H$_5$, —CH=N—NH—COOCH$_3$, —CH=N—NH—COOC$_2$H$_5$, —CH=N—NH—COO-tert.-C$_4$H$_9$, —CH=N-pyrrolidin-1-yl, —CH=N-piperidin-1-yl, —CH=N-morpholin-4-yl, —CH=N—NH—C$_6$H$_5$, —CH=N—NH—(4—Cl—C$_6$H$_4$), —CH=N—NH—(4—NO$_2$—C$_6$H4), —CH=N—NH—(4—F—C$_6$H$_4$), —CH=N—NH—(4—CH$_3$O—C$_6$H$_4$), —CH=N—NH—(2,4—Cl$_2$—C$_6$H$_3$), —CH=N—NH—(2,4—(NO$_2$)$_2$—C$_6$H$_3$), —CH=N—NH—CO—NH$_2$, —CH=N—NH—CO—NHCH$_3$, —CH=N—NH—CO—NHC$_2$H$_5$, —CH=N—NH—CO—N(CH$_3$) 2, —CH=CH—COOH, —CH=CH—CO—OCH$_3$, —CH=CH—CO—OC$_2$H$_5$, —CH=CH—CO—O-n-C$_3$H$_7$, —CH=CH—CO—O-i—C$_3$H$_7$, —CH=CH—CO—O-n-C$_4$H$_9$, —CH=CH—CO—O-tert.—C$_4$H$_9$, —CH=CH—CO—O-cyclopropyl, —CH=CH—CO—O-cyclobutyl, —CH=CH—CO—O-cyclopentyl, —CH=CH—CO—O-cyclohexyl, —CH=CH—CO—O-cycloheptyl, —CH=C(CH$_3$)—COOH, —CH=C(CH$_3$)—CO—OCH$_3$, —CH=C(CH$_3$)—CO—OC$_2$H$_5$, —CH—C(CH$_3$)—CO—O-n-C$_3$H$_7$, —CH=C(CH$_3$)—CO—O-i-C$_3$H$_7$, —CH=C (CH₃)—CO—O-n-C₄H₉, —CH=C(CH₃)—CO--tert.-C₄H₉, —CH=C(CH₃)—CO—O-cyclopropyl, —CH=C(CH₃)—CO—O-cyclobutyl, —CH=C(CH₃)—CO—O-cyclopentyl, —CH=C(CH₃)—CO—O-cyclohexyl, —CH—C(CH₃)—CO—O-cycloheptyl. —CH=C(C₂H₅)—COOH, —CH—C(C₂H₅)—CO—OCH₃, —CH—C(C₂H₅)—CO—OC₂H₅, —CH=C(C₂H₅)—CO—O-n-C₃H₇, —CH—C(C₂H₅)—CO—O-i-C₃H₇, —CH=C(C₂H₅)—CO—O-n-C₉H₉, —CHMC(C₂H5)—CO—O-tert.-C₄H₉, —CH=C(C₂H₅)—CO—O-cyclopropyl, —CH—C(C₂H₃—CO—O-cyclobutyl, —CH=C(C₂H5)—CO—O-cyclopentyl, —CH—C(C₂H₅)—CO—O—cyclohexyl, —CH=C(C₂H₅)—CO—O-cycloheptyl, —CH—C(Cl)—COOH, —CH=C(C1)—CO—OCH₃, —CH=C(Cl)—CO—OC₂H₅, —CH=C(Cl)—CO—n-C₃H₇, —CH=C(Cl)—CO—O-i-C₃H7, —CH=C(Cl)—CO—O-n-C₄H₉, —CH=C(Cl)—CO—O-tert.-C₄H₉, —CH=C(Cl)—CO—O-cyclopropyl, —CH=C(Cl)—CO—O-cyclobutyl, —CH=C(Cl)—CO—O-cyclopentyl, —CH=C(C1)—CO—O-cyclohexyl, —CH=C(Cl)—CO—O-cycloheptyl, —CHSC(Sr)—COOH, —CH=C(Sr)—CO—OCH₃, —CH=C(Sr)—CO—OC₂H₅, —CH=C(Sr)—CO—O-n-C₃H₇, —CH—C(Sr)—CO—O-i—C₃H₇, —CH=C(Br)—CO—O-n-C₄H₉, —CH=C(sr)—CO—O-tert.—C₄H₈, —CH=C(Sr)—CO—O-cyclopropyl, —CH=C(Sr)—CO—O-cyclobutyl, —CH=C(Sr)—CO—O-cyclopentyl, —CHzC(Sr)—CO—O-cyclo hexyl, —CH=C(Sr)—CO—O-cycloheptyl, —CH—C(CN)—COOH, —CH=C(CN)—CO—OCH₃, —CH=C(CN)—CO—OC₂H₈, —CH—C(CN)—CO—O-n-C₃H₇ —CHSC(CN)—CO—O-i-C3H7, —CH=C(CN)—CO—O-n-C₄H₉, —CH—C(CN)—CO—O-tert-—C₄H₉, —CH=C(CN)—CO—O-cyclopropyl, —CH—C(CN)—CO—cyclobutyl, —CH=C(CN)—CO—O-cyclopentyl, —CH=C(CN)—CO—O-cyclohexyl, —CH=C(CN)—CO—O-cycloheptyl, —CH—CH—CO—OCH₂—OCH₃, —CH=CH—CO—OCH₂—OC₂H₅, —CH—CH—CO—OCH₂—O-n-C₃H₉, —CH=CH—CO—OCH₂—O-i—C₃HS, —CH=CH—CO—OCH(CH₃)—OCH₃, —CH=CH—CO—OCH(CH₃)—OC2H₅, —CH=CH—CO—O—CH₂CH₂—OCH₃, —CH=CH—CO—O—CH₂CH₂-OC₂H₅, —CH—C CH₃)—CO—OCH₂—OCH3, —CH=C (CH₃)—CO—OCH₂—OC₂H₅, —CH—C(CH₃)—CO—OCH₂—O-n-C₃H₅, —CH=C(CH₃)—CO—OCH₂—O-i—C3Hl, —CH—C(CH₃)—CO—OCH(CH₃)—OCH₃, —CH=C(CH₃)—CO—OCH(CH₃)—OC₂H₁, —CH—C(CH₃)—CO—O —CH₂CH₂—OCH₃, —CH=C(CH3)—CO—O—CH₂CH₂—OC₂H₅, —CHC (C₂H₈)—CO—OCH₂—OCH₃, —CH=C(C₂H₅)—CO—OCH₂—OC₂H₅, —CH=C(C₂H₈)—CO—OCH₂—O-n-C₃H₅, —CH—C(C₂Hs)—Co—oCH2-o-i—C₃H₅, —CH—C(C2H5)—CO—OCH(CH3)—OCH₃, —CH=C(C₂H₅)—CO—OCH(CH₃)—OC₂H5, —CH=C(C₂HM )—CO—O—CH₂CH₂-OCH3, —CH=C(C₂H₅)—C-oO—CH₂CH₂—OC2Hsi —CH—C(Cl)—CO—OCH₂—OCH₃, —CH=C(Cl)—CO—OCH₂—OC₂H₈, —CH=C(Cl)—CO—OCH₂-O-n-C₃H₅, —CH=C(Cl)—CO—OCH2—O-i—C₃H₅, —CH=C(Cl)—CO—OCH(CH3)—OCH₃, —CH=C(Cl)—CO—OCH(CH3)—OC₂H₅—CH=C(Cl)—CO—O—CH₂CH₂—OCH₃, —CH=C(Cl)—CO—O—CH₂CH₂—OC₂H₅, —CH=C(sr)—CO—OCH₂—OCH₃, —CH=C(Br)—CO—OCH₂—OC₂H₅, —CH=C(Sr)—CO—OCH2—O-n-C₃H₈, —CH=C(Sr)—CO—OCH₂—O-i—C₃H₅, —CH=C(8r)—CO—OCH(CH₃)—OCH3, —CH=C(Br)—CO—OCH(CH₃)—OC₂H₅, —CH—C(Br)—CO—O—CH₂CH₂—OCH₃, —CH=C Br)—CO—O—CH ₂CH₂—OC ₂Hs, —CH=C (CN)—CO—OCH₂—OCH₃, —CH=C(CN)—CO—OCH₂C₂H₅, —CH=C(CN)—CO—OCH₂—O-n-C₃H₅, —CH=C(CN)—CO—OCH₂—O-i—C₃H₅, —CH=C(CN)—CO—OCH(CH₃)—OCH₃, —CH=(CN)—Co—OCH(CH₃)—OC₂H₄, —CH—C(CN)—CO—O—CH₂CH₂—OCH₃, —CH=C(CN)—CO—O—CH₂CH₂—OC₂HS, —CH—CH—CO—OCH₂—CF₃, —CH=CH—CO—OCH₂—C13, —CH=CH—CO—OCH₂-oxiranyl, —CH=CH—CO—O(CH₂)₃-Br, —CH—CH—CO—OCH₂—CH=CH₂, —CH=CH—CO—OCH₂—C—CH. —CH=CH—CO—OCH₂—CN, —CH—CH—CO—O(CH₂)₂-CN, —CH—C(CH₃)—CO—OCH₂—CF₃, —CH—C(CH₃)—CO—OCH₂—C13, —CH—C(CH₃)—CO—OCH₂-oxiranyl, —CH=C(CH₃)—CO—O(CH₂)₃-Br, —CH—C(CH₃)—CO—OCH₂—CH=CH₂, —CH=C(CH₃)—CO—OCH₂—C=CH, —CH=C(CH₃)—CO—OCH₂—CN, —CH=C(CH₃)—CO—O(CH₂)₂—CN, —CHzC(C₂H₅)—CO—OCH₂—CF₃, —CH=C(C₂H₅)—CO—OCH₂—Cl₃, —CH—C(C₂H₃)—CO—OCH₂-oxiranyl, —CH=C(C2H₅)—CO—O(CH₂)₃-Br, —CH—C(C₂H₅)—CO—OCH₂—CH—CH₂, —CH=C(C₂H₅)—CO—OCH₂—C=—CH, —CH—C(C₂H₅)—CO—OCH₂—CN, —CH=C(C₂H₅)—CO—O(CH₂)₂—CN, —CHuC(Cl)—CO—OCH₂—CF₃, —CH=C(Cl)—CO—OCH₂—Cl₃, —CH=C(Cl)—CO—OCH₂-oxiranyl, —CH=C(Cl)—CO—O(CH₂)₃-Br, —CH=C(Cl)—CO—OCH₂—CH=CH₂, —CH=C(Cl)—CO—OCH₂—C=CH, —CH=C(Cl )—CO—OCH₂—CN, —CH=C(Cll)—CO—O(CH₂)₂—CN, —CH=C(Br)—CO—OCH₂—CF₃, —CH=C(Br)—CO—OCH₂—Cl₃, —CH=C(Br)—CO—OCH₂-oxiranyl, —CH=C(Br)—CO—O(CH₂)₃-Br, —CH=C(Sr)—CO—OCH₂—CH=CH₂, —CH=C(Br)—CO—OCH₂—C—CH, —CH—C(Br)—CO—OCH₂—CN, —CH=C(SBr)—CO—O(CH₂)₂—CN, —CH—C(CN)—CO—OCH₂—CF₃, —CH=C(CN)—CO—OCH₂—Cl₃, —CH=C(CN)—CO—OCH₂-oxiranyl, —CH=C(CN)—CO—O(CH₂)₃-Br, —CH=C(CN)—CO—OCH₂—CH—CH₂, —CH=C(CN)—CO—OCH₂—C=CH, —CH=C(CN)—CO—OCH₂—CN, —CH=C(CN)—CO—O(CH₂)₂—CN, —CH=CH—CO—CH₃, —CH=CH—CO—C₂HS, —CH=CH—CO-n-C-₃H₇, —CH=CH—CO—i—C₃H₇, —CH=CH—CO-n-C₄H₉, —CH=CH—CO—tert-—C₄H₉, —CH=CH—CO—CH₂CI, —CH—CH—CO—CH₂Br, —CH=CH—CO—CHCl₂, —CH=CH—CO—CH₂—OCH₃, —CH—CH—CO—CH(OCH₃)2, —CH=CH—CO—CH₂—SCH₃, —CH=C(CH₃)—CO—CH₃, —CH=C(CH₃)—CO—C₂HS, —CH=C(CH₃)—CO-n-C₃H₇, —CH=C(CH₃)—CO—i—C₃H₇ —CH=C(CH₃)—CO-n-C₄H₉, —CH=C(CH₃)—CO—tert.—C₄H₉, —CH=C(CH₃)—CO—CH₂Cl, —CH=C(CH₃)—CO—CH₂Br, —CH=C(CH₃) —CO—CHCl₂, —CH=(CH₃)—CO—CH₂—OCH₃, —CH=C(CH₃)—CO—CH(OCH₃)2, —CH=C(CH₃)—CO—CH₂—SCH₃, —CH=C(C₂H₅)—CO—CH₃, —CH=C(C₂H₅)—CO—C₂H₅, CH—C(C₂H₅)—CO-n-C₃H₇, —CH=C (C₂HS)—CO—i—C₃H₇, —CH=C(C₂H₃)—CO-n-C₄H₉, —CH=C(C₂HS)—CO—tert-—C₄H₉, —CH=C(C₂H₅)—CO—CH₂Cl, —CH=C(C₂H₅)—CO—CH₂Br, —CH—C(C₂, H₅)—CO—CHCl₂, —CH=C(C₂H₅)—CO—CH₂—OCH₃, —CH—C(C₂H₅)—CO—CM(OCM₃)₂, —CH=C(C2H₅)—CO—CH₂—SCH₃, —CH—C(Cl)—CO—CH₃, —CH=C(Cl)—CO—C₂H₅, —CH=C(Cl)—CO-n-C₃H₇, —CH=C(Cl)—CO—i—C₃H₇, —CH—C(Cl)—CO-n-C₂H₉, —CH=C(Cl)—CO—tert.—C4H₉, —CH—C(Cl)—CO—CH₂Cl, —CH=C(Cl)—CO—CH₂Br, —CH=C(Cl)—CO—CHC12, —CH—C(Cl)—CO—CH₂—OCH₃, —CH=C(Cl)—CO—CH(OCH₃)2, —CH=C(Cl)—CO—CH₂—SCH₃, —CH=C(Br)—CO—CH₃, —CH=C(Br)—CO—C₂H₅, —CH=C(Br)—CO-n-C₃H₇, —CHC(Sr)—CO—i—C₃H₇, —CH=C(Br)—CO-n-C₄H₉, —CH—C(Br)—CO—tert.—C₄H₉, —CH—C(Sr)—CO—CH₂Cl, —CH=C(Br)—CO—CH₂Br, —CH—C(Br)—CO—CHCl2, —CH=C(8r)—CO—CH₂—OCH₃, —CH=C(Br)—CO—CH(OCH₃)2, —CH—C(Br)—CO—CH₂—SCH₃, —CH=C(CN)—CO—CH₃, —CH=C(CN)—CO—C₂H₅, —CH=C(CN)—CO-n-C₃H₇, —CH=C(CN)—CO—i—C₃H₇, —CH=C(CN)—CO-n-C₄H₉, —CH=C(CN)—CO—tert.—C₄H₉, —CH—C(CN)—CO—CH₂Cl, —CH=C(CN)—CO—CH₂Br, —CH=C(CN)—CO—CHCl₂, —CH₃C(CN)—CO—CH₂—OCH₃, —CH=C(CN)—CO—CH(OCH₃)2, —CH=C(CN)—CO—CH₂—SCH₃, —CH=CH—CO—C₆H₅, —CH=CH—CO—(4—Cl—C₆H₄), —CHUC(CH₃)—CO—C₆H₅, —CH=C(CH₃)—Co-(4—Cl—C₆H₄), —CH=C(C₂H₅)—CO—C₆H₅, —CH=C(C₂H₅)—CO—(4—Cl—C₆H₄), —CH=C(Cl)—CO—C₆H₅, —CH=C(Br)—CO—C5H , —CH=C(CN)—CO—C6HS —CH—CH—CO—NH₂, —CH—CH—CO—NHCH₃, —CH=CH—CO—N(CH₃) 2, —CH=CH—CO—NH—C₂H₅, —CH=CH—CO—N(C₂H₅) 2, —CH=CH—CO—NH-n-C₃H₇, —CH=CH—CO—NH-i—C₃H₇, —CH=CH—CO—NH-tert-—C₄H₉, —CH=CH—CO—NH-cyclopropyl, —CH=CH—CO—NH-cyclobutyl, —CH—CH—CO—NH-cyclopentyl, —CH=CH—CO—NH-cyclohexyl, —CH=CH—CO—NH-cycloheptyl, —CH=CH—CO—NH-cyclooctyl, —CH=CH—CO—pyrrolidin-1-yl, —CH=CH—CO—piperidin-1-yl, —CH—CH—CO—morpholin-4-yl, —CH=CH—CO—NH—CH₂CH—CH₂, —CH—CH—CO—NH—CH₂CBCH, —CH=CH—CO—N(CH₃)—CH₂CH, —CH=CH—CO—NH—( CH₂) ₂Cl, —CH=CH—CO—NH—C6HS, —CH=C(CH₃)—CO—NH₂, —CH—C(CH₃)—CO—NHCH₃, —CH=C(CH₃)—CO—N(CH₃)2, —CH—C(CH₃)—CO—NH—C₂HS, —CH=C(CH₃)—C-N(C2H₅)², —CH=C(CH₃)—CO—NH-n-C₃H₇, —CH=C(CH₃)—CO—NH-i-C₃H₇, —CH—C(CH₃)—CO—NH-tert.—C4H₉, —CH=C(CH₃)—CO—NH-cyclopropyl, —CH—C(CH₃)—CO—NH—cytlobutyl, —CH=C(CH₃)—CO—NH-cyclopentyl, —CH=C(CH₃)—CO—NH-cyclohexyl, —CH=C(CH₃)—CO—NH-cycloheptyl, —CH=C(CH₃) —CO—NH—cyclooctyl, —CH=C(CH₃)—CO—pyrrolidin-l-yl, —CHaC(CH₃)—CO-piperidin-1-yl, —CH=C(CH₃)—CO—morpholin-4-yl, —CHC(CH₃)3—Co-NH—CH₂CH=C(CH 3)², —CH=C(CH₃)—CO—NH—CH₂C—CH, —CH—C(CH₃)—CO—N(CH₃)—CH₂C=CH, —CH=C(CH₃)—CO—NH—(CH₂)₂Cl, —CH=C(CH₃)—CO—NH—C₆H₉, —CH=C(C₂HS)—CO—NH₂, —CH—C(C₂H₅)—CO—NHCH₃, —CH—C(C₂H₉)—CO—N(CH₃), —CH=C(C₂H₅)—CO—NN—C2HS, —CH—C(C₂H₅)—CO—N(C₂H₅)₂, —CH=C(C₂HS)—CO—NH-n-C₃H₇, —CH=C(C₂H₅)—CO—NH-i—C₃H₇, —CH=C(C₂H₅)—CO—NH-tert.—C4H₉, —CH=C(C₂H₅)—CO—NH—cyclopropyl, —CH=C(C₂H₅)—CO—NH-cyclobutyl, —CH=C(C₂H₅)—CO—NH-cyclopentyl, —CH=C(C₂H₅)—CO—NH-cyclohexyl, —CH=C(C₂H₅)—CO—NH-cycloheptyl, —CH=C(C₂H₅)—CO—NH-cyclooctyl, —CH=C(C₂HS)—CO—pyrrolidin-1-yl, —CH=C(C₂H₅)—CO—piperidin-1-yl, —CH—C(C₂H₅)—CO—morpholin-4-yl, —CH=C(C₂H₅)—CO—NH—CH₂CH—C(C₂H₅)2, —CH=C(C₂H₅)—CO—NH—CH₂C=CH, —CH=C(C₂H₅)—CO—N(CH₃)—CH₂C=—CH, —CH—C(C₂H₅)—CO—NH—(CH₂)₂Cl, —CH=C(C₂H₅)—CO—NH—C₆H₅, —CH—C(Cl)—CO—NH₂, —CH=C(Cl)—CO—NHCH₃, —CH=C(Cl)—CO—N(CH₃)₂, —CH—C(Cl)—CO—NH—C2H₅, —CH=C(Cl)—CO—N (C₂H₅)₂, —CH—C(Cl)—CO—NH-n-C₃H₇, —CH=C(Cl)—CO—NH-i—C₃H₇, —CH=C(Cl)—CO—NH-tert.—C₄H₉, —CH=C(Cl)—CO—NH-cyclopropyl, —CH=C(Cl)—CO—NH-cyclobutyl, —CH=C(Cl)—CO—NH-cyclopentyl, —CH—C(Cl)—CO—NH-cyclohexyl, —CH=C(Cl)—CO—NH-cycloheptyl, —CH—C(Cl )—CO—NH-cyclooctyl, —CH=C(Cl)—CO—pyrrolidin-1-yl, —CH—C(Cl)—CO—piperidin-1-yl, —CH=C(Cl)—CO—morpholin-4-yl, —CH—C(Cl)—CO—NH—CH₂CH=C(Cl)₂, —CH=C(Cl)—CO—NH—CH₂C=CH, —CH—C(Cl)—CO—N(CH₃)—CH₂C=CH, —CH=C(Cl)—CO—NH—(CH₂)₂Cl, —CH=C(Cl)—CO—NH—C₆H₅, —CH=C(Sr)—CO—NH₂, —CH=C(Br)—CO—NHCH₃, —CH—C(Br)—CO—N(CH₃) 2, —CH—C (Br)—CO—NH—C₂H₉, —CH=C(Br)—CO—N(C₂H₅)2, —CH=C(Br)—CO—NN-n-C₃H₇, —CH=C(Br)—CO—NH-i—C₃H₇, —CH—C(Br)—CO—NH-tert.—C₄H₉, —CH=C(Br)—CO—NH-cyclopropyl, —CH—C(Br)—CO—NH-cyclobutyl, —CH=C(Br)—CO—NH-cyclopentyl, —CH—C(Br)—CO—NH-cyclohexyl, —CH=C(Br)—CO—NH-cycloheptyl, —CH—C(Br)—CO—NH-cyclooctyl, —CH=C(Br)—CO—pyrrolidin-1-yl, —CH=C(Br)—CO—piperidin-1-yl, —CH=C(Br)—CO—morpholin-4-yl, —CH=C(Br)—CO—NH—CH₂CH=C(Br)₂, —CH=C(Br)—CO—NH—CH₂C=—CH, —CH=C(Sr)—CO—N(CH₃)—CH₂C=CH, —CH=C(Br)—CO—NH—(CH₂)₂Cl, —CH—C(9r)—CO—NH—C₆H₅, —CH=C(CN)—CO—NH₂, —CH=C(CN)—CO—NHCH₃, —CH=C(CN)—CO—N(CH₃)2, —CH=C(CN)—CO—NH—C2H₅, —CH=C(CN)—CO—N(C₂H₅)2, —CH—C( CN)—CO—NH-n-C₃H₇, —CH=C(CN)—CO—NH-i—C3H₇, —CH—C(CN)—CO—NH-tert.—C4H₉, —CH=C(CN)—CO—NH-cyclopropyl, —CH—C(CN)—CO—NH-cyclobutyl, —CH=C(CN)—CO—NH-cyclopentyl, —CH—C(CN)—CO—NH-cyclohexyl, —CH=C(CN)—CO—NH-cycloheptyl, —CH=C(CN)—CO—NH—cyclooctyl, —CH=C(CN)—CO—pyrrolidin-1-yl, —CH—C(CN)—CO—piperidin-1-yl, —CH=C(CN)—CO—morpholin-4-yl, —CHUC( CN)—CO—NH—CH₂CHzC(CN)2, —CH=C(CN)—CO—NH—CH₂C-=CH, —CH—C CN)—CO—N(CH₃)—CH₂MH, —CH=C(CN)—CO—NH—(CH₂)₂Cl, —CH=C(CN)—CO—NN—C$_6$H$_5$, —CH=CH—CO—SCH$_3$, —CH=CH—CO—SC$_2$H$_5$, —CH—CH—CO—S-n-C$_3$H$_7$, —CH—CH—CO—S-i—C3M7, —CH=CH—CO—S-n-C$_4$H$_9$, —CH—CH—CO—S-tert.—C$_4$HS, —CH=C(CH$_3$)—CO—SCH$_3$, —CH=C(CH$_3$)—CO—SC$_2$H$_{51}$ —CH—C(CH$_3$)—CO—S-n-C3H$_7$, —CH=C(CH$_3$)—CO—S-i—C$_3$H$_7$, —CH=C(CH$_3$)—CO—S-n-C$_4$H$_9$, —CH=C(CH$_3$)—CO—S-tert.—C$_4$H$_9$, —CH—C(C$_2$HS)—CO—SCH$_3$, —CH=C(C$_2$H$_5$)—CO—SC$_2$H$_5$, —CH=C(C$_2$MS)—CO—S-n-C$_3$H$_7$, —CH=C(C2H$_5$)—CO—S-i—C$_3$H$_7$, —CH*C(C$_2$H$_5$)—CO—S-n-C4H$_9$, —CH=C(C$_2$HS)—CO—S-tert.—C$_4$HS, —CH=C(Cl)—CO—SCH$_3$, —CH=C(C(C$_1$ )—CO—SC 2H$_4$, —CH—C(Cl)—CO—S-n-C$_3$H$_7$, —CH—C(Cl)—CO—S-i—C$_3$H$_7$, —CH=C(Cl)—CO—S-n-C$_4$H$_9$, —CH=C(Cl)—CO—S-tert.—C$_4$H$_9$, —CH=C(Br)—CO—SCH$_3$, —CH=C(Sr)—CO—SC$_2$H$_5$, —CH=C(Sr)—CO—S-n-C$_3$H$_7$, —CH=C(Br)—CO—S-i—C$_3$H$_7$, —CH—C(ar)—CO—S-n-C$_4$H$_9$, —CH=C(Sr)—CO—S-tert.—C$_4$H$_9$, —CH=C(CN)—CO—SCH$_3$, —CH—C(CN)—CO—SC$_2$H$_5$, —CH=C(CN)—CO—S-n-C$_3$H$_7$, —CH—C(CN)—CO—S-i—C$_3$H$_7$, —CH=C(CN)—CO—S-n-C$_4$H$_9$, —CH—C(CN)—CO—S-tert-—C$_4$H$_9$, —CH=C(COCN$_3$)—CO—OCH$_3$, —CHSC(COC$_2$H$_5$)—CO—OCH$_3$, —CH=Cl CO-n-C$_3$H$_7$)—CO—OCH$_3$, —CH—C( COCH$_3$)—CO—OC$_2$H$_5$, —CH=C(COC$_2$H$_5$)—CO—OC$_2$HS, —CH—C(CO-n-C$_3$H$_7$)—CO—OCZH$_5$, —CH=C(COCH3)—CO—O-n-C $_3$H$_7$, —CH=C(COC2H$_5$)—CO—O-n-C$_3$H$_7$, —CH—C(CO-n-C$_3$H$_7$)—CO—O-n-C$_3$H$_7$, —CH—C(CF$_3$)—CO—OCH$_3$, —CH=C(CF$_3$)—CO—OC$_2$H$_5$, —CH—C(CF$_3$)—CO—O-n-C$_3$H$_7$, —CH=C(CF$_3$)—CO—O-i—C$_3$H$_7$, —CH=C(CF$_3$)—CO—O-n-C$_4$H$_9$, —CH=C(CF$_3$)—CO—O-tert.—C$_4$H$_9$, —CH—C(COOCH$_3$)2, —CH—C(COOC$_2$H$_5$)2, —CH=C(COOCH$_3$)—CO—OC$_2$H$_5$, —CH—C(COO-n-C 3H$_7$)—CO—OCH$_3$, —CH=C(COO-n-C3H$_7$)—CO—OC$_2$H$_5$, —CH=C(COO-n-C 3H$_8$) 2, —CH=CH—CH=CH—COOH, —CH=CH—CH=CH—CO—OCH$_3$, —CH=CH—CH=CH—CO—OC$_2$H$_5$, —CH=CH—CH=C(COOCH$_3$)2, —CH—CH—CH=C(CN)—CO—OCH$_3$, —CH=CH—CH—C(CN)—CO—OC 2HS, —CH=C(CH$_3$)—CH=C(CN)—CO—OCH$_3$, —CH=CtCH$_3$)—CH=C(CN)—CO—OC$_2$H$_5$, —CHUC(CH$_3$)—CH=C(CH$_3$)—CO—OCH$_3$, —CH=C(CH$_3$)—CH—C(Cl)—CO—OCH$_3$, —CH—C(CH$_3$)—CH=C(Br)—CO—OCH$_3$, —CH=C(CH$_3$)—CH—C(CH$_3$)—CO—OC$_2$H$_5$, —CH—C(CH$_3$)—CH—C(Cl)—CO—OC$_2$H$_5$, —CH=C(CH$_3$)—CHuC(Br)—CO—OC$_2$H$_5$, —CH=C(CH$_3$)—CHuC(CN)—CO—NH$_2$, —CH=C(CH$_3$)—CH—C(CN)—CO—NH—CH$_3$, —CH=CH—(CH$_2$)$_2$—COOH, —CH=CH—(CH$_2$)$_2$—CO—OCH$_3$, —CH—CH—(CH$_2$)$_2$—CO—OC$_2$H$_5$, —CH=CH—CH$_2$—CH(COOCH 3)2, —CH=CH—CH$_2$—CH(COOC$_2$H$_5$)2, —CH=CH—CH$_2$—CH(CN)—CO—OCH$_3$, —CH—CH—CH$_2$—CH(CN)—CO—OC$_2$H$_5$, —CH=CH—CH $_2$—CH(CH$_3$)—CO—OCH$_3$, —CH—CH—CH$_2$—CH(CH$_3$)—CO—OC$_2$H$_5$, —CH=CH-(CH$_2$)$_2$—CO—NH$_2$, —CH—CH-(CH$_2$)$_2$—CO—NH—CH$_3$, —CH=CH—CH$_2$—COOH, —CH=CH—CH$_2$—CO—OCH$_3$, —CH=CH—CH $_2$—CO—OC$_2$H$_5$, —CH=C(COOCH$_3$)—CH $_2$—CO—OCH$_3$, —CHuC(COOCH$_3$)—CH $_2$—CO—OC$_2$H$_5$, CH=CH—CH$_2$—CO—NH$_2$, —CH=CH—CH$_2$—CO—NH—CH$_3$, —CH=CH—CH$_2$—CO—N (CH $_3$) 2, —CH(OCH$_3$)$_2$, —CH(SCH$_3$)$_2$, —CH(OC$_2$H$_5$)$_2$, —CH(SC$_2$H$_5$)$_2$, —CH(O-n-C$_3$H$_7$)$_2$, —CH(O-i-C$_3$H$_7$)$_2$, —CH(s-n-C$_3$H$_7$)$_2$, —CH(S-i—C$_3$h$_7$)$_2$, —CH(O-n-C$_4$H$_9$)$_2$, —CH(O-i—C$_4$H$_9$)$_2$, —CH(O-s—C$_4$H$_9$)$_2$, —CH(O-tert.—C$_4$H$_9$)$_2$, —CH(S-n-C$_4$H$_9$)$_2$, —CH(S-i—C$_4$H$_9$)$_2$, —CH(S-S—C$_4$H$_9$)$_2$, —CH(S-tert.—C$_4$H$_9$)$_2$, —CH(OC$_5$HM$_1$)$_2$, 1,3-dioxolan-2-yl, 1,3-dithiolan-2-yl, 1,3-oxathiolan-2-yl, 4-methyl-1,3-dioxolan-2-yl, 4-methyl-1,3-dithiolan-2-yl, 4-methyl-1,3-oxathiolan-2-yl, 5-methyl-1,3-oxathiolan-2-yl, 4-ethyl-1,3-dioxolan-2-yl, 4-ethyl-1,4-dithiolan-2-yl, 4-ethyl-1,3-oxathiolan-2-yl, 5-ethyl-1,3-oxathiolan-2-yl, 4,5-dimethyl-1,3-dioxolan-2-yl, 4,4-dimethyl-1,3-dioxolan-2-yl, 4,5-dimethyl-1,3-dithiolan-2-yl, 5,5-dimethyl-1,3-dithiolan-2-yl, 4,5-dimethyl-1,3-oxathiolan-2-yl, 5,5-dimethyl-1,3-oxathiolan-2-yl, 4,4-dimethyl-1,3-oxathiolan-2-yl, 4-vinyl-1,3-dioxolan-2-yl, 4-vinyl-1,3-dithiolan-2-yl, 4-vinyl-1,3-oxathiolan-2-yl, 5-vinyl-1,3-oxathiolan-2-yl, 4-chloromethyl-1,3-dioxolan-2-yl, 4-chloromethyl-1,3-dithiolan-2-yl, 4-chloromethyl-1,3-oxathiolan-2-yl, 5-chloromethyl-1,3-oxathiolan-2-yl, 4-hydroxymethyl-1,3-dioxolan-2-yl, 4-hydroxymethyl-1,3-dithiolan-2-yl, 4-hydroxymethyl-1,3-oxathiolan-2-yl, 5-hydroxymethyl-1,3-oxathiolan-2-yl, 4-methoxymethyl-1,3-dioxolan-2-yl, 4-allyloxymethyl-1,3-dioxolan-2-yl, 4-propargyloxymethyl-1,3-dioxolan-2-yl, 4-acetoxymethyl-1,3-dioxolan-2-yl, 4-methoxymethyl-1,3-dithiolan-2-yl, 4-allyloxymethyl-1,3-dithiolan-2-yl, 4-propargyloxymethyl-1,3-dithiolan-2-yl, 4-acetoxymethyl-1,3-dithiolan-2-yl, 4-methylthiomethyl-1,3-dithiolan-2-yl, 4-methoxymethyl-1,3-oxathiolan-2-yl, 5-methoxymethyl-1,3-oxathiolan-2-yl, 4-allyloxymethyl-1,3-oxathiolan-2-yl, 5-allyloxymethyl-1,3-oxathiolan-2-yl, 4-propargyloxymethyl-1,3-oxathiolan-2-yl, 5-propargyloxymethyl-1,3-oxathiolan-2-yl, 4-acetoxymethyl-1,3-oxathiolan-2-yl, 5-acetoxymethyl-1,3-oxathiolan-2-yl, 4-methylthiomethyl-1,3-dioxolan-2-yl, 4-carboxy-1,3-dithiolan-2-yl, 4-methoxycarbonyl-1,3-dioxolan-2-yl, 4-ethoxycarbonyl-1,3-dioxolan-2-yl, 4-n-butoxycarbonyl-1,3-dioxolan-2-yl, 4-methoxycarbonyl-1,3-dithiolan- 2-yl, 4-ethoxycarbonyl-1,3-dithiolan-2-yl, 4-n-butoxycarbonyl-1,3-dithiolan-2-yl, 4-methoxycarbonyl-4-methyl-1,3-dioxolan-2-yl, 4-methoxycarbonyl-4-methyl-1,3-dithiolan-2-yl, 4-ethoxycarbonyl-4-methyl-1,3-dioxolan-2-yl, 4-ethoxycarbonyl-4-methyl-1,3-dithiolan-2-yl, 4-n-butoxycarbonyl-4-methyl-1,3-dioxolan-2-yl, 4-n-butoxycarbonyl-4-methyl-1,3-dithiolan-2-yl, 4-cyanomethyl-1,3-dioxolan-2-yl, 4-cyanomethyl-1,3-dithiolan-2-yl, 1,3-dioxan-2-yl, 1,3-dithian-2-yl, 1,3-oxathian-2-yl, 5-methyl-1,3-dioxan-2-yl, 5-methyl-1,3-dithian-2-yl, 5-methyl-1,3-oxathian-2-yl, 5,5-dimethyl-1,3-dioxan-2-yl, 4,6-dimethyl-1,3-dioxan-2-yl, 4,4-dimethyl-1, 3-dioxan-2-yl, 5,5-dimethyl-1,3-dithian-2-yl, 4,6-dimethyl-1,3-dithian-2-yl, 4,4-dimethyl-1,3-dithian-2-yl, 5,5-dimethyl-1,3-oxathian-2-yl, 4,4-dimethyl-1,3-oxathian-2-yl, 6,6-dimethyl-1,3-oxathian-2-yl, 4-hydroxy-methyl-1,3-dioxan-2-yl, 4-methoxymethyl-1,3-dioxan-2-yl, 4-allyloxymethyl-1,3-dioxan-2-yl, 4-acetoxymethyl-1,3-dioxan-2-yl, 4-hydroxymethyl-1,3-dithian-2-yl, 4-methoxy-methyl-1,3-dithian-2-yl, 4-allyloxymethyl-1,3-dithian-2-yl, 4-acetoxymethyl-1,3-dithian-2-yl, 4-chloromethyl-1,3-dioxan-2-yl, 4-chloromethyl-1,3-dithian-2-yl, 1,3-dioxepan-2-yl, 1,3-dithiepan-2-yl, 1,3-dioxep-5-en-2-yl, 4-methoxycarbonyl-1,3-dioxan-2-yl, 4-ethoxycarbonyl-1,3-dioxan-2-yl, 4-n-butoxycarbonyl-1,3-dioxan-2-yl, 4-methoxycarbonyl-1,3-dithian-2-yl, 4-ethoxycarbonyl-1,3-dithian-2-yl, 4-n-butoxycarbonyl-1,3-dithian-2-yl, 4-methoxycarbonyl-4-methyl-1,3-dioxan-2-yl, 4-ethoxy-carbonyl-4-methyl-1,3-dioxan-2-yl, 4-n-butoxycarbonyl-4-methyl-1,3-dioxan-2-yl, 4-methoxycarbonyl-4-methyl-1,3-dithian-2-yl, 4-ethoxycarbonyl-4-methyl-1,3-dithian-2-yl, 4-n-butoxycarbonyl-4-methyl-1,3-dithian-2-yl, —$C(CH_3)(OCH_3)_2$, —$C(CH_3)(SCH_3)_2$, —$C(CH_3)(OC_2H_5)_2$, —$C(CH_3)(SC_2H_5)_2$, —$C(CH_3)(O-n-C_3H_7)_2$, —$C(CH_3)(O-i-C_3H_7)_2$, —$C(CH_3)(S-n-C_3H_7)_2$, —$C(CH_3)(S-i-C_3H_7)_2$, —$C(CH_3)(O-C_4H_9)_2$, —$C(CH_3)(O-i-C_4H_9)_2$, —$C(CH_3)(O-S-C_4M_9)_2$, —$C(CH_3)(O-tert.-C_4H_9)_2$ —$C(CH_3)(S-n-C_4H_9)_2$, —$C(CH_3)(S-i-C_4H_9)_2$, —$CH_3(s-S-C_4H_9)_2$, —$C(CH_3)(S-tert.-C_4H_9)_2$, —$C(CH_3)(O-n-C_5H_{11})$, —$C(CH_3)$ $(O-n-C_5H_{11})_2$, 2-methyl-1,3-dioxolan-2-yl, 2-methyl-1,3-dithiolan-2-yl, 2-methyl-1,3-oxathiolan-2-yl, 2,4-dimethyl-1,3-dioxolan-2-yl, 2,4-dimethyl-1,3-dithiolan-2-yl, 2,4-dimethyl-1,3-oxathiolan-2-yl, 2,5-dimethyl-1,3-oxathiolan-2-yl, 4-ethyl-2-methyl-1,3-dioxolan-2-yl, 4-ethyl-2-methyl-1,3-dithiolan-2-yl, 4-ethyl-2-methyl-1,3-oxathiolan-2-yl, 5-ethyl-2-methyl-1,3-oxathiolan-2-yl, 2,4,5-trimethyl-1,3-dioxolan-2-yl, 2,4,4-trimethyl-1,3-dioxolan-2-yl, 2,4,5-trimethyl-1,3-dithiolan-2-yl, 2,4,4-trimethyl-1,3-dithiolan-2-yl, 2,4,5-trimethyl-1,3-oxathiolan-2-yl, 2,4,4-trimethyl-1,3-oxathiolan-2-yl, 2-methyl-4-vinyl-1,3-dioxolan-2-yl, 2-methyl-4-vinyl-1,3-dithiolan-2-yl, 2-methyl-4-vinyl-1,3-oxathiolan-2-yl, 2-methyl-5-vinyl-1,3-oxathiolan-2-yl, 4-chloromethyl-2-methyl-1,3-dioxolan-2-yl, 4-chloromethyl-2-methyl-1,3-dithiolan-2-yl, 4-chloromethyl-2-methyl-1,3-oxathiolan-2-yl, 5-chloromethyl-2-methyl-1,3-oxathiolan-2-yl, 4-hydroxymethyl-2-methyl-1,3-dioxolan-2-yl, 4-hydroxymethyl-2-methyl-1,3-dithiolan-2-yl, 4-hydroxymethyl-2-methyl-1,3-oxathiolan-2-yl, 5-hydroxymethyl-2-methyl-1,3-oxathiolan-2-yl, 4-methoxymethyl-2-methyl-1,3-dioxolan-2-yl, 4-allyloxymethyl-2-methyl-1,3-dioxolan-2-yl, 2-methyl-4-propargyloxymethyl-1,3-dioxolan-2-yl, 4-acetoxy-2-methyl-1,3-dioxolan-2-yl, 4-methoxymethyl-2-methyl-1,3-dithiolan-2-yl, 4-allyloxymethyl-2-methyl-1,3-dithiolan-2-yl, 2-methyl-4-propargyloxymethyl-1,3-dithiolan-2-yl, 4-acetoxy-2-methyl-1,3-dithiolan-2-yl, 4-methoxymethyl-2-methyl-1,3-oxathiolan-2-yl, 5-methoxymethyl-2-methyl-1,3-oxathiolan-2-yl, 4-allyloxymethyl-2-methyl-1,3-oxathiolan-2-yl, 5-allyloxymethyl-2-methyl-1,3-oxathiolan-2-yl, 2-methyl-4-propargyloxymethyl-1,3-oxathiolan-2-yl, 2-methyl-5-propargyloxymethyl-1,3-oxathiolan-2-yl, 4-acetoxy-2-methyl-1,3-oxathiolan-2-yl, 5-acetoxy-2-methyl-1,3-oxathiolan-2-yl, 2-methyl-4-methylthiomethyl-1,3-dioxolan-2-yl, 2-methyl-4-methylthiomethyl-1,3-dithiolan-2-yl, 4-carboxy-2-methyl-1,3-dioxolan-2-yl, 4-carboxy-2-methyl-1,3-dithiolan-2-yl, 4-methoxycarbonyl-2-methyl-1,3-dioxolan-2-yl, 4-ethoxycarbonyl-2-methyl-1,3-dioxolan-2-yl, 4-n-butoxycarbonyl-2-methyl-1,3-dioxolan-2-yl, 4-methoxycarbonyl-2-methyl-1,3-dithiolan-2-yl, 4-ethoxycarbonyl-2-methyl-1,3-dithiolan-2-yl, 4-n-butoxycarbonyl-2-methyl-1,3-dithiolan-2-yl, 2,4-dimethyl-4-methoxycarbonyl-1,3-dioxolan-2-yl, 2,4-dimethyl-4-methoxycarbonyl-1,3-dithiolan-2-yl, 2,4-dimethyl-4-ethoxycarbonyl-1,3-dioxolan-2-yl, 2,4-dimethyl-4-ethoxy-carbonyl-1,3-dithiolan-2-yl, 2,4-dimethyl-4-n-butoxycarbonyl-1,3-dioxolan-2-yl, 2,4-dimethyl-4-n-butoxycarbonyl-1,3-dithiolan-2-yl, 4-cyanomethyl-2-methyl-1,3-dioxolan-2-yl, 4-cyanomethyl-2-methyl-1,3-dithiolan-2-yl, 2-methyl-1,3-dioxan-2-yl, 2-methyl-1,3-dithian-2-yl, 2-methyl-1,3-oxathian-2-yl, 2,5-dimethyl-1,3-dioxan-2-yl, 2,5-dimethyl-1,3-dithian-2-yl, 2,5-dimethyl-1,3-oxathian-2-yl, 2,5,5-trimethyl-1,3-dioxan-2-yl, 2,4,6-trimethyl-1,3-dioxan-2-yl, 2,4,4-trimethyl-1,3-dioxan-2-yl, 2,5,5-trimethyl-1,3-dithian-2-yl, 2,4,6-trimethyl-1,3-dithian-2-yl, 2,4,4-trimethyl-1,3-dithian-2-yl, 2,5,5-trimethyl-1,3-oxathian-2-yl, 2,4,4-trimethyl-1,3-oxathian-2-yl, 2,6,6-trimethyl-1,3-oxathian-2-yl, 4-hydroxymethyl-2-methyl-1,3-dioxan-2-yl, 4-methoxymethyl-2-methyl-1,3-dioxan-2-yl, 4-allyloxymethyl-2-methyl-1,3-dioxan-2-yl, 4-acetoxymethyl-2-methyl-1,3-dioxan-2-yl, 4-hydroxymethyl-2-methyl-1,3-dithian-2-yl, 4-methoxymethyl-2-methyl-1,3-dithian-2-yl, 4-allyloxymethyl-2-methyl-1,3-dithian-2-yl, 4-acetoxymethyl-2-methyl-1,3-dithian-2-yl, 4-chloromethyl-2-methyl-1,3-dioxan-2-yl, 4-chloromethyl-2-methyl-1,3-dithian-2-yl, —$C(CH_3)$=NH, —$C(CH_3)$=N—$CH_3$, —$C(CH_3)$-N—$C_2H_5$, —$C(CH_3)$=N-n-$C_3H_7$, —$C(CH_3)$=N-i—$C_3H_7$, —$C(CH_3)$=N-n-$C_4mg$, —$C(CH_3)$=N—$CH_2CH$=$CH_2$, —$C(CH_3)$=N—$CH_2CH$—$CH_2$—$CH_3$, —$C(CH_3)$=N—$CH_2C$≡$CH$, —$C(CH_3)$=N—$CH_2C$≡$C$—$CH_3$, —$C(CH_3)$=N-cyclopropyl, —$C(CH_3)$=N-cyclobutyl, —$C(CH_3)$-N—cyclopentyl, —$C(CH_3)$=N-cyclohexyl, —$C(CH_3)$=N-cycloheptyl, —$C(CH_3)$=N—$CH_2$—$CH_2Cl$, —$C(CH_3)$=N—$CH_2Cl$, —$C(CH_3)$=N—$C_6H_5$, —$C(CH_3)$=N-(2-F—$C_6H_4$), —$C(CH_3)$=N-(3-F—$C_6H_4$), —$C(CH_3)$=N—(4—F—$C_6H_4$), —$C(CH_3)$=N-(2—Cl—$C_6H_4$), —$C(CH_3)$=N-(3—Cl—$C_6H_4$). —$C(CH_3)$=N-(4—Cl—$C_6H_4$), —$C(CH_3)$=N-(2—$CH_3$—$C_6C_6H_4$), —$C(CH_3)$=N-(3—$CH_3$—$C_6H_4$), —$C(CH_3)$=N-(4—$CH_3$—$C_6H_4$), —$C(CH_3)$=N-(2—$CF_3$—$C_6H_4$), —$C(CH_3)$=N-(3—$CF_3$—$C_6H_4$), —$C(CH_3)$=N-(4—$CF_3$—$C_6H_4$), —$C(CH_3)$=N-(2—$OCH_3$—$C_6H_4$), —$C(CH_3)$=N-(3—$OCH_3$—$C_6H_4$), —$C(CH_3)$=N-(4—$OCH_3$—$C_6H_4$), —$C(CH_3)$=N-(4—$NO_2$—$C_6H_4$), —$C(CH_3)$=N-(4—$CN$—$C_6H_4$), —$C(CH_3)$=N-(2,4—$Cl_2$—$C_6H_3$), —$C(CH_3)$=N-(2,4—$(CH_3)_2$—$C_6H_3$), —$C(CH_3)$=N—$CH_2$—$OCH_3$, —$C(CH_3)$=N—$CH_2$—$OC_2H_5$, —$C(CH_3)$=N—$CH_2CH_2$—$OCH_3$, —$C(CH_3)$=N—$CH_2CH_2$—$OC_2H_5$, —$C(CH_3)$=N—OH, —$C(CH_3)$=N—$OCH_3$, —$C(CH_3)$=N—$OC_2H_5$, —$C(CH_3)$=N—O-n-$C_3H_7$, —$C(CH_3)$=N—O-i-$C_3H_7$, —$C(CH_3)$=N—O-n-$C_4H_9$, —$C(CH_3)$=N—O-i—$C_4H_9$, —$C(CH_3)$=N—O-s-$C_4H_9$, —$C(CH_3)$=N—O-tert.—$C_4H_9$, —$C(CH_3)$=N—$OCH_2$—$CH$=$CH_2$, —$C(CH_3)$=N—OCH (CH$_3$) —CH=CH$_2$, —C(CH$_3$)=N—OCH$_2$—C≡CH, —C(CH$_3$)=N—CH(CH$_3$)—C≡CH, —C(CH$_3$)=N—OCH$_2$—CH—C—CH$_3$, —C(CH$_3$)=N—OCH$_2$CH$_2$—Cl, —C(CH$_3$)=N—OCH$_2$CH$_2$—F, —C(CH$_3$)=N—OCH$_2$—CF$_3$, —C(CH$_3$)=N—OCH$_2$—CH=CHCl, —C(CH$_3$)=N—OCH$_2$—C(Cl)—CH$_2$, —C(CH$_3$)=N—OCH$_2$—C(Br)=CH$_2$, —C(CH$_3$)=N—OCH$_2$—CH=C(Cl)—CH$_3$, —C(CH$_3$)=N—O—CO—CH$_3$, —C(CH$_3$)=N—OCO—CO$_2$H$_5$, —C(CH$_3$)=N—OCH$_2$—CN, —C(CH$_3$)=N—OCH$_2$—CH=CH—CH$_2$—OCH$_3$, —C(CH$_3$)=N—OCH$_2$—CH=CH—CH$_2$—O-tert.—C$_4$H$_9$, —C(CH$_3$)=N—O—(CH$_2$)3—C$_6$H$_5$, —C(CH$_3$)=N—O—(CH$_2$)$_4$—C$_6$H$_5$, —C(CH$_3$)=N—O—(CH$_2$)$_4$-(4—Cl—C$_6$H$_4$), —C(CH$_3$)=N—O—(CH$_2$)$_4$-(4—CH$_3$—C$_6$H$_4$), —C(CH$_3$)=N—O—(CH$_2$)$_4$-(4-CH$_3$—C$_6$H$_4$), —C(CH$_3$)N—OCH$_2$—CH=CH—(4-F—C$_6$H$_4$) —C(CH$_3$)=N—OCH$_2$—CH=CH—C$_6$H$_5$, —C(CH$_3$)=N—OCH$_2$—CH=CH—(4-F—C$_6$H$_4$), —C(CH$_3$)=N—OCH$_2$—CH=CH—(4—Cl—C$_6$H$_4$), —C(CH$_3$)=N—OCH$_2$—CH=CH—(3—CH$_3$O—C$_6$H$_4$), —C(CH$_3$)=N—O—(CH$_2$)$_2$—CH=CH—(4-F—C$_6$H$_4$), —C(CH$_3$)=N—O—(CH$_2$)$_2$—CH=CH—(4—Cl—C$_6$H$_4$), —C(CH$_3$)=N—OCH$_2$—CH=CH—CH$_2$—(4—CH$_3$O—C$_6$H$_4$), —C(CH$_3$)=N—OCH$_2$—CH=C(CH$_3$)—C$_6$H$_5$, —C(CH$_3$)=N—O—(CH$_2$)$_2$—CH=CH—(3,4—Cl$_2$—C$_6$H$_3$), —C(CH$_3$)=N—O—(CH$_2$)$_3$—C≡C—(4-F-C$_6$H$_4$), —C(CH$_3$)=N—OCH$_2$—OCH$_3$, —C(CH$_3$)=N—OCH$_2$CH$_2$—OCH$_3$, —C(CH$_3$)=N—OCH$_2$—OC$_2$H$_5$, —C(CH$_3$)=N—OCH(CH$_3$)—OCH$_3$, —C(CH$_3$)=N—OCH(CH$_3$)—CO—OCH$_3$, —C(CH$_3$)=N—OCH(CH$_3$)—CO—O-n-C$_4$H$_9$, —C(CH$_3$)=N—NH$_2$, —C(CH$_3$)=N—NH—CH$_3$, —C(CH$_3$)=N—NH—C$_2$H$_5$, —C(CH$_3$)=N—NH-n-C$_3$H$_7$, —C(CH$_3$)=N—NH-i-C$_3$H$_7$, —C(CH$_3$)=N—NH-n-C$_4$H$_9$, —C(CH$_3$)=N—NH-i-C$_4$H$_9$, —C(CH$_3$)=N—NH-s—C$_4$H$_9$, —C(CH$_3$)=N—NH-tert.—C$_4$H$_9$, —C(CH$_3$)=N—NH-cyclopropyl, —C(CH$_3$)=N—NH-cyclobutyl, —C(CH$_3$)=N—NH-cyclopentyl, —C(CH$_3$)=N—NH-cyclohexyl, —C(CH$_3$)=N—NH-cycloheptyl, —C(CH$_3$)=N—N(CH$_3$)$_2$, —C(CH$_3$)=N—N(C$_2$H$_5$)$_2$, —C(CH$_3$)=N—N(1n-C$_3$H$_7$)$_2$, —C(CH$_3$)=N—N(i—C$_3$H$_7$)$_2$, —C(CH$_3$)=N—NH—CH$_2$—C≡CH, —C(CH$_3$)=N—NH—CH$_2$—C≡CH, —C(CH$_3$)N—N(CH$_3$)—CH$_2$—C≡CH, —C(CH$_3$)=N—NH—CH$_2$CF$_3$, —C(CH$_3$)=N—NH—CO—CH$_3$, —C (CH$_3$)=N—NH—CO—C$_2$H$_5$, —C(CH$_3$)=N—NH—CO—OCH$_3$, —C(CH$_3$)=N—NH—CO—OC$_2$H$_5$, —C(CH$_3$)-N—NH—CO—O-tert.—C$_4$H$_9$, —C(CH$_3$)=N-pyrrolidin-1-yl, —C(CH$_3$)=N-piperidin-1-yl, —C(CH$_3$)=N-morpholin-4-yl, —C(CH$_3$)=N—NH—C$_6$H$_5$, —C(CH$_3$)=N—NH—($_4$—Cl—C$_6$H$_4$), —C(CH$_3$)=N—NH—($_4$-NO$_2$—C$_6$H$_4$), —C(CH$_3$)=N—NH—($_4$-F—C$_6$H$_4$), —C(CH$_3$)=N—NH—($_4$—CH$_3$O—C$_6$H$_4$) —C(CH$_3$)=N—NH—(2,4—C$_{12}$—C$_6$H$_3$), —C(CM$_3$)=N—NH—(2,4-(No$_2$)$_2$—C$_6$H$_3$), —C(CH$_3$)=N—NH—CO—NH$_2$, —C(CH$_3$)=N—NH—CO—NHCH$_3$, —C(CH$_3$)=N—NH—CO—NHC$_2$H$_5$, —C(CH$_3$)=N—NH—CO—N(CH$_3$)$_2$, —C(CH$_3$)CH—COOH, —C(CH$_3$)—CH—CO—OCH$_3$, —C(CH$_3$)=CH—CO—OC$_2$H$_5$, —C(CH$_3$)=CH—CO—O-n-C$_3$H$_7$, —C(CH$_3$)=CH—CO—i-C$_3$H$_7$, —C(CH$_3$)—CH—CO—O-n-C$_4$H$_9$, —C(CH$_3$)=CH—CO—O-tert.—C$_4$H$_9$, —C(CH$_3$)=CH—CO—O-cyclopropyl, —C(CH$_3$)=CH—CO—O-cyclobutyl, —C(CH$_3$)—CH—Ca—O-cyclopentyl, —C(CH$_3$)=CH—CO—O-cyclohexyl, —C(CH$_3$)=CH—CO—O-cycloheptyl, —C(CH$_3$)—C(CH$_3$)—COOH, —C(CH$_3$)—C(CH$_3$)—CO—OCH$_3$, —C(CH$_3$)=C(CH$_3$)—CO—OCH$_5$, —C(CH$_3$)=C(CH$_3$)—CO—O-n-C$_3$H$_7$, —C(CH$_3$)=C(CH$_3$)—CO—i—C$_3$H$_7$, —C(CH$_3$)=C(CH$_3$)—CO—O-n-C$_4$H$_9$, —C(CH$_3$)=C(CH$_3$)—CO—O-tert.—C$_4$H$_9$, —C(CH$_3$)—C(CH$_3$)—CO—O-cyclopropyl, —C(CH$_3$)—C(CH$_3$)—CO—O-cyclobutyl, —C(CH$_3$)—C(CH$_3$)—CO—O-cyclopentyl, —C(CH$_3$)=C(CH$_3$)—CO—O-cyclohexyl, —C(CH$_3$)=C(CH$_3$)—CO—-cycloheptyl, —C(CH$_3$)=C(C$_2$H$_5$)—COOH, —C(CH$_3$):C(C$_2$H$_5$)—CO—OCH$_3$, —C(CH$_3$)=C(C$_2$H$_5$)—CO—C$_2$H$_5$, —C(CH$_3$)$_3$C(C$_2$H$_5$)—CO—O-n-C$_3$H$_7$, —C(CH$_3$)=C(C$_2$H$_5$)—CO-i—C$_3$H$_7$, —C(CH$_3$)=C(C$_2$H$_5$)—CO—O-n-C$_4$H$_9$, —C(CH$_3$)=C(C$_2$H$_5$)—CO—O-tert.—C$_4$H$_9$, —C(CH$_3$)—C(C$_2$H)—CO—O—cyclo-propyl, —C(CH$_3$)=C(C$_2$H$_5$)—CO—O-cyclobutyl, —C(CH$_3$)=C(C$_2$H$_5$)—CO—O-cyclopentyl, —C(CH$_3$)=C(C$_2$H$_5$)—CO—O-cyclohexyl, —C(CH$_3$)=C(C$_2$H$_5$)—CO—O-cycloheptyl, —C(CH$_3$)=CH—COOH, —C(CH$_3$)=CH—CO—OCH$_3$, —C(CH$_3$)=CH—CO—OC$_2$H$_5$, —C(CH$_3$)=C(Cl)—CO—O-n-C$_3$H$_7$, —C(CH$_3$)=Cl)—CO—i—C$_3$H$_7$, —C(CH$_3$)=C(Cl)—CO—O-n-C$_4$H$_9$, —C(CH$_3$)C(Cl)—CO—O-tert.—C$_4$H$_9$, —C(CH$_3$)=C(Cl)—CO—O-cyclopropyl, —C(CH$_3$)=C(Cl)—CO—O-cyclobutyl, —C(CH$_3$)=C(Cl)—CO—O-cyclopentyl, —C(CH$_3$)=C(Cl)—CO—O-cyclohexyl, —C(CH$_3$)=C(Cl)—CO—O-cycloheptyl, —C(CH$_3$)=C(Br)—COOH, —C(CH$_3$)=C(Sr)—CO—OCH$_3$, —C(CH$_3$)=C(Br)—CO—OC$_2$H$_5$, —C(CH$_3$)=C(Br)—CO—O-n-C$_3$H$_7$, —C(CH$_3$)=C(Br)—CO—i—C$_3$H$_7$, —C(CH$_3$)=C(Br)—CO—O-n-C$_4$H$_9$, —C(CH$_3$)=C(Br)—CO—O-tert.-C$_4$H$_9$, —C(CH$_3$)=C(Br)—CO—O-cyclopropyl, —C(CH$_3$)=C(Br)—CO—O-cyclobutyl, —C(CH$_3$)=C(Br)—CO—O-cyclopentyl, —C(CH$_3$)=C(Br)—CO—O-cyclohexyl, —C(CH$_3$)=C(Br)—CO—O-cycloheptyl, —C (CH$_3$)=C(CN)—COOH, —C(CH$_3$)=C(CN)—CO—OCH$_3$, —C(CH$_3$)=C(CN)—CO—OC$_2$H$_5$, —C(CH$_3$)=C(CN)—CO—O-n-C$_3$H$_7$, —C(CH$_3$)=C(CN)—CO—i—C$_3$H$_7$, —C(CH$_3$)=C(CN)—CO—O-n-C$_4$H$_9$, —C(CH$_3$)=C(CN)—CO—O-tert.—C$_4$H$_9$g, —C(CH$_3$)=C(CN)—CO—O-cyclopropyl, —C(CH$_3$)=C(CN)—CO—O-cyclobutyl, —C(CH$_3$)=C(CN)—CO—O-cyclopentyl, —C(CH$_3$)=C(CN)—CO—O-cyclohexyl, —C(CH$_3$)=C(CN)—CO-o-cycloheptyl, —C(CH$_3$)=CH—CO—OCH$_2$—OCH$_3$, —C(CH$_3$)=CH—CO—OCH$_2$—OC$_2$H$_5$, —C(CH$_3$)=CH—CO—OCH$_2$—O-n-C$_3$H$_7$, —C(CH$_3$)=CH—CO—O-i—C$_3$H$_7$, —C(CH$_3$)=CH—CO—OCH(CH$_3$)—OCH$_3$, —C(CH$_3$)=CH—CO—OCH(CH$_3$)—OC$_2$H$_5$, —C (CH$_3$)—CH—CO—OCH$_{2CH2}$—OCH$_3$, —C(CH$_3$)=CH—CO—OCH$_2$CH$_2$—OC$_2$H$_5$, —C(CH$_3$)=C(CH$_3$)—CO—

OCH₂—OCH₃, —C(CH₃)=C(CH₃)—C)—OCH₂—OC₂H₅, —C(CH₃)=C(CH₃)—CO—OCH₂—O-n-C₃H₇, —C(CH₃)=C(CH₃)—CO—O-i—C₃H₇, —C(CH₃)—C(CH₃)—CO—OCH(CH₃)—OCH₃, —C(CH₃)=C(CH₃)—CO—OCH(CH₃)—OC₂H₅, —C(CH₃)=C(CH₃)—CO—OCH₂CH₂—OCH₃, —C(CH₃)=C(CH₃)—Co-oCH₂CH₂-oC₂H₅, —C(CH₃)—C(C₂H₅)-CO—OcH₂—OCH₃, —C(CH₃)=C(C₂H₅)—CO—OCH₂—OC₂H₅, —C(CH₃)=C(C₂M₅)—CO—OCH₂-O-n-C₃H₇, —C(CH₃)=C(C₂H₅)—CO—O-i—C₃H₇, —C(CH₃)=C(C₂H₅)—CO—OCH(CH₃)—OCH₃, —C(CH₃)=C(C₂H₅)—CO—OCH(CH₃)—OC₂H₅, —C(CH₃)=C(C₂H₅)—CO—OCH₂CH₂—OCH₃, —C(CH₃)=C(C₂H₅)—CO—OCH₂CH₂—OC₂H₅, —C(CH₃)=C(Cl)—CO—OCH₂—OCH₃, —C(CH₃)=C(Cl)—CO—OCH₂—OC₂H₅, —C(CH₃)—C(Cl)—CO—OCH₂-O-n-C₃H₇, —C(CH₃)=C(Cl)—CO—O-i—C₃H₇, —C(CH₃)—C(Cl)—CO—OCH(CH₃)—OCH₃, —C(CH₃)=C(Cl)—CO—OCH(CH₃)—OCH₅, —C(CH₃)=C(Cl)—CO—OCH₂CH₂—OCH₃, —C(CH₃)=C(Cl)—CO—OCH₂CH₂—OC₂H₅, —C(CH₃)=C(Br)—CO—OCH₂—OCH₃, —C(CH₃)=C(Br)—CO—OCH₂—OCH₅, —C(CH₃)=C(Br)—CO—OCH₂-O-n-C₃H₇, —C(CH₃)=C(Br)—CO—O-i—C₃H₇, —C(CH₃)=C(Br)—CO—OCH(CH₃)—OCH₃, —C(CH₃)=C(Br)—CO—OCH(CH₃)—OCH₃, —C(CH₃)=C(Cl)—CO—OCH₂CH₂—OCH₃—C(CH₃)=C(Br)—CO—OCH₂CH₂—OC₂H₅, —C(CH₃)=C(CN)—CO—OCH₂—OCH₃, —C(CH₃)=C(CN)—CO—OCH₂—OC₂H₅, —C(CH₃)=C(CN)—CO—OCH₂—O-n-C₃H₇, —C(CH₃)=C(CN)—CO—O-i—C₃H₇, —C(CH₃)=C(CN)—CO—OCH(CH₃)—OCH₃, —C(CH₃)=C(CN)—CO—OCH(CH₃)—OC₂H₅, —C(CH₃)—C(CN)—CO—OCH₂CH₂—OCH₃, —C(CH₃)=C(CN)—CO—OCH₂CH₂—OC₂H₅, —C(CH₃)=CH—CO—OCH₂—CF₃, —C(CH₃)=CH—CO—OCH₂—CCl₃, —C(CH₃)—CH—CO—OCH₂-oxiranyl, —C(CH₃)=CH—CO—O—(CH₂)₃-Br, —C(CH₃)=CH—CO—OCH₂—CH=CH₂, —C(CH₃)=CH—CO—OCH₂—C≡CH, —C(CH₃)=CH—CO—OCH₂—CN, —C(CH₃)=CH—CO—OCH₂CH₂—CN, —C(CH₃)=C(CH₃)—CO—OCH₂—CF₃, —C(CH₃)=C(CH₃)—CO—OCH₂—CCl₃, —C(CH₃)=C(CH₃)—CO—OCH₂-oxiranyl, —C(CH₃)=C(CH₃)—CO—O—(CH₂)₃-Br, —C(CH₃)=C(CH₃)—CO—OCH₂—CH=CH₂, —C(CH₃)=C(CH₃)—CO—OCH₂—C≡CH, —C(CH₃)=C(CH₃)—CO—OCH₂—CN, —C(CH₃)—CO—OCH₂CH₂—CN, —C(CH₃)=C(C₂H₅)—CO—OCH₂—CF₃, —C(CH₃)=C(C₂H₅)—CO—OCH₂—Cl₃, —C(CH₃)=C(C₂H₅)—CO—OCH₂-oxiranyl, —C(CH₃)=C(C₂H₅)—CO—O—(CH₂)₃-Br, —C(CH₃)=C(C₂H₅)—CO—OCH₂—CH=CH₂, —C(CH₃)=C(C₂H₅)—CO—OCH₂—C≡CH, —C(CH₃)=C(C₂H₅)—CO—OCH₂—CN, —C(CH₃)=C(C₂H₅)—CO—OCH₂CH₂—CN, —C(CH₃)=C(Cl)—CO—OCH₂—CF₃, —C(CH₃)=C(Cl)—CO—OCH₂—Cl₃, —C(CH₃)=C(Cl)—CO—OCH₂-oxiranyl, —C(CH₃)=C(Cl)—CO—O—(CH₂)₃-Br, —C(CH₃)=C(Cl)—CO—OCH₂—CH=CH₂, —C(CH₃)=C(Cl)—CO—OCH₂—C≡CH, —C(CH₃)=C(Cl)—CO—OCH₂—CN, —C(CH₃)=C(Cl)—CO—OCH₂CH₂—CN, —C(CH₃)=C(Br)—CO—OCH₂—CF₃, —C(CH₃)=C(Br)—CO—OCH₂—Cl₃, —C(CH₃)=C(Br)—CO—OCH₂-oxiranyl, —C(CH₃)=C(Br)—CO—O—(CH₂)₃-Br, —C(CH₃)=C(Br)—CO—OCH₂—CH=CH₂, —C(CH₃)=C(Br)—CO—OCH₂—C≡CH, —C(CH₃)=C(Br)—CO—OCH₂—CN, —C(CH₃)=C(Br)—CO—OCH₂CH₂—CN, —C(CH₃)=C(CN)—CO—OCH₂—CF₃, —C(CH₃)=C(CN)—CO—OCH₂—Cl₃, —C(CH₃)=C(CN)—CO—OCH₂-oxiranyl, —C(CH₃)=C(CN)—CO—O+(CH₂)₃-Br, —C(CH₃)=C(CN)—CO—OCH₂—CH=CH₂, —C(CH₃)=C(CN)—CO—OCH₂—C=—CH, —C(CH₃)=C(CN)—CO—OCH₂—CN, —C(CH₃)=C(CN)—CO—OCH₂CH₂—CN, —C(CH₃)—CH—CO—CH₃, —C(CH₃)=CH—CO—C₂H₅, —C(CH₃)=CH—CO-n-C₃H₇, —C(CH₃)=CH—CO-i-C₃H₇, —C(CH₃)=CH—CO-n-C₄H₉, —C(CH₃)—CH—CO—tert.—C₄H₉, —C(CH₃)=CH—CO—CH₂Cl, —C (CH₃)=CH—CO—CH₂Br, —C(CH₃)=CH—CO—CHCl₂, —C(CH₃)=CH—CO—CH₂—OCH₃, —C(CH₃)=CH—CO—CH(OCH₃)₂, —C(CH₃)=CH—CO—CH₂—SCH₃, —C(CH₃)=C(CH₃)—CO—CH₃, —C(CH₃)=C(CH₃)—CO—C₂H₅, —C(CH₃)=C(CH₃) —CO-n-C₃H₇, —C(CH₃)=C(CH₃)—CO—i—C₃H₇, —C(CH₃)=C(CH₃)—CO-n-C₄H₉, —C(CH₃)=C(CH₃)—CO—tert.—C₄H₉—C(CH₃)=C(CH₃)—CO—CH₂Cl, —C(CH₃)=C(CH₃)—CO—CH₂Br, —C(CH₃)—C(CH₃)—CO—CHCl₂, —C(CH₃)=C(CH₃)—CO—CH₂—OCH₃, —C(CH₃)=C(CH₃)—CO—CH(OCH₃)₂, —C(CH₃)=C(CH₃)—CO—CH₂—SCH₃, —C(CH₃)=C(C₂H₅)—CO—CH₃, —C(CH₃)=C(C₂H₅)—CO—C₂H₅, —C(CH₃)=C(C₂H₅)—CO-n-C₃H₇, —C(CH₃)=C(C₂H₅)—CO-i—C₃H₇, —C(CH₃)=C(C₂H₅)—CO-n-C₄H₉, —C(CH₃)=C(C₂H₅)—CO—tert.—C₄H₉, —C(CH₃)=C(C₂H₅)—CO—CH₂Cl, —C(CH₃)=C(C₂H₅)—CO—CH₂Br, —C(CH₃)=C(C₂H₅)—CO—CHCl₂, —C(CH₃)=C(C₂H₅)—CO—CH₂—OCH₃, —C(CH₃)=C(C₂H₅)—CO—CH(OCH₃)₂, —C(CH₃)=C(C₂H₅)—CO—CM₂—SCH₃, —C(CH₃)=C(Cl)—CO—CH₃, —C(CH₃)=C(Cl)—CO—C₂H₅, —C(CH₃)=C(Cl)—CO-n-C₃H₇, —C(CH₃)=C(Cl)—CO—i—C₃H₇, —C(CH₃)=C(Cl)—CO-n-C₄H₉, —C(CH₃)=C(Cl)—CO—tert.—C₄H₉, —C(CH₃)=C(Cl)—CO—CH₂Cl, —C(CH₃)=C(Cl)—CO—CHCl₂, —C(CH₃)=C(Cl)—CO—CH₂—OCH₃, —C(CH₃)=C(Cl)—CO—CH(OCH₃)₂, —C(CH₃)=C(Cl)—CO—CH₂—SCH₃, —C(CH₃)=C(Br)—CO—CH₃, —C(CH₃)—C(Br)—CO—C₂H₅, —C(CH₃)=C(Br)—CO-n-C₃H₇, —C(CH₃)=C(Br)—CO—i—C₃H₇, —C(CH₃)=C(Br)—CO-n-C₄H₉, —C(CH₃)=C(Br)—CO—tert.—C₄H₉, —C(CH₃)=C(Br)—CO—CH₂Cl, —C(CH₃)=C(Br)—CO—CH₂Br, —C(CH₃)=C(Br)—CO—CH₂—OCH₃, —C(CH₃)=C(Br)—CO—CH(OCH₃)₂, —C(CH₃)=C(Br)—CO—CH₂—SCH₃, —C(CH₃)—C(CN)—CO—CH₃, —C(CH₃)=C(CN)—CO—C₂H₅, —C(CH₃)=C(CN)—CO-n-C₃H₇, —C(CH₃)=C(CN)—CO—i—C₃H₇, —C(CH₃)

=C(CN)—CO-n-C₄H₉, —C(CH₃)=C(CN)—CO—tert.—C₄H₉, —C(CH₃)=C(CN)—CO—CH₂Cl, —C(CH₃)=C(CN)—CO—CH₂Br, —C(CH₃)=C(CN)—CO—CHCl₂, —C(CH₃)=C(CN)—CO—CH₂—OCH₃, —C(CH₃)=C(CN)—CO—CH(OCH₃)₂, —C(CH₃)=C(CN)—CO—CH₂—SCH₃, —C(CH₃)=CH—CO—C₆H₅, —C(CH₃)=CH—CO—(₄—C₁—C₆H₄), —C(CH₃)=C(CH₃)—CO—C₆H₅, —C(CH₃)=C(CH₃)—CO—(₄—Cl—C₆H₄), —C(CH₃)—C(C₂H₅)—CO—C₆H₅, —C(CH₃)=C(C₂H₅)—CO—(4—Cl—C₆H₄), —C(CH₃)—C(Cl)—CO—C₆H₅, —C(CH₃)=C(Br)—CO—C₆H₅, —C(CH₃)=C(CN)—CO—C₆H₅, —C(CH₃)=CH—CO—NH₂, —C(CH₃)=CH—CO—NHCH₃, —C(CH₃)=CH—CO—N(CH₃)₂, —C(CH₃)=CH—CO—NN—C₂H₅, —C(CH₃)=CH—CO—N(C₂H₅)₂, —C(CH₃)=CH—CO—NH-n-C₃H₇, —C(CH₃)—CH—CO—NH-i—C₃H₇, —C(CH₃)=CH—CO—NH-tert.—C₄H₉, —C(CH₃)=CH—CO—NH-cyclopropyl, —C(CH₃)=CH—CO—NH—cyclobutyl, —C(CH₃)—CH—CO—NH-cyclopentyl, —C(CH₃)=CH—CO—NH-cyclohexyl, —C(CH₃)—CH—CO—NH-cycloheptyl, —C(CH₃)=CH—CO—NH-cyclooctyl, —C(CH₃)—CH—CO—pyrrolidin-1-yl, —C(CH₃)=CH—CO—piperidin-₁-yl, —C(CH₃)=C—CO—morpholin-₄-yl, —C(CH₃)=CH—CO—NH—CH₂CH=CH₂, —C(CH₃)=CH—CO—NH—CH₂C≡CH, —C(CH₃)=CH—CO—N(CH₃)—CH₂C≡CH, —C(CH₃)—CH—CO—NH—(CH₂)₂Cl, —C(CH₃)=CH—CO—NH—C₆H₅, —C(CH₃)=C(CH₃)—CO—NH₂, —C(CH₃)=C(CH₃)—CO—NHCH₃, —C(CH₃)—C(CH₃)—CO—N(CH₃)₂, —C(CH₃)=C(CH₃)—CO—NH—C₂H₅, —C(CH₃)=C(CH₃)—CO—N(C₂H₅)₂, —C(CH₃)=C(CH₃)—CO—NH-n-C₃H₇, —C(CH₃)=C(CH₃)—CO—NH-i—C₃H₇, —C(CH₃)=C(CH₃)—CO—NH-tert.—C₄H₉, —C(CH₃)—C(CH₃)—CO—NH-cyclopropyl, —C(CH₃)=C(CH₃)—CO—NH—cyclobutyl, —C(CH₃)=C(CH₃)—CO—NH—cyclopentyl, —C(CH₃)—C(CH₃)—CO—NH-cyclohexyl, —C(CH₃)=C(CH₃)—CO—NH—cycloheptyl, —C(CH₃)=C(CH₃)—CO—NH—cyclooctyl, —C(CH₃)=C(CH₃)—CO—pyrrolidin-1-yl, —C(CH₃)=C(CH₃)—CO—piperidin-₁-yl, —C(CH₃)=C(CH₃)—CO—morpholin-₄-yl, —C(CH₃)=(CH₃)—CO—NH—CH₂CH—C(CH₃)₂, —C(CH₃)=C(CH₃)—CO—NH—CH₂C≡CH, —C(CH₃)=C(CH₃)—CO—N(CH₃)—CH₂C≡CH, —C(CH₃)=C(CH₃)—CO—NH—(CH₂)₂Cl, —C(CH₃)=C(CH₃)—CO—NH—C₆H₅, —C(CH₃)=C(C₂H₅)—CO—NH₂, —C(CH₃)=C(C₂H₅)—CO—NHCH₃, —C(CH₃)=C(C₂H₅)—CO—N(CH₃)₂, —C(CH₃)=C(C₂H₅)—CO—NH—C₂H₅, —C(CH₃)=C(C₂H-)—CO—N(C₂H₅)₂, —C(CH₃)=C(C₂H₅)—CO—NH₄-n-C₃H₇, —C(CH₃)sC(C₂H₅)—CO—NH-i—C₃H₇, —C(CH₃)=C(C₂H₅)—CO—NH-tert.—C₄H₉, —C(CH₃)=C(C₂H₅)—CO—NH-cyclopropyl, —C(CH₃)=C(C₂H₅)—CO—NH-cyclobutyl, —C(CH₃)=C(C₂H₅)—CO—NM-cyclopentyl, —C(CH₃)=C(C₂H₅)—CO—NH-cyclo-hexyl, —C(CH₃)=C(C₂H₅)—CO—NH—cycloheptyl, —C(CH₃)=C(C₂H₅) )—CO—NH-cyclooctyl, —C(CH₃)=C(C₂H₅)—CO—pyrrolidin-1-yl, —C(CH₃)=C(C₂H₅)—CO-piperidin-1-yl, —C(CH₃)=C(C₂H₅)—CO—morpholin-4-yl, —C(CH₃)=C(C₂H₅)—CO—NH—CH₂CH=C(C₂H₅)₂, —C(CH₃)=C(C₂H₅)—CO—NH—CH₂C—SCH, —C(CH₃)—C(C₂H₅)—CO—N(CH₃)—CH₂C-=CH, —C(CH₃)=C(C₂H₅)—CO—NH—(CH₃) ₂Cl, —C(CH₃)=C(C₂H₅)—CO—NH—C₆H₅, —C(CH₃)=C(Cl)—CO—NH₂, —C(CH₃)—C(Cl)—CO—NHCH₃, —C(CH₃)=C(C₁)—CO—N(CH₃)₂, —C(CH₃)=C(Cl)—CO—NH—C₂H₅, —C(CH₃)=C(Cl)—CO—N(C₂H₅)₂, —C(CH₃)=C(Cl)—CO—NH-n-C₃H₇, —C(CH₃)=C(Cl)—CO—NH-i—C₃H₇, —C(CH₃)=C(Cl)—CO—NH-tert.—C₄H₉, —C(CH₃)=C(Cl)—CO—NH-cyclopropyl, —C(CH₃)=C(Cl)—CO—NH—cyclobutyl, —C(CH₃)=C(Cl)—CO—NH-cyclopentyl, —C(CH₃)=C(Cl)—CO—NH-cyclohexyl, —C(CH₃)=C(Cl)—CO—NH-cycloheptyl, —C(CH₃)—C(Cl )—CO—NH-cyclooctyl, —C(CH₃)=C(Cl )—CO—pyrrolidin-1-yl, —C(CH₃)=C(Cl)—CO—piperidin-1-yl, —C(CH₃)=C(Cl)—CO—morpholin-4-yl, —C(CH₃)=C(Cl)—CO—NH—CH₂CH=C)(Cl)₂, —CH₃)=C(Cl)—CO—NH—CH₂C≡CH, —C(CH₃)=C(Cl)—CO—N(CH₃)—CH₂C₅CH, —C(CH₃)=C(Cl)—CO—NH—(CH₂)₂Cl, —C(CH₃)=C(Cl)—CO—NH—C₆H₅, —C(CH₃)=C(Br)—CO—NH₂, —C(CH₃)=C(Br)—CO—NHCH₃, —C(CH₃)=C(Br)—CO—N(CH₃)₂, —C(CH₃)=C(Br)—CO—NH—C₂H₅, —C(CH₃)=C(Br)—CO—N(C₂H₅)₂, —C(CH₃)=C(Br)—CO—NH-n-C₃H₇, —C(CH₃)—C(Br)—CO—NH-i—C₃H₇, —C(CH₃)=C(Br)—CO—NH-tert.—C₄H₉, —C(CH₃)=C(Br)—CO—NH-cyclopropyl, —C(CH₃)=C(Br)—CO—NH-cyclobutyl, —C(CH₃)—C(Br)—CO—NH-cyclopentyl, —C(CH₃)=C(Br)—CO—NH-cyclohexyl, —C(CH₃)=C(Br)—CO—N-cycloheptyl, —C(CH₃)=C(Br)—CO—NH-cyclooctyl, —C(CH₃)=C(Br)—CO—pyrrolidin-1-yl, —C(CH₃)=C(Br)—CO—piperidinl-1-yl, —C(CH₃)=C(Br)—CO—morpholin-4-yl, —C(CH₃)=C(Br)—CO—NH—CH₂CH=C(Br)₂, —C(CH₃)=C(Br)—CO—NH—CH₂C≡CH, —C(CH₃)=C(Br)—CO—N(CH₃)—CH₂C—CH, —C(CH₃)=C(Br)—CO—NH—(CH₂)₂Cl, —C(CH₃)=C(Br)—CO—NH—C₆H₅, —C(CH₃)=C(CN)—CO—NH₂, —C(CH₃)=C(CN)—CO—NHCH₃, —C(CH₃)=C(CN)—CO—N(CH₃)₂, —C(CH₃)=C(CN)—CO—NH—C₂H₅, —C(CH₃)=C(CN)—CO—N(C₂H₅)₂, —C(CH₃)=C(CN)—CO—NH-n-C₃H₇, —C(CH₃)—C(CN)—CO—NH-i—C₃H₇, —C(CH₃)=C(CN)—CO—NH-tert.—C₄H₉, —C(CH₃)—C(CN)—CO—NH-cyclopropyl, —C(CH₃)=C(CN)—CO—NH—cyclobutyl, —C(CH₃)=C(CN)—CO—NH-cyclopentyl, —C(CH₃)=C(CN)—CO—NH-cyclohexyl, —C(CH₃)C(CN)—CO—NH—cycloheptyl, —C(CH₃)=C(CN)—CO—NH-cyclooctyl, —C(CH₃)=C(CN)—CO—pyrrolidin-1-yl, —C(CH₃)=C(CN)—CO—piperidin-1-yl, —C(CH₃)=C(CN)—CO—morpholin-4-yl, —C(CH₃)=C(CN)—CO—NH—CH₂CH=C(CN)₂, —C(CH₃)=C(CN)—CO—NH—CH₂C≡CH, —C(CH₃)=C(CN)—CO—N(CH₃)—CH₂C₅CH,
—C(CH₃)=C(CN)—CO—NH—(CH₂)₂Cl,
—C(CH₃)=C(CN)—CO—NH—C₆H₅, —C(CH₃)
=CH—CO—SCH₃, —C(CH₃)=CH—CO—SC₂H₅,
—C(CH₃)=CH—CO—S-n-C₃H₇, —C(CH₃)=CH—
CO—S-i—C₃H₇, —C(CH₃)=CH—CO—S-n-C₄H₉,
—C(CH₃)=CH—CO—S-tert—C₄H₉—C(CH₃)—C
(CH₃)—CO—SCH₃, —C(CH₃)=C(CH₃)—CO—
SC₂H₅ —C(CH₃)=C(CH₃)—CO-S-n-C₃H₇,
—C(CH₃)=C(CH₃)—CO—S-i—C₃H₇, —C(CH₃)—
C(CH₃)—CO—S-n-C₄H₉, —C(CH₃)=C(CH₃)—
CO—S-tert.—C₄H₉, —C(CH₃)=C(C₂H₉)—CO—
SCH₃, —C(CH₃)=C(C₂H₅)—CO—SC₂H₃,
—C(CH₃)=C(C₂H)—CO—S-n-C₃H, —C(CH₃)=C
(C₂H₅)—CO—S-i—C₃H₇, —C(CH₃)—C(C₂H₅l—
CO—S-n-C₄H₉ —C(CH₃)=C(C₂H₅)—CO-S-tert.—
C₄H₉, —C(CH₃)—C(Cl)—CO—SCH₃, —C(CH₃)=C
(Cl)—CO—SC₂H₅, —C(CH₃)=C(C)—CO—S-n-
C₃H₇, —C(CH₃)=C(Cl)—CO—S-i—C₃H₇,
—C(CH₃)=C(Cl)—CO—S-n-C₄H₉, —C(CH₃)=C
(Cl)—CO-S-tert—C₄H₉, —C(CH₃)=C(Br)—CO—
SCH₃, —C(CH₃)=C(Br)—CO—SC₂H₅, —C(CH₃)
=C(CN)—CO—S-n-C₃H₇, —C(CH₃)=C(Br)—
CO—S-i—C₃H₇, —C(CH₃)=C(Br)—CO—S-n-
C₄H₉, —C(CH₃)=C(Br)—CO—S-tert.—C₄H₉,
—C(Cl₃)=C(CN)—CO—OCH₃, —C(CH₃)=C
(CN)—CO—SC₂H, —C(CH₃)—C(CN)—CO—S-n-
C₃H₇, —C(CH₃)=C(CN)—CO—S-i—C₃H₇, —C
(CH₃)=C(CN)—CO—S-n-C₄H₉, —C(CH₃)=C
(CN)—CO—S-tert.—C₄H₉, —C(CH₃)=C
(COCH₃)—CO—OCH₃, —C(CH₃)=C(COC₂H₅)—
CO—OCH₃, —C(CH₃)=C(CO-n-C₃H₇)—CO—
OCH₃, —C(CH₃)=C(COCH₃)—CO—OC₂H₅,
—C(CH₃)=C(COC₂H₅)—CO—OC₂H₅, —C(CH₃)
=C(C-n-C₃H₇)—CO—OC₂H₅, —C(CH₃)
C=COCH₃)—CO—O-n-C₃H₇, —C(CH₃)=C
(COC₂H₅)—CO—O-n-C₃H₇, —C(CH₃)=C(CO-n-
C₃H₇)—CO—O-n-C₃H₇, —C(CH₃)=C(CF₃)—CO—
OCH₃, —C(CH₃)=C(CF₃)—CO—OC₂H₅, —C(CH₃)
=C(CF₃)—CO—OCH—C₃H₇, —C(CH₃)—C
(CF₃)—CO—O-i—C₃H₇, —C(CH₃)=C (CF₃)—
CO—O-n-C₄H₉, —C(CH₃)=C(CF₃)—CO—O-tert
.—C₄H₉, —C(CH₃)=C(COOCH₃)₂, —C(CH₃)C
(COOC₂H₅)₂, —C(CH₃)=C(COOCH₃)—CO—
OC₂H₅, —C(CH₃)=C(COO-n-C₃H₇)—CO—OCH₃.
—C(CH₃)=C(COO-n-C₃H₇)—CO—OC₂H₅,
—C(CH₃)=C(COO-n-C₃H₇)₂, —C(CH₃)=CH—
CH=CH—COOH, —C(CH₃)=CH—CH=CH—
CO—OCH₃, —C(CH₃)=CH—CH=CH—CO—
OC₂H₅, —C(CH₃)=CH—CH=C(COOCH₃)₂,
—C(CH₃)=CH—CH=C(CN)—CO—OCH₃,
—C(CH₃)—CH—CH=C(CN)—CO—OC₂H₅,
—C(CH₃)=C(CH₃)—CH=C(CN)—CO—OCH₃,
—C(CH₃)=C(CH₃)—CH—C(CN)—CO—OC₂H₅,
—C(CH₃)=C(CH₃)—CH=C(CH₃)—CO—OCH₃,
—C(CH₃)—C(CH₃)—CH=C(Cl)—CO—OCH₃,
—C(CH₃)—C(CH₃)—CH=C(Br)—CO—OCH₃,
—C(CH₃)=C(CH₃)—CH=C(CH₃)—CO—OC₂H₅,
—C(CH₃)=C(CH₃)—CH=C(Cl)—CO—OC₂H₅,
—C(CH₃)=C(Br)CO—OC₂H₅(—C(CH₃)=C
(CH₃)—CH=C(CN)—CO—NH₂, —C(CH₃)=C
(C₃)—CH=C(CN)—CO—NH—CH₃, —C(CH₃)
=CH—(CH₂)₂—COOH, —C(CH₃)=CH(CH₂)₂—
CO—OCH₃—C(CH₃)—CH—(CH₂)₂—CO—OC₂H₅,
—C(CH₃)=CH—CH₂—CH(COOCH₃)₂, —C(CH₃)
=CH—CH₂—CH(COOC₂H₅)₂, —C(CH₃)=CH—
CH₂—CH(CN)—CO—OCH₃, —C(CH₃)—CH
—C)₂—CH(CN)—CO—OC₂H₅, —C(CH₃)=CH—
CH₂—CH(CH₃)—CO—OCH₃, —C(CH₃)=CH—
CH₂—CH(CH₃)—CO—OC₂H₅, —C(CH₃)=CH—
(CH₂)₂—CO—NH₂, —C(CH₃)=CH—(CH₂)₂—
CO—NH—CH₃, —C(CH₃)=CH—CH₂—COOH,
—C(CH₃)=CH—CH₂—CO—OCH₃, —C(CH₃)
=CH—CH₂—CO—OC₂H₅, —C(CH₃)=C
(COOCH₃)—CH₂—CO—OCH₃, —C(CH₃)=C
(COOCH₃)—CH₂—CO—OC₂H₅, —C(CH₃)=CH—
CH₂—CO—NH₂, —C(CH₃)=CH—CH₂—CO—
NH—CH₃, —C(CH₃)=CH—CH₂—CO—N(CH₃)₂, Compounds I in which $X^1$ and $X^2$ are each oxygen, $R^1$ is halogen, $R^2$ is hydrogen or fluorine, $R^3$ and $R^4$ are each $C_1$–$C_6$-alkyl or partially or completely halogenated $C_1$- or $C_2$-alkyl and $R^5$ is hydrogen, or $R^4$ and $R^5$ together form a tetramethylene chain, are very particularly preferred.

The substituted 3-phenyluracils are obtainable by various methods, preferably by one of the following processes:

a) Cyclization of an enamine ester of the formula II or of an enamine-carboxylate of the formula III

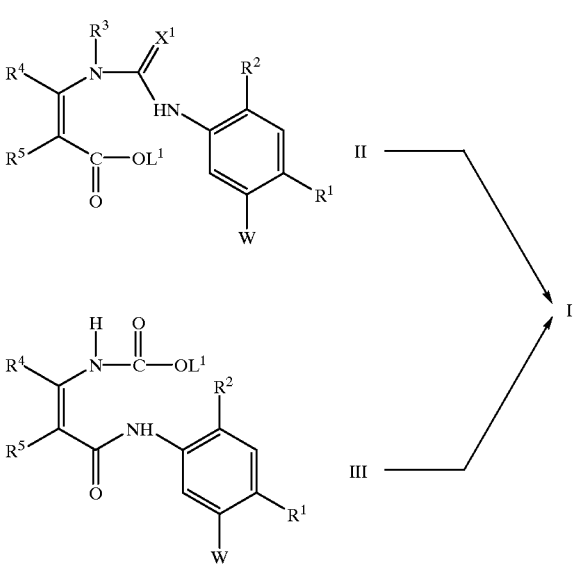

$L^1$ is low molecular weight alkyl, preferably $C_1$–$C_4$-alkyl, or phenyl.

As a rule, the reaction is carried out in an inert solvent or diluent, preferably in the presence of a base.

Suitable solvents or diluents are inert aprotic organic solvents, for example aliphatic or cyclic ethers, such as 1,2-dimethoxyethane, tetrahydrofuran and dioxane, aromatic hydrocarbons, such as benzene, toluene and xylenes, and inert polar organic solvents, such as dimethylformamide or dimethyl sulfoxide, or water, and the polar solvents may also be used as a mixture with a nonpolar hydrocarbon, such as n-hexane.

Preferred bases are alkali metal alcoholates, in particular sodium alcoholates, such as sodium methylate, and sodium ethylate, alkali metal hydroxides, in particular sodium hydroxide and potassium hydroxide, alkali metal carbonates, in particular sodium carbonate and potassium carbonate, and alkali metal hydrides, in particular sodium hydride.

When sodium hydride is used, the solvent is particularly preferably an aliphatic or cyclic ether, such as tetrahydrofuran, as well as dimethylformamide and dimethyl sulfoxide.

The amount of base is preferably from 0.5 to 2 times the molar amount, based on the amount of II or III.

In general, a reaction temperature of $-78°$ C. to the boiling point of the reaction mixture, in particular from $-60$ to $60°$ C., is advisable.

Depending on the nature of the base used, products I in which $R^3$ is hydrogen are present, after the cyclization, in the form of the corresponding metal salt of the general formula Ic

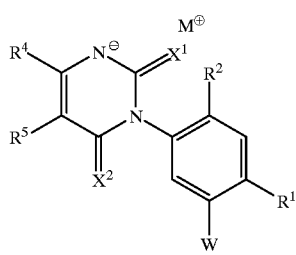

Ic ($M^\oplus$=one equivalent of a metal ion, in particular an alkali metal ion, such as sodium), for example in the form of the corresponding alkali metal salt in the case of the abovementioned preferred bases containing an alkali metal. The salt can be isolated and purified in a conventional manner, for example by recrystallization.

Products I in which $R^3$ is hydrogen are obtained by acidifying the reaction mixture obtained after the cyclization, for example with hydrochloric acid.

b) Alkylation or acylation of a substituted 3-phenyl-uracil I in which $R^3$ is hydrogen

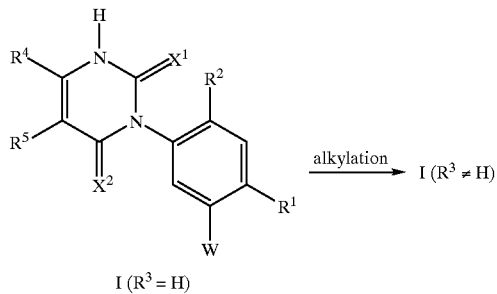

The alkylation is usually carried out with a halide, preferably with the chloride or bromide, or with the sulfate of an alkane, of an alkene, of an alkyne, of a cycloalkane, of a cyanoalkane, of a haloalkane, of a phenylalkane or of an alkoxyalkane.

Examples of suitable acylating agents are formyl halides, alkanecarbonyl halides or alkoxycarbonyl halides, the chlorides and bromides being preferred in each case.

The alkylation is advantageously carried out in the presence of an inert organic solvent and of a base, for example in a protic solvent, such as a lower alcohol, preferably ethanol, if necessary as a mixture with water, or in an aprotic solvent, such as an aliphatic or cyclic ether, preferably 1,2-dimethoxyethane, tetrahydrofuran or dioxane, an aliphatic ketone, preferably acetone, an amide, preferably dimethylformamide, or a sulfoxide, preferably dimethyl sulfoxide.

Examples of suitable bases are alcoholates, such as sodium methylate, sodium ethylate and potassium tert-butylate, hydroxides, such as sodium hydroxide, potassium hydroxide and calcium hydroxide, carbonates, such as sodium carbonate and potassium carbonate, and alkali metal hydrides, such as sodium hydride.

In a particularly preferred embodiment, the cyclization product (method a) present as a salt is alkylated without prior isolation from the reaction mixture, and in this case excess base, for example sodium hydride, a sodium alcoholate or sodium carbonate, originating from the cyclization of the compound II or III may also be present. However, this base has no adverse effect; if desired, a further amount of the diluent which was also used for the cyclization of the compound II or III may also be added.

The acylation with a halide can be carried out in a similar manner, the reaction particularly preferably being carried out in this case in an aprotic solvent and in the presence of sodium hydride as base.

The reaction temperature is in general from 0 to about $100°$ C., preferably from 0 to $40°$ C.

If they cannot be prepared directly by the cyclization under basic conditions, described as method a), the salts of the compounds I in which $R^3$ is hydrogen can also be obtained in a conventional manner from the products of the present method d). For this purpose, for example, the substituted 3-phenyluracil I in which $R^3$ is hydrogen is added to the aqueous solution of an inorganic or an organic base. The salt formation usually takes place at a sufficient rate at as low as $20$–$25°$ C.

It is particularly advantageous to prepare the sodium salt by dissolving the 3-phenyluracil I ($R^3$=hydrogen) in aqueous sodium hydroxide solution at $20$–$25°$ C., equivalent amounts of 3-phenyluracil and sodium hydroxide being used. The salt of the 3-phenyluracil can then be isolated, for example, by precipitation with a suitable inert solvent or by evaporating off the solvent.

Salts of the 3-phenyluracils whose metal ion is not an alkali metal ion can usually be prepared by double decomposition of the corresponding alkali metal salt in aqueous solution. Water-insoluble metal salts of 3-phenyluracil can generally be prepared in this manner.

c) Substitution of a halogen atom in the phenyl moiety of the substituted 3-phenyluracils I ($R^1$=halogen) by the cyano group

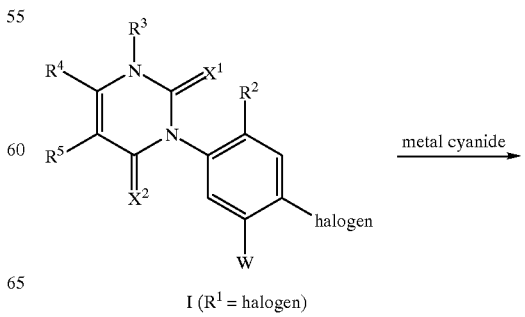

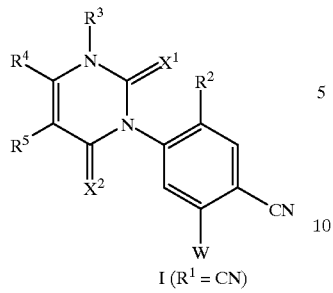

I (R¹ = CN)

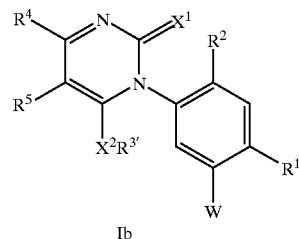

Ib

Hal is halogen, preferably chlorine or bromine.

The reaction is advantageously carried out in the presence of an aprotic, polar solvent, for example of an alkylnitrile, such as acetonitrile, propionitrile or butyronitrile, of an alkylurea such as N,N,N',N'-tetramethylurea, of a dialkylamide, such as dimethylformamide, or of a dialkyl sulfoxide, such as dimethyl sulfoxide, or in N-methyl-2-pyrrolidone, 1,2-dimethylimidazolidin-2-one, 1,2-dimethyl-3,4,5,6-tetrahydro-2(1H)-pyrimidinone or hexamethylphosphorotriamide.

The reaction is usually carried out using a metal cyanide, in particular a transition metal cyanide, such as copper(I) cyanide, at elevated temperatures, preferably at from 150 to 250° C.

The starting materials are advantageously used in stoichiometric amounts, but an excess of metal cyanide, for example up to 4 times the molar amount (based on the amount of starting material I in which $R^1$ is halogen), may also be advantageous.

d) Conversion of a pyrimidinone derivate of the formula IVa or IVb into an enol ether Ia or Ib

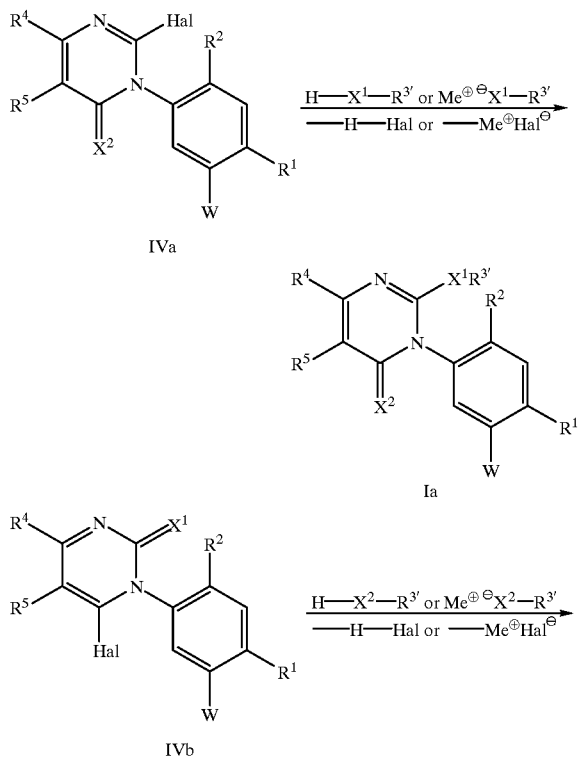

Hal is chlorine or bromine;

$Me^\oplus$ is one equivalent of a metal ion, in particular of a transition metal ion, of an alkali metal ion, such as sodium or potassium, or of an alkaline earth metal ion, such as potassium or magnesium.

Sodium is particularly preferred.

The reaction of the pyrimidinone derivatives IVa or IVb with alkanols, alkenols, alkynols ($R^{3'}$—OH) or alkanethiols, alkenethiols or alkynethiols ($R^{3'}$—SH) is advantageously carried out in the presence of an organic base, pyridine being particularly preferred.

The amount of base is not critical; usually, from 0.5 to 2 times the molar amount, based on the amount of IVa or IVb, is sufficient.

The reactions of IVa with H—$X^1$—$R^{3'}$ and of IVb with H—$X^2$—$R^3$ can be carried out either in the absence of a solvent in an excess of $R^{3'}$—OH or $R^{3'}$—SH or in a suitable inert organic solvent, for example in an aromatic, such as toluene or xylene, in an ether, such as diethyl ether, tetrahydrofuran or 1,2-dimethoxyethane, or in a halo-hydrocarbon, such as dichloromethane or chlorobenzene.

When the compound $R^{3'}$—OH is used, the reaction is preferably carried out in the absence of a solvent, using from 1 to about 150 times the amount, based on the amount of pyrimidinone derivative IVa or IVb, of $R^{3'}$—OH.

In the reaction with a salt of the formula $M^\oplus {}^\ominus O$—$R^{3'}$ or $M^\oplus {}^\ominus S$—$R^{3'}$, it is advisable to use equimolar amounts of pyrimidinone derivative and salt, but an excess of the salt of up to about 20 mol % (based on the amount of pyrimidinone derivative) may also be advantageous.

A reaction temperature of from 0 to 50° C., preferably from 10 to 30° C., is usually sufficient.

e) Acetalation of a compound I in which W is —C(=O)—$R^8$

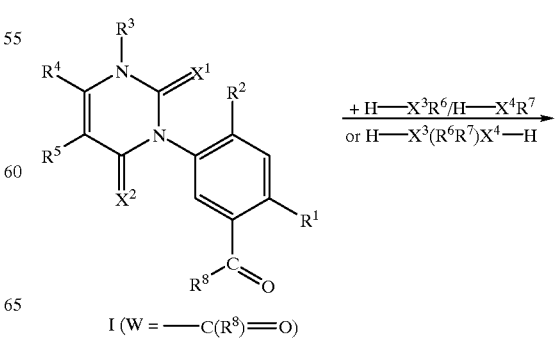

I (W = —C($R^8$)=O)

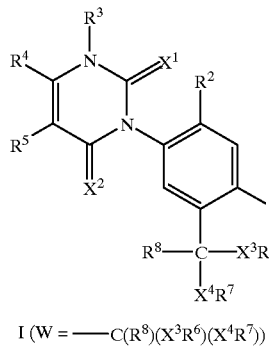

I (W = ——C(R⁸)(X³R⁶)(X⁴R⁷))

The acetalation is generally carried out in an inert aprotic organic solvent, for example in an aliphatic or cyclic ether, such as diethyl ether, 1,2-dimethoxyethane, tetrahydrofuran or dioxane, in an aromatic hydrocarbon, such as benzene or toluene, o-, m- or p-xylene or mesitylene, or in a chlorohydrocarbon, such as methylene chloride, chloroform or chlorobenzene, unless it is effected in the absence of a solvent in an excess of H—X³R⁶, H—X⁴R⁷ or H—X³(R⁶R⁷)X⁴—H.

Any water of reaction formed can be removed in a conventional manner from the reaction mixture, for example by means of a water separator.

The acetalation is preferably carried out in the presence of an organic acid, such as p-toluenesulfonic acid, and/or of a Lewis acid, such as tin tetrachloride, tin(II) chloride, iron (III) chloride, tellurium tetra-chloride or boron trifluoroetherate, or of a suitable catalyst, such as montmorillonite K10, the amount of acid usually being from 0.5 to 100 mol %, based on the amount of starting material to be acetalated.

The ratios are not critical. For complete conversion, all reactants are used in about a stoichiometric ratio, but an excess of H—X³R⁶ and H—X⁴R⁷ or H—X³(R⁶R⁷)X⁴—H is preferably used.

If the starting materials H—X³R₆ and H—X⁴R⁷ or H—X³(R⁶R⁷)X⁴—H are used simultaneously as diluents, they are present in a larger excess.

The reactions are carried out in general at from −78 to 180° C., preferably from −40 to 150° C.

If product mixtures are obtained, for example when R⁶ and R⁷ do not form a common radical and X³R⁶ and X⁴R⁷ are not identical, they can, if desired, be purified and separated by conventional methods, such as crystallization and chromatography.

In particular, compounds of the formula I where W is —C(R⁸)(X³R⁶)(X⁴R⁷), R⁶ and R⁷ do not form a common radical and X³R⁶ and X⁴R⁷ are not identical can also be prepared by other methods known from the literature (cf. for example Tetrahedron Lett. 32 (1991), 467–470, and the literature cited there).

In some cases it may also be advantageous to carry out the acetalation via the circuitous route of acetalation to give the dialkyl acetal, preferably dimethyl acetal, and subsequent transacetalation in the presence of a suitable catalyst. The solvents used for the transacetalation, the catalysts and other reaction conditions correspond to those already mentioned above for the acetalation.

A further novel variant is the reaction of a compound I (W=CHO) with a reactive derivative R²C(X³R⁶)(X⁴R⁷) under transacetalation conditions (for conditions see above). Examples of suitable reactive derivatives are acetals and ortho-esters.

f) Acetal cleavage of a compound I in which W is —C(R⁸)(X³R⁶)(X⁴R⁷)

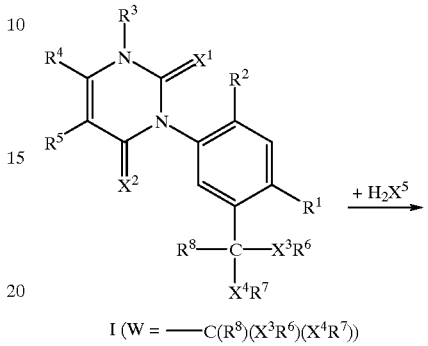

I (W = ——C(R⁸)(X³R⁶)(X⁴R⁷))

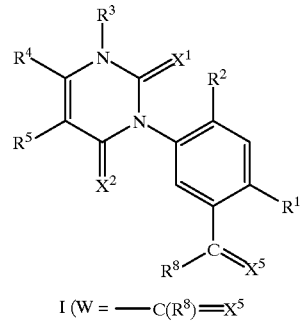

I (W = ——C(R⁸)=X⁵)

The acetal cleavage can be carried out without the addition of an acid, in the presence of an acid, for example of a mineral acid, such as hydrochloric acid and sulfuric acid, or of an organic carboxylic acid, such as formic acid, acetic acid, oxalic acid or trifluoroacetic acid, in the presence of an acidic ion exchanger, such as Amberlite® (trade mark of Aldrich) IR120 or IRC84, or in the presence of a transition metal salt, such as mercury(II) oxide, copper(I) oxide or iron(III) chloride.

Examples of suitable solvents or diluents are aromatics, such as benzene, toluene and o-, m- and p-xylene, aliphatic or cyclic ethers, such as 1,2-dimethoxyethane, diethyl ether, tetrahydrofuran and dioxane, alcohols, such as methanol, ethanol and iso-propanol, polar organic solvents, such as dimethylformamide, dimethyl sulfoxide and acetonitrile, ketones, such as acetone and butanone, and water.

The reaction is preferably carried out in the absence of a solvent in an excess of the acid used for the acetal cleavage, formic acid being particularly preferred.

For complete conversion, the starting materials I, in which W is —C(R⁸)(X³R⁶)(X⁴R⁷), and H₂X⁵ are used in at least a stoichiometric ratio, but an excess of H₂X⁵ of up to about 200 mol % is also possible.

The amount of acid, ion exchanger or transition metal salt is not critical. In general, up to about 300 mol %, based on the amount of H₂X⁵, is sufficient.

As a rule, the reaction temperature is from −78 to 180° C., preferably from 0° C. to the boiling point of the particular diluent.

Further methods which can be used for the preparation of the substituted 3-phenyluracils I are described in Houben-Weyl, Handbuch der Org. Chemie, 4th Edition, Vol. $E_3$, page 362 et seq.

g) Olefination of compounds I (W=—$C(R^8)$=O)

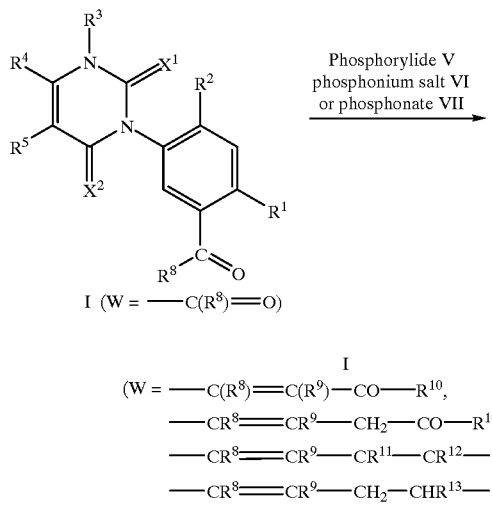

Phosphorylide V
phosphonium salt VI
or phosphonate VII

I (W = —$C(R^8)$=O)

I
(W = —$C(R^8)$=$C(R^9)$—CO—$R^{10}$,
—$CR^8$=$CR^9$—$CH_2$—CO—$R^{10}$,
—$CR^8$=$CR^9$—$CR^{11}$—$CR^{12}$—CO—$R^{10}$
—$CR^8$=$CR^9$—$CH_2$—$CHR^{13}$—CO—$R^{10}$)

The reaction can be carried out using the following phosphorylides Va to Vd, phosphonium salts VIa to VId and phosphonates VIIa to VIId:

| Phos-phorylides V: | $R^3P$ = $C(R^9)$—CO—$R^{10}$ | | Va, |
|---|---|---|---|
| | $R^3P$ = $C(R^9)$—$CH_2$—CO—$R^{10}$ | | Vb, |
| | $R^3P$ = $C(R^9)$—$C(R^{11})$—$C(R^{12})$—CO—$R^{10}$ | | Vc, |
| | $R^3P$ = $C(R^9)$—$CH_2$—$CH(R^{13})$—CO—$R^{10}$ | | Vd; |
| Phosphonium salts VI: | $R_3P^\oplus$—$CH(R^9)$—CO—$R^{10}$ | $Hal^\ominus$ | VIa, |
| | $R_3P^\oplus$—$CH(R^9)$—$CH_2$—CO—$R^{10}$ | $Hal^\ominus$ | VIb, |
| | $R_3P^\oplus$—$CH(R^9)$—$CR^{11}$=$CR^{12}$—CO—$R^{10}$ | $Hal^\ominus$ | VIc, |
| | $R_3P^\oplus$—$CH(R^9)$—$CH_2$—$CHR^{13}$—CO—$R^{10}$ | $Hal^\ominus$ | VId; |
| Phosphonates VII: | $(RO)_2PO$—$CH(R^9)$—CO—$R^{10}$ | | VIIa, |
| | $(RO)_2PO$—$CH(R^9)$—$CH_2$—CO—$R^{10}$ | | VIIb, |
| | $(RO)_2PO$—$CH(R^9)$—$CR^{11}$ = $CR^{12}$—CO—$R^{10}$ | | VIIc, |
| | $(RO)_2PO$—$CH(R^9)$—$CH_2$—$CHR^{13}$—CO—$R^{10}$ | | VIId. |

Those phosphorylides Vb and Vd, phosphonium salts VIb and VId and phosphonates VIIb and VIId in which $R^{10}$ is hydrogen, alkyl or cycloalkyl are not very suitable.

The radicals R on the phosphorus may be identical or different and are, for example, branched or straight-chain $C_1$–$C_8$-alkyl, $C_5$- or $C_6$-cycloalkyl and in particular phenyl which may carry further substituents which are inert for the reaction, for example $C_1$–$C_4$-alkyl, such as methyl, ethyl or tert-butyl, $C_1$–$C_4$-alkoxy, such as methoxy, or halogen, such as fluorine, chlorine or bromine. Unsubstituted phenyl radicals are preferred since the starting material triphenylphosphine used for the preparation of the phosphorylides V and phosphonium salts VI is particularly economical and furthermore the very unreactive, solid triphenylphosphine oxide which can be readily separated off is formed in the reactions.

For example, the methods described in Houben-Weyl, Methoden der Organischen Chemie, Volume E2, 1982, page 345 et seq. are suitable for the preparation of the phosphonates VII.

Suitable solvents are inert organic solvents, for example aromatics, such as toluene and o-, m- and p-xylene, ethers, such as 1,2-dimethoxyethane, diethyl ether, tetrahydrofuran and dioxane, polar organic solvents, such as dimethylformamide and dimethyl sulfoxide, or alcohols, such as methanol, ethanol and isopropanol.

In the olefination of I where W is —$C(R^8)$=O with a phosphonium salt VI or a phosphonate VII, the reaction is carried out in the presence of a base, alkali metal alkyls, such as n-butyllithium, alkali metal hydrides and alcoholates, such as sodium hydride, sodium ethylate and potassium tert-butylate, and alkali metal and alkaline earth metal hydroxides, such as calcium hydroxide, being particularly suitable.

For complete conversion, all reactants are used in about a stoichiometric ratio, but an excess of base of about 10 mol % is preferably used.

In general, the reaction temperature is from –40 to 150° C.

The compounds of the formulae V, VI and VII are known or can be prepared by known methods (cf. for example Houben-Weyl, Methoden d. Org. Chemie, Vol. E1, page 636 et seq., Georg Thieme Verlag, Stuttgart, 1982, ibid. Vol. E2, page 345 et seq. and Chem. Ber. 95 (1962), 3993).

A further possibility for the preparation of 3-phenyluracils I where W is —$CR^8$=$CR^9$—CO—$R^{10}$ and $R^{10}$ is hydrogen, alkyl, alkenyl, haloalkyl, cycloalkyl, phenyl or alkoxyalkyl is the conventional aldol condensation. Suitable conditions for this purpose are described in, for example, Nielsen, Org. React. 16 (1968), 1 et seq.

Suitable further methods for synthesizing compounds of the formula I where W is —$C(R^8)$=$C(R^9)$—CO—$R^{10}$, —$CH(R^8)$=CH ($R^9$)—CO—$R^{10}$, —$CR^8$=$CR^{11}$—$CH_2$—CO—$R^{12}$, —$CR^8CR^{11}$—$CR^{13}$=$CR^{14}$—CO—$R^{10}$ or —$CR^8$=$CR^{11}$—$CH_2$—$CHR^{15}$—CO—$R^{12}$, and $R^9$ or $R^{11}$ is hydrogen, cyano, alkoxycarbonyl or alkylcarbonyl are both the Knoevenagel condensation and the Perkin condensation. Suitable conditions are described in, for example, Org. React. 15 (1967), 204 et seq. (Knoevenagel) or Johnson, Org. React. 1 (1942), 210 et seq. (Perkin).

Compounds in which $R^{10}$ is —$NR^{18}R^{19}$ or —$SR^{17}$ can be prepared, for example, in a conventional manner by converting compounds in which $R^{10}$ is hydroxyl into the corresponding acyl halides ($R^{10}$ is halogen) and subsequently reacting the products with a corresponding amine H—$NR^{18}R^{19}$ or thiol H—$SR^{17}$ or with a reactive derivative of these compounds.

h) Reaction of compounds I (W=—$C(R^8)$=O) with amines, hydroxylamines or hydrazines

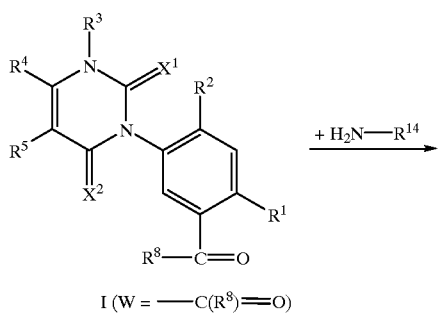

I (W = —C(R$^8$)=O)

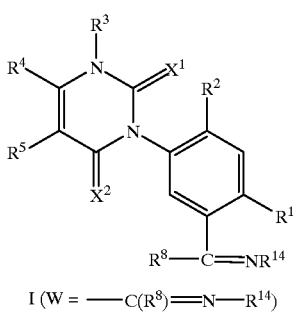

I (W = —C(R$^8$)=N—R$^{14}$)

The reaction is usually carried out in an inert organic solvent or diluent, for example in an aromatic, such as toluene or xylene, in a chlorohydrocarbon, such as dichloromethane, chloroform or chlorobenzene, in an ether, such as diethyl ether, 1,2-dimethoxyethane or tetrahydrofuran, in an alcohol, such as methanol or ethanol, or in a mixture of the stated solvents.

If the amines H$_2$N—R$^{14}$ are in the form of salts, for example as hydrochlorides or oxalates, the addition of a base, preferably sodium carbonate, potassium carbonate, sodium bicarbonate, triethylamine or pyridine, is preferable for their liberation.

The resulting water of reaction can, if desired, be removed from the reaction mixture by distillation or with the aid of a water separator.

The reaction temperature is usually from −30 to 150° C., preferably from 0 to 130° C.

i) Cleavage of compounds I where W is —C(R$^8$)=N—R$^{14}$

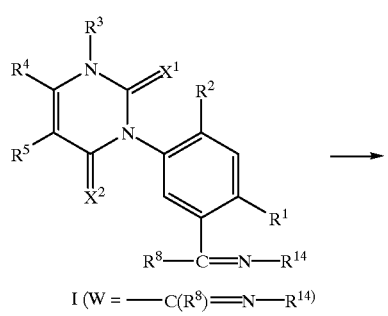

I (W = —C(R$^8$)=N—R$^{14}$)

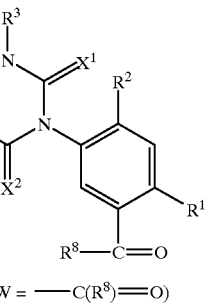

I (W = —C(R$^8$)=O)

The cleavage reaction is carried out in the absence of a solvent or in an inert solvent or diluent with water or a reactive derivative of water.

The reaction can be carried out by hydrolysis or under oxidative conditions, a reaction temperature of from −78 to 180° C., preferably from 0° C. to the boiling point of the diluent being preferable.

Examples of suitable solvents or diluents are aromatics, such as benzene, toluene and o-, m- and p-xylene, chlorinated hydrocarbons, such as dichloro-methane, chloroform and chlorobenzene, ethers, such as dialkyl ether, 1,2-dimethoxyethane, tetrahydrofuran and dioxane, alcohols, such as methanol and ethanol, ketones, such as acetone, esters of organic acids, such as ethyl acetate, or water and mixtures of the stated solvents.

The reaction is advantageously carried out in the presence of a mineral acid, such as hydrochloric acid, hydrobromic acid or sulfuric acid, of a carboxylic acid, such as acetic acid or trifluoroacetic acid, or of a sulfonic acid, such as p-toluenesulfonic acid.

To trap the H$_2$N—R$^{14}$ obtained in the hydrolysis or to remove it from the equilibrium, it may be advantageous to carry out the reaction in the presence of another carbonyl compound, for example acetone, formaldehyde, glyoxylic acid or phenylglyoxylic acid, preferably formaldehyde, which forms a more stable compound with H$_2$N—R$^{14}$ than I (W=CHO).

In the procedure under oxidative conditions, oxidizing agents such as lead tetraacetate, sodium hypochloride and hydrogen peroxide are particularly suitable.

If desired, the reaction may additionally be carried out in the presence of a catalyst, such as copper(II) sulfate, titanium tetrachloride or boron trifluoroetherate.

The amounts of acid, oxidizing agent and catalyst may be varied within wide limits. Usually, both the amount of acid and the amount of catalyst are from 5 to 200 mol % and the amount of oxidizing agent is from 25 to 400 mol %, based on the amount of the compound to be oxidized, but they may also be used in a considerably larger excess.

k) Reaction of a substituted 3-phenyluracil I in which X$^2$ is oxygen with a sulfurization reagent

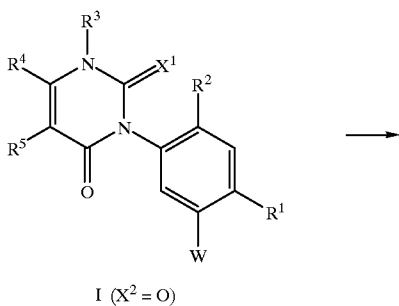

I (X² = O)

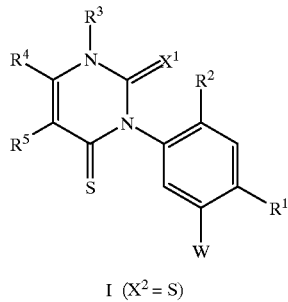

I (X² = S)

The reaction is carried out as a rule in an inert solvent, for example in an aromatic hydrocarbon, such as toluene or o-, m- or p-xylene, in an ether, such as diethyl ether, 1,2-dimethoxyethane or tetrahydrofuran, or in an organic amine, such as pyridine.

Particularly suitable sulfurization reagents are phosphorus (V) sulfide and 2,4-bis-(4-methoxyphenyl)-1,3,2,4-dithiadiphosphetane-2,4-dithione (Lawesson's reagent).

The amount of sulfurization reagent is not critical; from 1 to 5 times the molar amount, based on the 3-phenyluracil to be sulfurized, is usually used.

The reaction temperature is usually from 20 to 200° C., preferably from 40° C. to the boiling point of the solvent.

l) Halogenation of a substituted 3-phenyluracil I in which $R^5$ is hydrogen

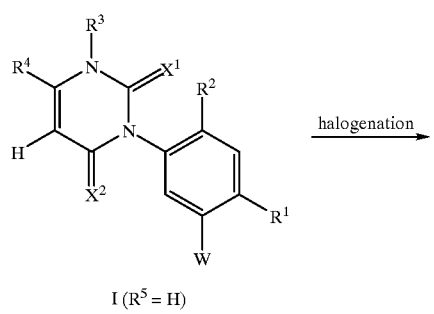

I ($R^5$ = H)

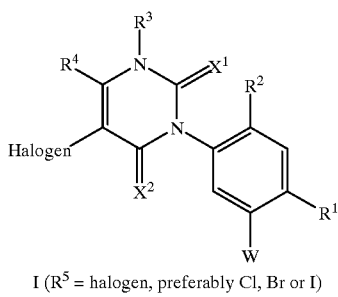

I ($R^5$ = halogen, preferably Cl, Br or I)

The halogenation is carried out as a rule in an inert organic solvent or diluent. For example, aliphatic carboxylic acids, such as acetic acid, or chlorinated aliphatic hydrocarbons, such as methylene chloride, chloroform and carbon tetrachloride, are suitable for the chlorination and bromination. Low boiling aliphatic carboxylic acids, such as acetic acid, are particularly preferred for the iodination.

Elemental chlorine or bromine and sulfuryl chloride or sulfuryl bromide are particularly suitable for the chlorination and bromination, a reaction temperature of from 0 to 60° C., preferably from 10 to 30° C., being preferable.

If desired, the chlorination and bromination can be carried out in the presence of an acid acceptor, sodium acetate and tertiary amines, such as triethylamine, dimethylaniline and pyridine, being particularly preferred.

Elemental iodine is a particularly preferred iodinating agent, and in this case the reaction temperature is from 0 to 110° C., preferably from 10 to 30° C.

The iodination is particularly advantageously carried out in the presence of a mineral acid, such as fuming nitric acid.

The amount of halogenating agent is not critical; equimolar amounts of halogenating agent or an excess of up to about 200 mol %, based on the starting material to be halogenated, are usually used.

Excess iodine can be removed by means of saturated aqueous sodium bisulfite solution, for example after the reaction.

m) Reduction of a substituted 3-phenyluracil I in which W is cyano

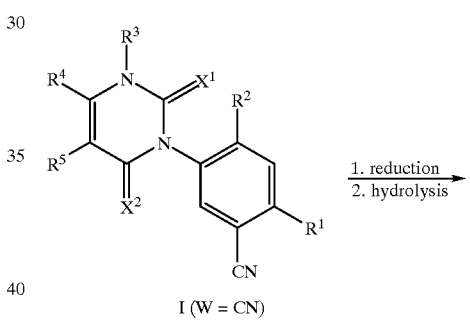

I (W = CN)

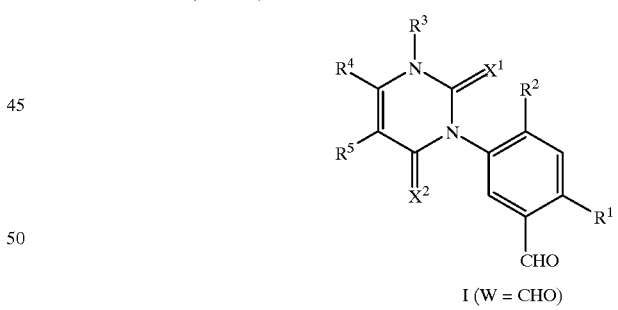

I (W = CHO)

The reaction is advantageously carried out in an inert organic solvent, for example an aromatic, such as toluene or o-, m- or p-xylene, an aliphatic or cyclic ether, such as diethyl ether, tert-butyl methyl ether, tetrahydrofuran or dioxane, a chlorohydrocarbon, such as methylene chloride, chloroform or chlorobenzene, or in an organic carboxylic acid, such as formic acid.

Examples of suitable reducing agents are hydrogen or metal salts, such as tin(II) chloride, metal hydrides, such as diisobutylaluminum hydride, diisopropylaluminum hyride, lithiumtrisethoxyaluminum hydride and lithiumbisethoxyaluminum hyride, or triethylsilane. Diisobutylaluminum hydride, formic acid or hydrogen is preferably used.

If desired, the reduction can be carried out in the presence of a catalyst, such as triethyloxonium tetrafluoroborate or Raney nickel.

If the reaction is carried out in the absence of a diluent in formic acid as a reducing agent, the latter may also be present in a relatively large excess.

The most advantageous reaction temperature is dependent on the particular reducing agent but is in general from −78 to 150° C.

n) Phosgenation or thiophosgenation of an enamine amide of the formula VIII

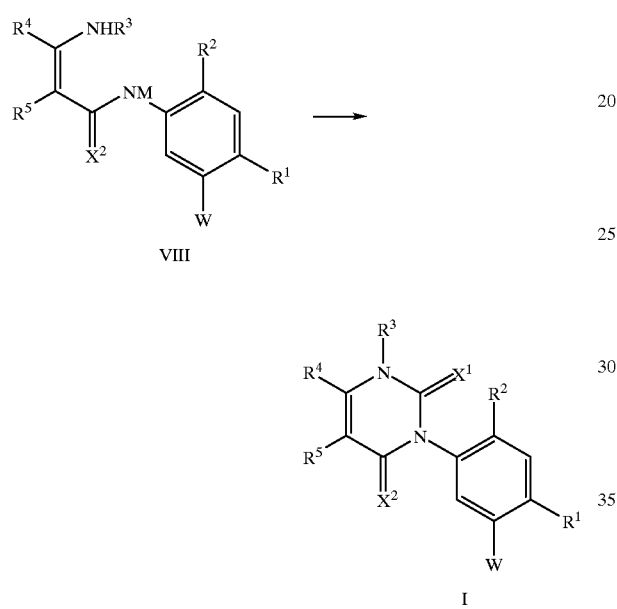

The process can be carried out in an inert organic solvent with the aid of a suitable phosgenating or thiophosgenating agent, eg. phosgene, thiophosgene, trichloromethyl chloroformate or 1,1'-carbonyl-diimidazole, in the presence or absence of a base, such as an organic nitrogen base, eg. triethylamine, pyridine or 2,6-lutidine, at from −20 to 130° C., preferably from 0° C. to the reflux temperature of the solvent used.

Particularly suitable solvents or diluents are aprotic, organic solvents, for example aromatics, such as toluene and o-, m- and p-xylene, halohydrocarbons, such as methylene chloride, chloroform, 1,2-dichloroethane and chlorobenzene, aliphatic or cyclic ethers, such as 1,2-dimethoxyethane, tetrahydrofuran and dioxane, or esters, such as ethyl acetate, and, particularly where $X^1$ is sulfur, water, as well as mixtures of these solvents.

The amount of the phosgenating or thiophosgenating agent is not critical and is usually from 0.9 to 1.3 times the molar amount (based on VIII), but may also be substantially higher (200–500 mol %) in certain cases.

o) Meerwein alkylation of a diazonium salt IXb

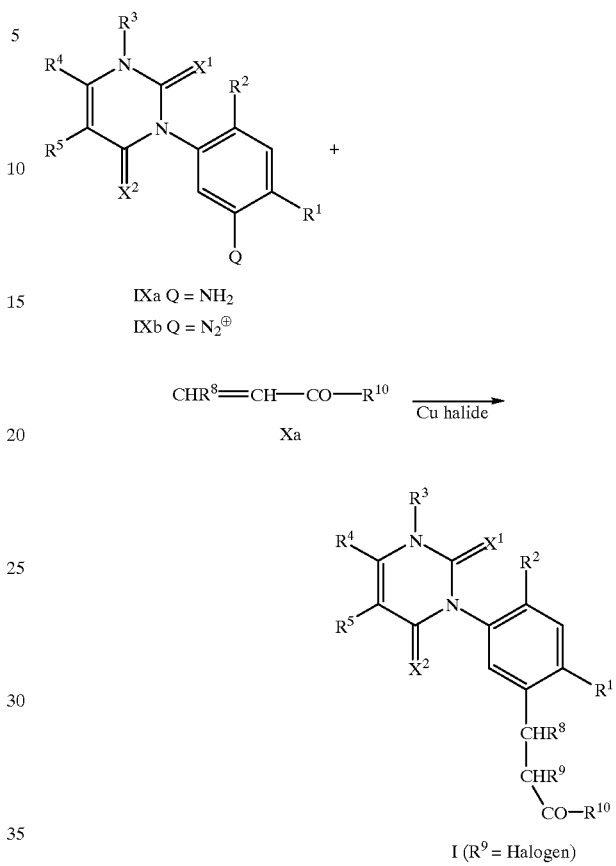

The reaction conditions of the Meerwein reaction are known to the skilled worker (cf. for example M. P. Doyle et al., J. Org. Chem. 42 (1977), 2431; G. Theodoridis et al., J. Heterocyclic Chem. 28 (1991), 849; C. S. Rondestvedt Jr., Org. React. 24 (1976), 225 and the literature cited there) and can be applied to the novel compounds I in analogy to the compounds described in the literature.

p) Metal-catalyzed olefin coupling with a phenyl halide the formula IXc

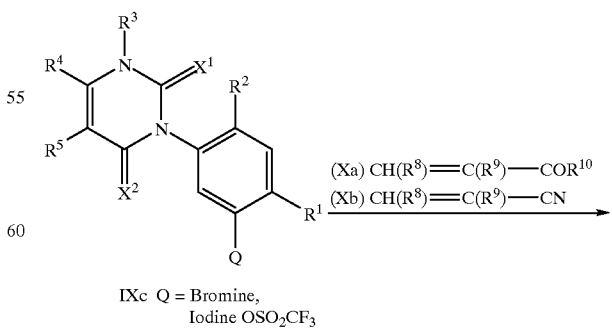

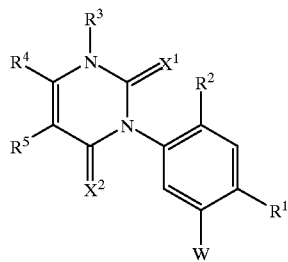

I where W = (C(R$^8$)=C(R$^9$)—COR$^{10}$
        (C(R$^8$)=C(R$^9$)—CN

The conditions of this Heck or Heck-like reaction are known to the skilled worker and can be applied to the novel compounds I in analogy to the compounds described in the literature (cf. for example Comprehensive Organic Chemistry).

The enamine esters of the formula II which are required as starting materials are novel unless W is —CH=CH—CO—OR$^{14}$ where R$^{14}$ is $C_1$–$C_6$-alkyl or $C_3$–$C_6$-alkenyl when R$^4$ is trifluoromethyl and R$^5$ is hydrogen (cf. U.S. Pat. No. 4,979,982). They can likewise be used as herbicides.

The enamine esters II can be prepared by known methods, for example by one of the following processes:

q)

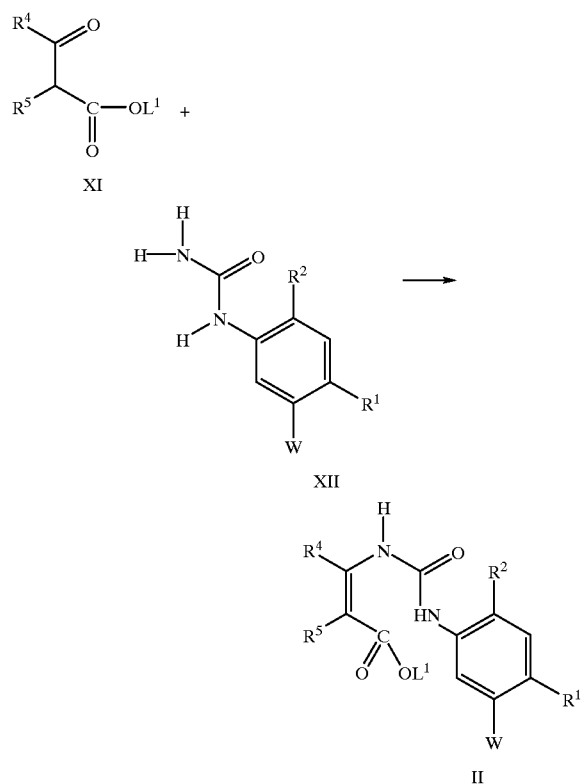

The reaction is preferably carried out under essentially anhydrous conditions in an inert solvent or diluent, particularly preferably in the presence of an acidic or basic catalyst.

Particularly suitable solvents or diluents are organic solvents which form an azeotropic mixture with water, for example aromatics, such as benzene, toluene and o-, m- and p-xylene, halohydrocarbons, such as methylene chloride, chloroform, carbon tetrachloride and chlorobenzene, aliphatic and cyclic ethers, such as 1,2-dimethoxyethane, tetrahydrofuran and dioxane, or cyclohexane, as well as alcohols, such as methanol and ethanol.

Preferred acidic catalysts are strong mineral acids, such as sulfuric acid and hydrochloric acid, phosphorus-containing acids, such as orthophosphoric acid and polyphosphoric acid, organic acids, such as p-toluenesulfonic acid, and acidic cation exchangers, such as Amberlyst 15 (Fluka).

Examples of suitable basic catalysts are metal hydrides, such as sodium hydride, and particularly preferably metal alcoholates, such as sodium methylate and ethylate.

The β-ketoester XI and the phenylurea XII are advantageously used in a stoichiometric ratio, or a slight excess of up to 10 mol % of one or other component is used.

From 0.5 to 100 mol %, based on the amount of a starting material, of a catalyst is usually sufficient.

In general, the reaction is carried out at from 60 to 120° C., or preferably at the boiling point of the reaction mixture for rapid removal of water formed.

r)

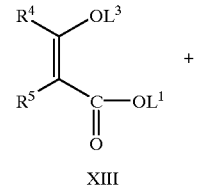

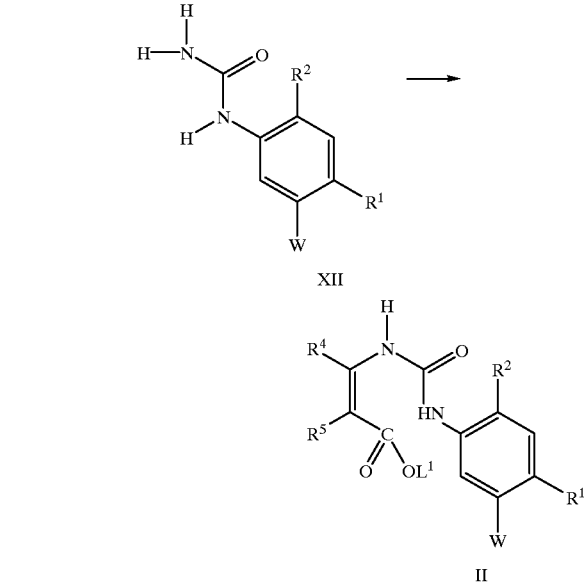

$L^3$ is $C_1$–$C_4$-alkyl or phenyl.

This reaction can be carried out, for example, in an inert, water-miscible, organic solvent, for example an aliphatic or cyclic ether, such as diethyl ether, 1,2-dimethoxyethane, tetrahydrofuran or dioxane, or a lower alcohol, in particular ethanol, the reaction temperature usually being from 50 to 150° C., preferably the boiling point of the reaction mixture.

The reaction can, however, also be carried out in an aromatic diluent, such as benzene, toluene or o-, m- or p-xylene, in which case the addition of either an acidic catalyst, such as hydrochloric acid or p-toluene-sulfonic acid, or of a base, for example of an alkali metal alcoholate, such as sodium methylate and sodium ethylate, is preferable. In this process variant too, the reaction temperature is usually from 50 to 150° C., preferably from 60 to 80° C.

s)

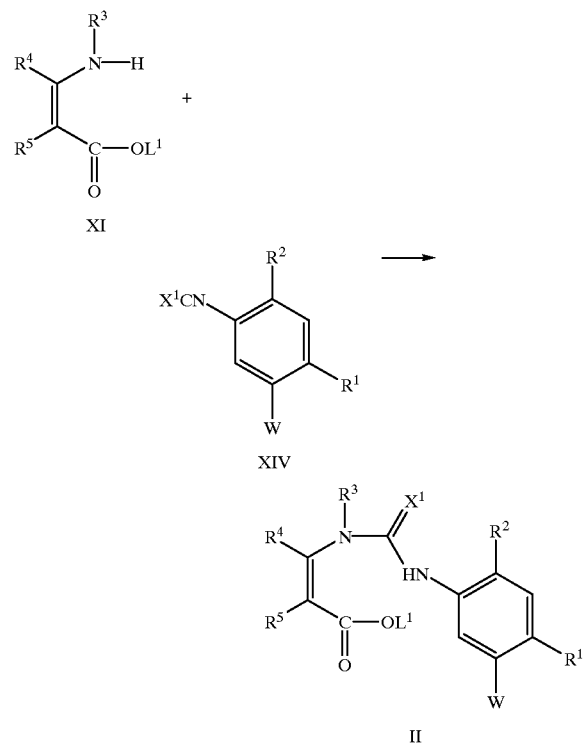

t)

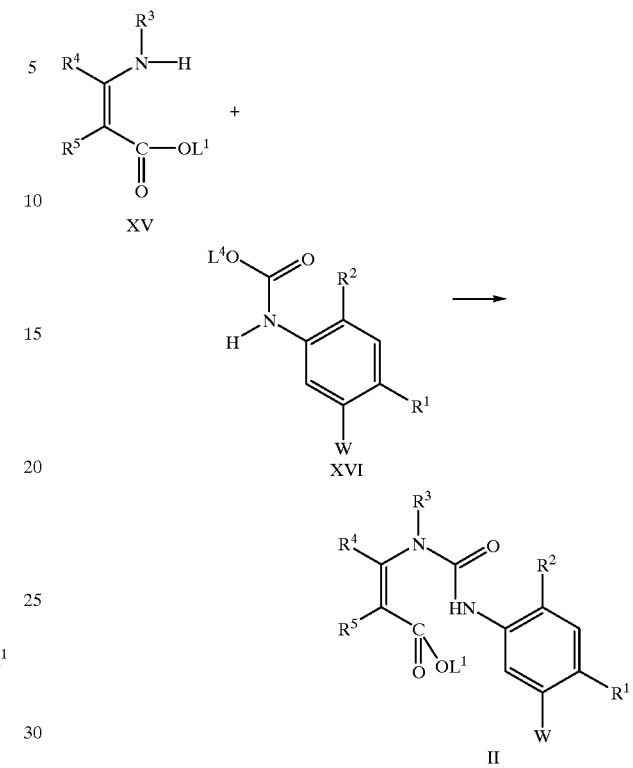

The reaction is advantageously carried out in the presence of an essentially anhydrous, aprotic, organic solvent or diluent, for example of an aliphatic or cyclic ether, such as diethyl ether, 1,2-dimethoxyethane, tetrahydrofuran or dioxane, of an aliphatic or aromatic hydrocarbon, such as n-hexane, benzene, toluene or o-, m- or p-xylene, of a halogenated, aliphatic hydrocarbon, such as methylene chloride, chloroform, carbon tetrachloride, 1,2-dichloroethane or chlorobenzene, of an aprotic, polar solvent, such as dimethylformamide, hexamethylphosphorotriamide or dimethyl sulfoxide, or of a mixture of the stated solvents.

If desired, the reaction can also be carried out in the presence of a metal hydride base, such as sodium hydride or potassium hydride, of an alkali metal or alkaline earth metal alcoholate, such as sodium methylate, sodium ethylate or potassium tert-butylate, or of an organic tertiary base, such as triethylamine or pyridine, and the organic base may simultaneously serve as a solvent.

The starting materials are advantageously used in a stoichiometric ratio, or a slight excess of up to about 20 mol % of one or other component is used. If the reaction is carried out in the absence of a solvent and in the presence of an organic base, the latter is present in a relatively large excess.

The reaction temperature is preferably from −80 to 50° C., particularly preferably from −60 to 30° C.

In a particularly preferred variant of this process, the II obtained is converted with excess base directly (ie. in situ) into the corresponding compound I by process variant a).

Byproducts which may occur (for example C-alkylation products in the case of compounds in which $R^5$ is hydrogen) can be removed by conventional separation methods such as crystallization and chromatography.

$L^1$ and $L^4$ are each $C_1$–$C_4$-alkyl or phenyl.

This reaction is advantageously carried out in an aprotic, polar solvent or diluent, such as dimethylformamide, 2-butanone, dimethyl sulfoxide or acetonitrile, and advantageously in the presence of a base, for example of an alkali metal or alkaline earth metal alcoholate, in particular of a sodium alkanolate, such as sodium methylate, of an alkali metal or alkaline earth metal carbonate, in particular sodium carbonate, or of an alkali metal hydride, such as lithium hydride or sodium hydride.

Usually, from 1 to 2 times the molar amount, based on the amount of starting material, of base is sufficient.

The reaction temperature is in general from 80 to 180° C., preferably the boiling point of the reaction mixture.

Regarding the ratios of the starting materials, the statements made for method q) are applicable.

In a particularly preferred embodiment, a sodium alcoholate is used as the base, and the alcohol formed in the course of the reaction is distilled off continuously. The enamine esters of the formula II prepared in this manner can be cyclized to a salt of the substituted 3-phenyluracils I by process variant a) without isolation from the reaction mixture.

u)

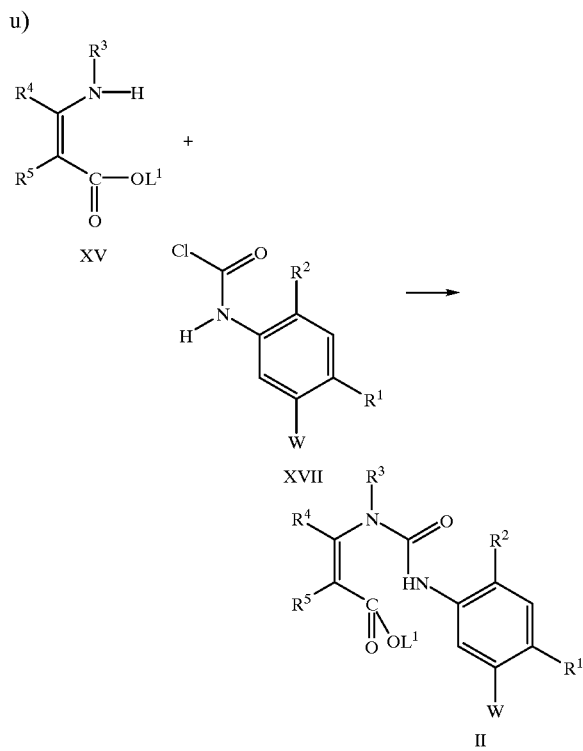

This reaction is advantageously carried out in the presence of an essentially anhydrous, aprotic, organic solvent or diluent, if desired in the presence of a metal hydride base, such as sodium hydride and potassium hydride, or of an organic tertiary base, such as triethylamine or pyridine, and the organic base may also serve as the solvent.

Regarding the suitable solvents and ratios, the statements made for method r) are applicable.

The reaction temperature is as a rule from −80 to 150° C., preferably from −60° C. to the particular boiling point of the solvent.

v)

The reaction is advantageously carried out in the presence of an essentially anhydrous, aprotic organic solvent or diluent, for example of an aliphatic or cyclic ether, such as diethyl ether, 1,2-dimethoxyethane, tetrahydrofuran and dioxane, of an aliphatic or aromatic hydrocarbon, such as n-hexane, benzene, toluene or o-, m- or p-xylene, of a halogenated, aliphatic hydrocarbon, such as methylene chloride, chloroform, carbon tetrachloride, 1,2-dichloroethane or chlorobenzene, of an aprotic, polar solvent, such as dimethylformamide, hexamethylphosphorotriamide or dimethyl sulfoxide, or of a mixture of the stated solvents.

If desired, the reaction may also be carried out in the presence of a metal hydride base, such as sodium hydride or potassium hydride, of an alkali metal or alkaline earth metal alcoholate, such as sodium methylate, sodium ethylate or potassium tert-butylate, or of an organic tertiary base, such as triethylamine or pyridine, and the organic base may simultaneously serve as the solvent.

The starting materials are advantageously used in a stoichiometric ratio, or a slight excess of up to about 20 mol % of one or other component is used. If the reaction is carried out in the absence of a solvent and in the presence of an organic base, the latter is present in a relatively large excess.

The reaction temperature is preferably from −80 to 150° C., particularly preferably from −30 to the reflux temperature of the solvent used.

The enamine-carboxylates of the formula III are likewise novel and can be used as herbicides. They can be prepared by conventional processes, for example from an aniline derivative of the formula XVI according to the following reaction scheme:

(G12)

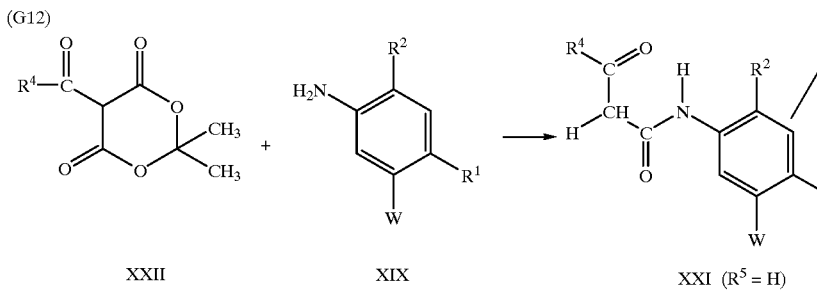

(G13)

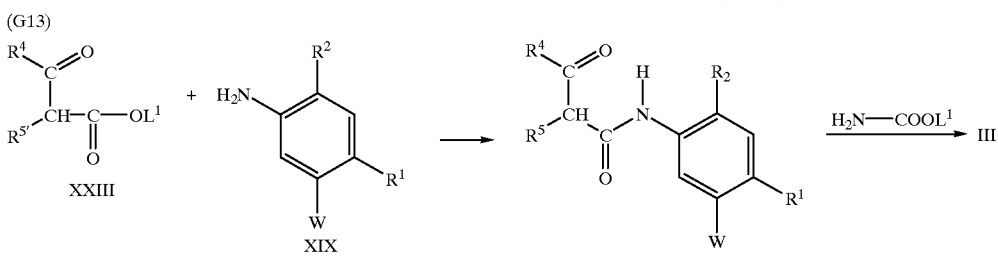

In equation (G11), $R^{4'}$ and $R^{5'}$ are each hydrogen or $C_1$–$C_4$-alkyl.

The reactions according to equations 1 and 2 are preferably carried out in an anhydrous inert aprotic solvent, for example in a halohydrocarbon, such as methylene chloride, chloroform, carbon tetrachloride or chlorobenzene, an aromatic hydrocarbon, such as benzene, toluene or o-, m- or p-xylene, or an aliphatic or cyclic ether, such as diethyl ether, dibutyl ether, 1,2-dimethoxyethane, tetrahydrofuran and dioxane.

For the reaction of the lactone XX with the aniline derivative XIX according to equation (G11), it is preferable to add a basic catalyst, eg. 4-pyrrolidinopyridine, 4-dimethylaminopyridine, 1,2-diazabicyclo-[2.2.2]octane, 1,5-diazabicyclo[4.3.0]non-5-ene, 1,8-diazabicyclo[5.4.0]undec-7-ene or diethylamine.

Since the reaction is exothermic, a reaction temperature of from –10 to 50° C., preferably from 10 to 30° C., is generally sufficient.

For the reaction of the compounds of the formulae XXII and XIX with one another according to equation (G12), on the other hand, higher temperatures, for example from 70 to 140° C., in particular from 100 to 120° C., are advantageous.

The reaction according to equation (G13) is an aminolysis, which, as a rule, is carried out either in the absence of a solvent [cf. for example J. Soc. Dyes Col. 42 (1926), 81, Ber. 64 (1931), 970; Org. Synth., Coll. Vol. IV (1963), 80 and J. Am. Chem. Soc. 70 (1948), 2402] or in an inert anhydrous solvent or diluent, in partiuclar in an aprotic solvent, for example in an aromatic or haloaromatic, such as toluene, o-, m- or p-xylene or chlorobenzene.

It is advisable here to carry out the reaction in the presence of a basic catalyst, for example of a relatively high boiling amine [cf. for example Helv. Chim. Acta 11 (1928), 779 and U.S. Pat. No. 2,416,738] or pyridine.

The reaction temperature is preferably from about 20 to 160° C.

In all three preparation variants, the starting materials are advantageously used in a stoichiometric ratio, or a slight excess of up to about 10 mol % of one or other component is used. If the reaction is carried out in the presence of a basic catalyst, from 0.5 to 200 mol %, based on the amount of a starting material, is generally sufficient.

The subsequent reaction of the resulting compounds of the formula XXI with the compound $H_2N$—$COOL^1$ is advantageously carried out in a substantially anhydrous solvent or diluent at atmospheric pressure, particularly preferably in the presence of an acidic catalyst.

Particularly suitable solvents or diluents are organic liquids which form azeotropic mixtures with water, for example aromatics, such as benzene, toluene and o-, m- and p-xylene, and halohydrocarbons, such as carbon tetrachloride and chlorobenzene.

Particularly suitable catalysts are strong mineral acids, such as sulfuric acid, organic acids, such as p-toluenesulfonic acid, phosphorus-containing acids, such as orthophosphoric acid and polyphosphoric acid, and acidic cation exchangers, such as Amberlyst 15 (Fluka).

In general, the reaction temperature is from about 70 to 150° C.; for rapid removal of the resulting water of reaction, however, the reaction is advantageously carried out at the boiling point of the solvent.

w) The pyrimidinone derivatives IVa and IVb, which are used as starting materials in method d), can be obtained by halogenation, preferably chlorination or bromination, of 3-phenyluracils I in which $R^3$ is hydrogen, in the absence of a solvent or in the presence of an inert solvent or diluent.

Particularly suitable solvents or diluents are aprotic organic liquids, for example aliphatic or aromatic hydrocarbons, such as n-hexane, benzene, toluene and o-, m- and p-xylene, halogenated aliphatic hydrocarbons, such as methylene chloride, chloroform and 1,2-dichloroethane, halogenated aromatic hydrocarbons, such as chlorobenzene, or tertiary amines, such as N,N-dimethylaniline.

Particularly suitable halogenating agents are thionyl chloride, phosphorus pentachloride, phosphoryl chloride, phosphorus pentabromide and phosphoryl bromide. A mixture of phosphorus pentachloride and phosphoryl chloride or of phosphorus pentabromide and phosphoryl bromide can also be particularly advantageous.

In most cases, it is preferable to add a catalytic amount of dimethylformamide or of an alkylated aniline derivative.

The amount of halogenating agent is not critical; for complete conversion, at least equimolar amounts of halogenating agent and of the educt to be halogenated are required. However, a 1-fold to 8-fold molar excess of halogenating agent may also be advantageous.

The reaction temperatures are in general from 0° C. to the reflux temperature of the reaction mixture, preferably from 20 to 120° C.

x) C-Acylation of an enamine of the formula XXIV with an isocyanate or isothiocyanate of the formula XII

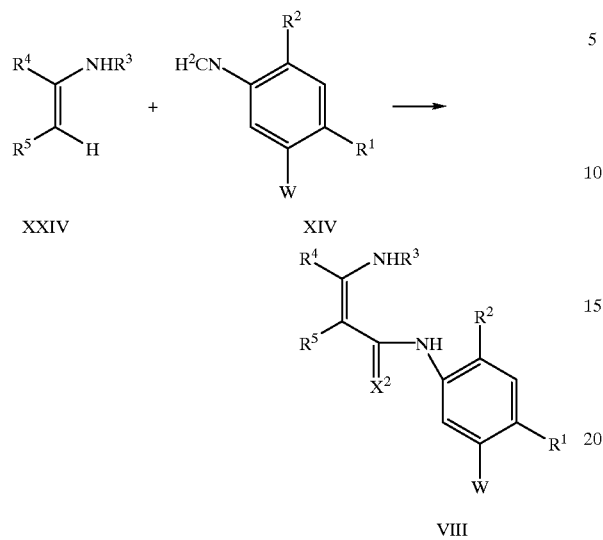

a) $L^3 = L^4 = H$
   $L^3$ or $L^4 \neq H$

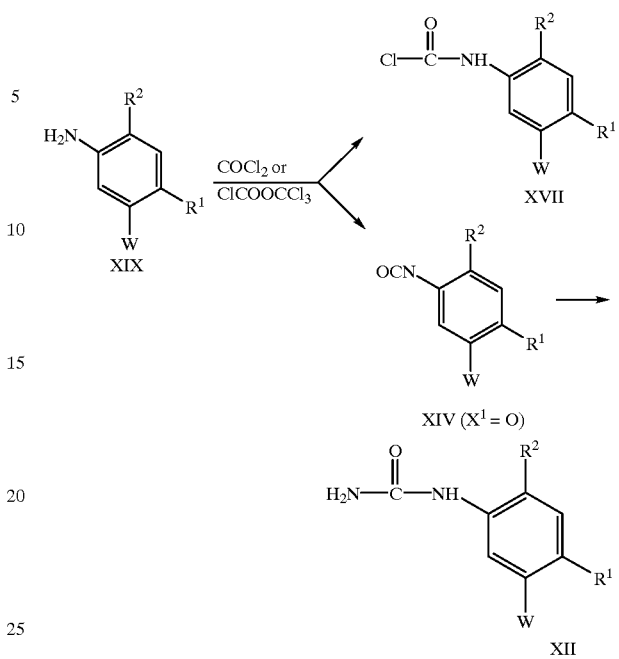

The reaction is advantageously carried out in the presence of an essentially anhydrous, aprotic organic solvent or diluent, for example of an aliphatic or cyclic ether, such as diethyl ether, 1,2-dimethoxyethane, tetrahydrofuran and dioxane, of an aliphatic or aromatic hydrocarbon, such as n-hexane, benzene, toluene or o-, m- or p-xylene, of a halogenated, aliphatic hydrocarbon, such as methylene chloride, chloroform, carbon tetrachloride, 1,2-dichloroethane or chlorobenzene, of an aprotic, polar solvent, such as dimethylformamide, hexamethylphosphorotriamide or dimethyl sulfoxide, or of a mixture of the stated solvents.

If desired, the reaction can also be carried out in the presence of an organic tertiary base, such as triethylamine or pyridine, and the organic base may simultaneously serve as the solvent.

The starting materials are advantageously used in a stoichiometric ratio, or a slight excess of up to about 20 mol % of one or other component is used. If the reaction is carried out in the absence of a solvent and in the presence of an organic base, the latter is present in a relatively large excess.

The reaction temperature is preferably from −80 to 150° C., particularly preferably from −30° C. to the reflux temperature of the solvent used.

The byproduct frequently obtained in this reaction (acylation at the nitrogen, cf. process variant s)) can be separated off in a conventional manner, for example by crystallization or chromatography.

The compounds of the formulae IX, XII, XIII and XIV are likewise novel. They can be prepared by conventional methods, particularly advantageously from compounds of the formula XVI:

By phosgenation and hydrolysis of the products with ammonia

The process can be carried out in an inert, essentially anhydrous solvent or diluent or in the absence of a solvent, the compounds XIX preferably being reacted with phosgene or trichloromethyl chloroformate.

Particularly suitable solvents or diluents are aprotic, organic solvents, for example aromatics, such as toluene and o-, m- and p-xylene, halohydrocarbons, such as methylene chloride, chloroform, 1,2-dichloroethane and chlorobenzene, aliphatic or cyclic ethers, such as 1,2-dimethoxyethane, tetrahydrofuran and dioxane, and esters, such as ethyl acetate, as well as mixtures of these solvents.

Depending on the aniline derivative XIX used, the addition of a base, such as triethylamine, may be advantageous, for example in from 0.5 to 2 times the molar amount, based on the amount of XIX.

By choosing suitable reaction conditions, both the carbamoyl chlorides XVII and the phenylisocyanates XIV can be obtained:

Thus, the carbamoyl chlorides XVII are usually obtained at low temperatures of from about −40 to 50° C., whereas a further increase in the temperature up to the boiling point of the reaction mixture leads predominantly to the formation of the phenylisocyanates XIV, which can be reacted with ammonia or with a reactive derivative of ammonia to give the phenylurea derivatives XII.

By reaction with alkali metal cyanates

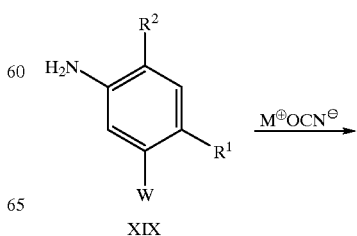

-continued

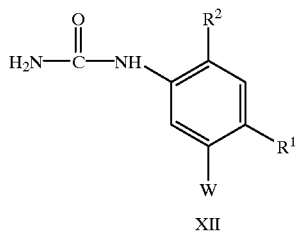

XII $M^\oplus$ is one equivalent of a metal ion, in particular an alkali metal ion, such as sodium or potassium.

The reaction is carried out in an inert solvent or diluent, for example in an aromatic hydrocarbon, such as toluene or o-, m- or p-toluene, in an aliphatic or cyclic ether, such as tetrahydrofuran or dioxane, in a lower alcohol, such as methanol or ethanol, in water or in a mixture of the stated solvents.

The amount of cyanate is not critical; at least equimolar amounts of aniline derivative XIX and cyanate are required for complete conversion, but an excess of cyanate of up to about 100 mol % may also be advantageous.

The reaction temperature is in general from 0° C. to the reflux temperature of the reaction mixture.

By reaction with esters XX

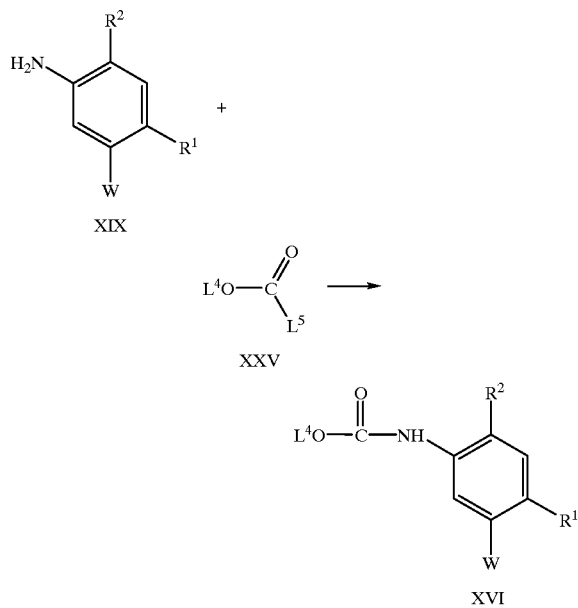

$L^4$ is $C_1$–$C_4$-alkyl or phenyl and $L^5$ is halogen, preferably chlorine or bromine, $C_1$–$C_4$-alkoxy or phenoxy.

Examples of suitable solvents or diluents are aromatic hydrocarbons, such as toluene and o-, m- and p-xylene, halohydrocarbons, such as methylene chloride, chloroform, 1,2-dichloroethane and chlorobenzene, aliphatic or cyclic ethers, such as 1,2-dimethoxyethane, tetrahydrofuran and dioxane, esters, such as ethyl acetate, alcohols, such as methanol and ethanol, and water or two-phase mixtures of an organic solvent and water.

The reaction is advantageously carried out in the presence of a base, for example of an alkali metal hydroxide, carbonate or alcoholate, such as sodium hydroxide, sodium carbonate, sodium methylate or sodium ethylate, or of a tertiary amine, such as pyridine or triethylamine.

If desired, a catalyst, for example a Lewis acid, such as antimony trichloride, may also be added.

The starting compounds and the base are advantageously used in a stoichiometric ratio, but one or other component may also be present in an excess of up to about 100 mol %.

As a rule, the amount of catalyst is from 1 to 50, preferably from 2 to 30, mol %, based on the amount of aniline derivative XIX used.

The reaction temperature is in general from –40° C. to the boiling point of the reaction mixture.

The starting compounds of the formula XIX and their preparation and all other compounds whose preparation is not described explicitly are known from the literature or said compounds can be prepared by conventional methods.

In the abovementioned processes for the synthesis of substituted 3-phenyluracils I, their salts, enol ethers or intermediates, atmospheric pressure or the autogenous pressure of the particular solvent is advantageously used. Lower or higher pressure is possible but usually has no advantages.

Unless stated otherwise, the reagents and starting materials required for the preparation of the substituted 3-phenyluracils I, Ia and Ib are known or can be prepared by conventional methods.

The particular reaction mixtures are worked up, as a rule, by conventional methods, for example by removing the solvent, distributing the residue in a mixture of water and a suitable organic solvent and isolating the product from the organic phase.

The substituted 3-phenyluracils I, Ia and Ib may be obtained in the preparation as isomer mixtures, which however can, if desired, be separated into the pure isomers by conventional methods, for example by crystallization or chromatography (if necessary, over an optically active adsorbate). Pure optically active isomers can be synthesized, for example, from corresponding optically active starting materials.

As a rule, the compounds of the formulae I, Ia and Ib can be prepared by the methods described above. However, in individual cases certain compounds I can also advantageously be prepared from other compounds I by ester hydrolysis, amidation, esterification, transetherification, esterification, ether cleavage, olefination, reduction, oxidation or a cyclization reaction at the positions of the radicals $R^4$, $R^5$ and W.

The substituted 3-phenyluracils I, Ia and Ib are suitable as herbicides both in the form of isomer mixtures and in the form of the pure isomers. In general they are well tolerated and therefore selective in broad-leaved crops and in monocotyledon plants.

Depending on the particular application method, the substituted phenyluracils Ia and Ib or the agents containing them can be used in a large number of crop plants for eliminating undesirable plants, the following crops being mentioned as examples:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Beta vulgaris spp. altissima* | sugarbeets |
| *Beta vulgaris spp. rapa* | fodder beets |
| *Brassica napus var. napus* | rapeseed |
| *Brassica napus var. napobrassica* | swedes |
| *Brassica rapa var. silvestris* | beets |
| *Camellia sinensis* | tea plants |
| *Carthamus tinctorius* | safflower |
| *Carya illinoinensis* | pecan trees |

| Botanical name | Common name |
| --- | --- |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea eutopaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

The substituted 3-phenyluracils I, Ia and Ib are also suitable for the desiccation and defoliation of plants. As desiccants, they are particularly suitable for drying out the above-ground parts of crop plants, such as potatoes, rape, sunflower and soybean. This permits completely mechanical harvesting of these important crop plants.

Also of commercial interest is the facilitation of harvesting, which is permitted by concentrated dropping or a reduction in the adhesion to the tree in the case of citrus fruits, olives or other species and varieties of pomes, drupes and hard-shelled fruit. The same mechanism, ie. promotion of the formation of abscission tissue between the fruit or leaf part and the shoot part of the plant, is also essential for readily controllable defoliation of crops, for example cotton.

Furthermore, the shortening of the time interval in which the individual cotton plants ripen leads to higher fiber quality after harvesting.

Apart from their herbicidal and defoliant activity, some of the substituted 3-phenyluracils of the formuale I, Ia and Ib can also be used as growth regulators or for controlling pests from the class consisting of the insects, arachnids and nematodes. They can be used for controlling pests in crop protection and in the hygiene, stored materials and veterinary sectors.

The insect pests include, from the order of the butterflies (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis*;

from the order of the beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria*;

from the order of the Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae,*

*Phorbia coarctata, Rhagoletis cerasi, Rhagoletis pomonella, Tabanus bovinus, Tipula oleracea* and *Tipula paludosa;* from the order of the Thysanoptera, for example *Frankliniella fusca, Frankliniella occidentalis, Frankliniella tritici, Scirtothrips citri, Thrips oryzae, Thrips palmi* and *Thrips tabaci;* from the order of the Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta;* from the order of the Beteroptera, for example *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor;* from the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii;* from the order of the Isoptera, for example *Calotermes flavicollis, Leucotermes flavipes, Reticulitermes lucifugus* and *Termes natalensis;* from the order of the Orthoptera, for example *Acheta domestica, Blatta orientalis, Blatella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* from the class of the Arachnoidea, for example Acarina, such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae;* from the class of the nematodes, for example root gall nematodes, eg. *Meloidogyne hapla, Meloidogyne incognita* and *Meloidogyne javanica,* cyst-forming nematodes, eg. *Globodera rostochiensis, Heterodera avenae, Heterodera glycinae, Heterodera schatii, Heterodera trifolii,* and stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients can be used as such, in the form of their formulations or in the application forms prepared therefrom, for example in the form of directly sprayable solutions, powders, suspensions or dispersions, emulsions, oil dispersions, pastes, dusting agents, broadcasting agents or granules, by spraying, nebulizing, dusting, broadcasting and pouring. The application forms depend entirely on the intended uses; they should in any case ensure a very fine distribution of the novel active ingredients.

The formulations are prepared in a known manner, for example by extending the active ingredient with solvents and/or carriers, if desired with the use of emulsifiers and dispersants; where water is used as a diluent, other organic solvents may also be used as auxiliary solvents. Suitable inert assistants for this purpose are essentially mineral oil fractions having a medium to high boiling point, such as kerosene and diesel oil, as well as coal tar oils and oils with vegetable or animal origin, solvents, such as aromatics (eg. toluene or xylene), chlorinated aromatics (eg. chlorobenzenes), paraffins (eg. mineral oil fractions), alcohols (eg. methanol, ethanol, butanol or cyclohexanol), ketones (eg. cyclohexanone and isophorone), amines (eg. ethanolamine, N,N-dimethylformamide or N-methylpyrrolidone) and water; carriers such as ground natural minerals (eg. kaolins, aluminas, talc or chalk) and ground synthetic minerals (eg. finely divided silica or silicates); emulsifiers, such as nonionic and anionic emulsifiers (eg. polyoxyethylene fatty alcohol ethers, alkylsulfonates and arylsulfonates) and dispersants, such as ligninsulfite waste liquors and methylcellulose.

Aqueous application forms can be prepared from emulsion concentrates, dispersions, pastes, wettable powders or water-dispersible granules by adding water. For the preparation of emulsions, pastes or oil dispersions, the substrates, as such or dissolved in an oil or solvent, can be homogenized in water by means of wetting agents, adherents, dispersants or emulsifiers. However, concentrates which consist of active ingredient, wetting agents, adherents, dispersants or emulsifiers and possibly solvents or oil and which are suitable for dilution with water can also be prepared.

Suitable surfactants are alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkylsulfates, lauryl ether sulfates and fatty alcohol sulfates and salts of sulfated hexa-, hepta- and octadecanols, and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ethers, ethoxylated isooctyl-, octyl- or nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers or polyoxypropylene, lauryl alcohol polyglycol ether acetal, sorbitol esters, ligninsulfite waste liquors or methylcellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flours, bark meal, wood meal and nutshell meal, cellulosic powders and other solid carriers.

The concentrations of the active ingredients I, Ia and Ib in the ready-to-use formulations can be varied within wide ranges, for example from 0.0001 to 95% by weight. For use as herbicides or plant growth-regulating agents, concentrations of from 0.01 to 95, preferably from 0.5 to 90, % by weight of active ingredient are preferable. Formulations containing from 0.0001 to 10, preferably from 0.01 to 1, % by weight of active ingredient are suitable for use as insecticides. The active ingredients are used in a purity of from 90 to 100%, preferably from 95 to 100% (according to NMR spectrum).

Examples of such formulations are:

I. A solution of 90 parts by weight of compound No. 1.1 and 10 parts by weight of N-methyl-α-pyrrolidone, which is suitable for use in the form of very small drops.

II. A mixture of 20 parts by weight of compound No. 1.2, 80 parts by weight of xylene, 10 parts by weight of the adduct of 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By finely distributing the mixture in 100,000 parts by weight of water, a dispersion which contains 0.02% by weight of the active ingredient is obtained.

III. An aqueous dispersion of 20 parts by weight of compound No. 3.1, 40 parts by weight of cyclohexanone, 30 parts by weight of isobutanol and 20 parts by weight of the adduct of 40 mol of ethylene oxide with 1 mol of castor oil. The mixture of this dispersion with 100,000 parts by weight of water contains 0.02% by weight of the active ingredient.

IV. An aqueous dispersion of 20 parts by weight of compound No. 2.1, 25 parts by weight of cyclohexanol, 65 parts by weight of a mineral oil fraction boiling within a range of 210 to 280° C. and 10 parts by weight of the adduct of 40 mol of ethylene oxide with 1 mol of castor oil. The mixture of this dispersion with 100,000 parts by weight of water contains 0.02% of the active ingredient.

V. A mixture milled in a hammer mill and consisting of 80 parts by weight of compound No. 3.1, 3 parts by weight of the sodium salt of diisobutylnaphthalene-α-sulfonic acid, 10 parts by weight of the sodium salt of a ligninsulfonic acid obtained from a sulfite waste liquor and 7 parts by weight of silica gel powder. By finely distributing the mixture in 20,000 parts by weight of water, a spray liquor which contains 0.1% by weight of the active ingredient is obtained.

VI. An intimate mixture of 3 parts by weight of compound No. 3.2 and 97 parts by weight of finely divided kaolin. This dusting agent contains 3% by weight of active ingredient.

VII. An intimate mixture of 30 parts by weight of compound No. 3.3, 92 parts by weight of silica gel powder and 8 parts by weight of liquid paraffin which has been sprayed onto the surface of the silica gel. This formulation gives the active ingredient good adhesion.

VIII. A stable aqueous dispersion of 40 parts by weight of compound No. 4.1, 10 parts by weight of the sodium salt of a phenolsulfonic acid/urea/formaldehyde condensate, 2 parts by weight of silica gel and 48 parts by weight of water, which can be further diluted.

IX A stable oily dispersion of 20 parts by weight of compound No. 1.1, 2 parts by weight of the calcium salt of dodecylbenzenesulfonic acid, 8 parts by weight of a fatty alcohol polyglycol ether, 20 parts by weight of the sodium salt of a phenolsulfonic acid/urea/formaldehyde condensate and 68 parts by weight of a paraffinic mineral oil.

X. A mixture milled in a hammer mill and consisting of 10 parts by weight of compound No. 2.1, 4 parts by weight of the sodium salt of diisobutylnaphthalene-α-sulfonic acid, 20 parts by weight of the sodium salt of a ligninsulfonic acid obtained from a sulfite waste liquor, 38 parts by weight of silica gel and 38 parts by weight of kaolin. By finely distributing the mixture in 10,000 parts by weight of water, a spray liquor which contains 0.1% by weight of the active ingredient is obtained.

The active ingredients or the herbicidal and plant growth-regulating agents can be applied by the preemergence or postemergence method. The plants are usually sprayed or dusted with the active ingredients or the seeds of the test plants are treated with the active ingredients. If the active ingredients are less well tolerated by certain crop plants, it is possible to use application methods in which the herbicides are sprayed with the aid of the sprayers in such a way that the leaves of the sensitive crop plants are as far as possible not affected while the active ingredients reach the leaves of undesirable plants growing underneath or the uncovered oil surface (post-directed, lay-by).

The application rates of active ingredient are from 0.001 to 5.0, preferably from 0.01 to 2, kg/ha of active ingredient, depending on the aim of control, the season, the target plants and the stage of growth.

To broaden the action spectrum and to achieve synergistic effects, the substituted 3-phenyluracils I, Ia and Ib can be mixed and applied together with a large number of members of other groups of herbicidal or growth-regulating active ingredients. For example, diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry in the 2-position, for example, a carboxyl or carbimino, or quinolinecarboxylic acid derivatives, imidazolinones, sulfonamides, sulfonylureas, aryloxy- and hetaryloxyphenoxypropionic acids and their salts, esters and amides and others are suitable components for the mixture.

The substituted 3-phenyluracils I, Ia and Ib can also be applied together with other crop protection agents, such as herbicides, growth regulators, pesticides, fungicides and bactericides. These agents may be mixed with the novel agents in a weight ratio of from 1:100 to 100:1, if desired also directly before application (tank mix). Also of interest is the miscibility with mineral salt solutions which are used for eliminating nutrient and trace element deficiencies. Non-phytotoxic oils and oil concentrates may also be added.

PREPARATION EXAMPLES

Example 1

3-[4-Chloro-3-(ethoximinomethyl)-phenyl]-2,4-dioxo-6-trifluoromethyl-1,2,3,4-tetrahydropyrimidine (compound 1.4)

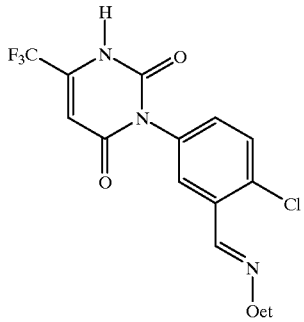

100.7 g of ethyl 3-amino-4,4,4-trifluorocrotonate in 150 ml of dimethylformamide were added dropwise to a suspension of 18.2 g of 80% strength sodium hydride in 550 ml of dimethylformamide at 0–5° C., and stirring was carried out for one hour at 0–5° C. Thereafter, 123.6 g of 4-chloro-3-ethoximinomethylphenyl isocyanate in 150 ml of tetrahydrofuran were added dropwise at from −30 to −35° C. and stirring was continued for 20 hours at 25° C. At 0–5° C., 1.7 l of water were stirred into the reaction mixture and the resulting precipitate was removed. The filtrate was brought to pH 5 with 60 ml of 6 N HCl and the precipitate which had separated out was isolated, washed with water and petroleum ether and dried.

mp.: 219–220° C.

Example 2

3-[4-Chloro-3-(ethoximinomethyl)-phenyl]-2,4-dioxo-6-methyl-1,2,3,4-tetrahydropyrimidine (compound 1.75)

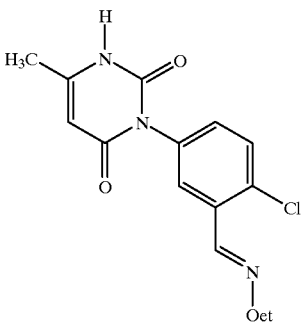

3 g of N-(4-chloro-3-ethoximinomethylphenyl)-N'-(1-ethoxycarbonylpropen-2-yl)-urea in 20 ml of dimethylformamide were added dropwise to a suspension of 0.24 g of 80% strength sodium hydride in 550 ml of dimethylformamide at room temperature, and stirring was carried out for 3 hours at room temperature. At 10–15° C., 100 ml of water were added, the pH was brought to 5 with 10% strength HCl and stirring was continued for 30 minutes at 10–15° C. The precipitate which had separated out was isolated, washed with water and dried.

mp.: >280° C.

Example 3

3-[4-Chloro-3-(ethoximinomethyl)-phenyl]-2,4-dioxo-1-methyl-6-trifluoromethyl-1,2,3,4-tetrahydropyrimidine (compound 1.5)

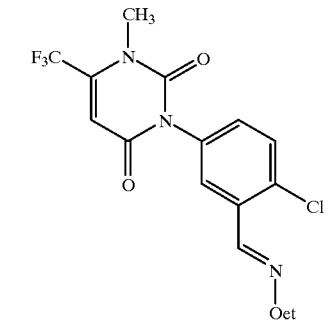

26.3 ml of methyl iodide in 100 ml of dimethylformamide were added dropwise, in the course of one hour, to a suspension of 137.5 g of 3-(4-chloro-3-ethoximinomethylphenyl)-2,4-dioxo-6-trifluoromethyl-1,2,3,4-tetrahydropyrimidine and 57.8 g of potassium carbonate in 600 ml of dimethylformamide, the temperature increasing to 30° C. After stirring had been carried out for 20 hours, 700 ml of water were added dropwise at 5–10° C. and the precipitate which had separated out was isolated, washed with water and petroleum ether and dried.

mp.: 133–134° C.

Example 4

3-(4-Chloro-3-formylphenyl)-2,4-dioxo-1-methyl-6-trifluoromethyl-1,2,3,4-tetrahydropyrimidine (compound 1.1)

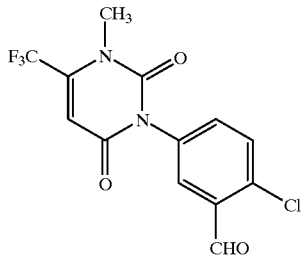

5 ml of water were added to a solution of 1.9 g of 3-(4-chloro-3-(1,3-dioxolan-2-yl)-phenyl)-2,4-dioxo-1-methyl-6-trifluoromethyl-1,2,3,4-tetrahydropyrimidine in 45 ml of glacial acetic acid. After stirring had been carried out for 12 hours at about 20–25° C. and for a further 5 hours at 40–50° C., 150 ml of water were stirred into the mixture. Thereafter, the precipitate formed was isolated, washed with water and petroleum ether and dried.

mp.: 151–153° C.

Example 5

3-[4-Chloro-6-fluoro-3-formylphenyl]-2,4-dioxo-1-methyl-6-trifluoromethyl-1,2,3,4-tetrahydropyrimidine (compound 1.67)

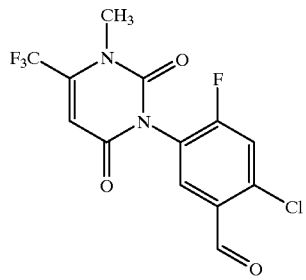

50 ml of concentrated hydrochloric acid and 50 ml of 37% strength formaldehyde solution were added to a solution of 58.5 g of 3-[4-chloro-6-fluoro-3-(ethoximinomethyl)-phenyl]-2,4-dioxo-1-methyl-6-trifluoromethyl-1,2,3,4-tetrahydropyrimidine in 350 ml of glacial acetic acid, and the mixture was refluxed for 2 hours. After cooling, the reaction mixture was evaporated down, the oily residue was stirred with water and the resulting crystalline precipitate was isolated, washed with water and petroleum ether and dried.

mp.: 172–174° C.

Example 6

3-[4-Chloro-3-(2-chloro-2-butoxycarbonylethen-1-yl)-phenyl]-2,4-dioxo-1-methyl-6-trifluoromethyl-1,2,3,4-tetrahydropyrimidine (compound 1.15)

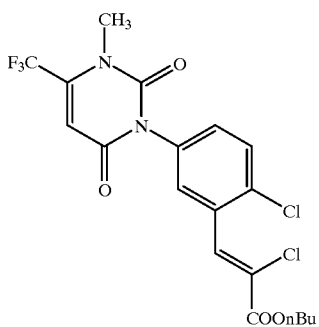

50 ml of a sodium n-butylate solution in n-butanol (prepared from 0.3 g of 80% strength sodium hydride and 50 ml of n-butanol) were added to a solution of 4.4 g of 3-[4-chloro-3-(2-chloro-2-ethoxycarbonylethen-1-yl)-phenyl]-2,4-dioxo-1-methyl-6-trifluoromethyl-1,2,3,4-tetrahydropyrimidine in 50 ml of n-butanol, and stirring was carried out for 5 hours at room temperature. Thereafter, the mixture was neutralized with 10% strength hydrochloric acid at 0–5° C. and the resulting solution was stirred into 100 ml of water at 0–5° C. The aqueous phase was extracted with 100 ml of toluene, and the combined organic phases were washed with three times 50 ml of water, dried over sodium sulfate and evaporated down. The oil obtained was chromatographed over silica gel (dichloromethane), and the oil obtained therefrom was stirred with petroleum ether. The resulting solid was filtered off, washed with petroleum ether and dried.

mp.: 109–110° C.

Example 7

3-[4-Chloro-3-(4-chloro-3-oxobut-1-enyl)-phenyl]-2,4-dioxo-1-methyl-6-trifluoromethyl-1,2,3,4-tetrahydropyrimidine (compound 1.29)

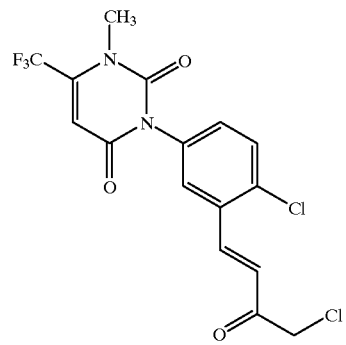

4.6 g of chloroacetylmethylenetriphenylphosphorane were added to a solution of 3.3 g of 3-[4-chloro-3-formylphenyl]-2,4-dioxo-1-methyl-6-trifluoromethyl-1,2,3,4-tetrahydropyrimidine in 100 ml of methanol, and stirring was carried out for 10 hours at room temperature. The precipitate which had separated out was isolated, washed with petroleum ether and dried.

mp.: 188–189° C.

Example 8

3-[4-Chloro-3-(2-cyanoethenyl)-phenyl]-2,4-dioxo-1-methyl-6-trifluoromethyl-1,2,3,4-tetrahydropyrimidine (compound 1.34)

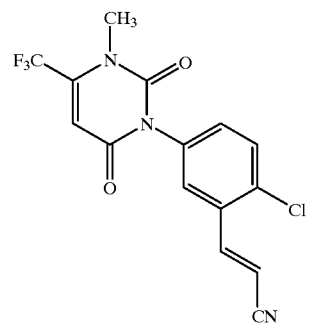

3.3 g of 3-(4-chloro-3-formylphenyl)-2,4-dioxo-1-methyl-6-trifluoromethyl-1,2,3,4-tetrahydropyrimidine in 30 ml of dimethylformamide were added dropwise to a suspension of 1.8 g of diethyl cyanomethylphosphonate and 1.5 g of potassium carbonate in 120 ml of dimethylformamide, and stirring was carried out for 20 hours at room temperature. Thereafter, 150 ml of water were added and the precipitate which had separated out was isolated, washed with water and petroleum ether and dried.

mp.: 263–265° C.

Example 9

3-[4-Chloro-3-(2-cyano-2-methoxycarbonylethenyl)-phenyl]-2,4-dioxo-1-methyl-6-trifluoromethyl-1,2,3,4-tetrahydropyrimidine (compound 1.22)

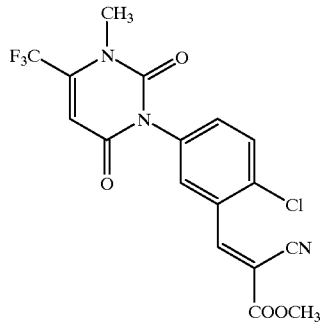

0.97 ml of methyl cyanoacetate and 0.3 ml of piperidine were added to a solution of 3.3 g of 3-(4-chloro-3-formylphenyl)-2,4-dioxo-1-methyl-6-trifluoromethyl-1,2,3,4-tetrahydropyrimidine in 100 ml of tetrahydrofuran. After the mixture had been stirred for 5 hours at the reflux temperature, a further 0.97 ml of methyl cyanoacetate was added and refluxing was continued for a further 5 hours. The reaction mixture was evaporated down and the oil obtained was chromatographed (dichloromethane). The solid obtained was stirred with diisopropyl ether, isolated, washed with petroleum ether and dried.

mp.: 187–188° C.

Example 10

5-Chloro-3-[4-chloro-(2-chloro-2-ethoxycarbonylethenyl)-phenyl]-2,4-dioxo-1-methyl-6-trifluoromethyl-1,2,3,4-tetrahydropyrimidine (sound 1.42)

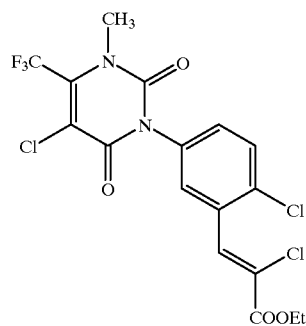

1.5 g of sulfuryl chloride were added dropwise to a solution of 4.4 g of 3-[4-chloro-3-(2-chloro-2-ethoxycarbonylethenyl)-phenyl]-2,4-dioxo-1-methyl-6-trifluoromethyl-1,2,3,4-tetrahydropyrimidine in 50 ml of glacial acetic acid. Stirring was carried out for 20 hours at room temperature and for 12 hours under reflux, a further 2.6 ml of sulfuryl chloride being added in two portions. The reaction mixture was evaporated down and stirred with water and the precipitate was isolated, washed with water and petroleum ether and dried.

mp.: 160–164° C.

Example 11

3-[4-Chloro-3-(2-(2,2,2-trifluoroethoxycarbonyl)-ethenyl)-phenyl]-2,4-dioxo-1-methyl-6-trifluoromethyl-1,2,3,4-tetrahydropyrimidine (compound 1.85)

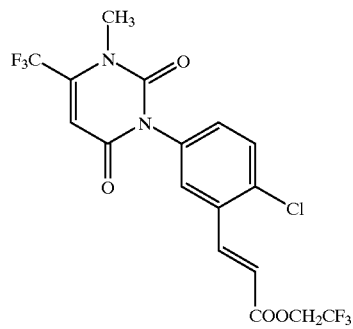

A suspension of 5.0 g of 3-[4-chloro-3-iodophenyl]-2,4-dioxo-1-methyl-6-trifluoromethyl-1,2,3,4-tetrahydropyrimidine, 2.0 g of 2,2,2-trifluoroethyl acrylate, 0.5 mg of palladium acetate and 1.1 g of sodium acetate in 50 ml of dimethylformamide was stirred for 4 hours at 120° C., after which further palladium acetate and 2,2,2-trifluoromethyl acrylate were added and stirring was continued for a further 2 hours at 120° C. The cooled reaction mixture was added to 200 ml of water and the precipitate was isolated, washed with petroleum ether and dried under greatly reduced pressure.

mp.: 170–172° C.

Example 12

3-[4-Chloro-3-(2-chloro-2-methoxycarbonylethyl]-phenyl- 2,4-dioxo-1-methyl-6-trifluoromethyl-1,2,3,4-tetrahydropyrimidine (compound 1.86)

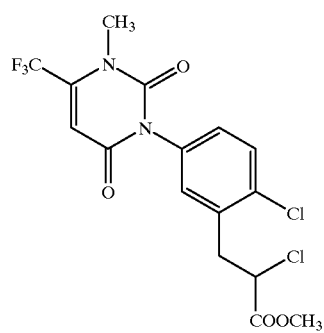

5.4 g of tert-butyl nitrite in 200 ml of acetonitrile were initially taken at 0° C. 30.1 g of methyl acrylate and 5.9 g of $CuCl_2$ were added in succession. Thereafter, a solution of 11.2 g of 3-[3-amino-4-chlorophenyl]-2,4-dioxo-1-methyl-6-trifluoromethyl-1,2,3,4-tetrahydropyrimidine in 100 ml of acetonitrile was slowly added dropwise and the mixture was stirred overnight at 25° C. For working up, the solvent was stripped off under reduced pressure and the residue was chromatographed over silica gel (8:1 cyclohexane/ethyl acetate). The title compound was obtained as an oil.

Example 13

3-[4-Chloro-3-(1,3-dioxan-2-yl)-phenyl]-2,4-dioxo-1-methyl-6-trifluoromethyl-1,2,3,4-tetrahydropyrimidine (compound 2.1)

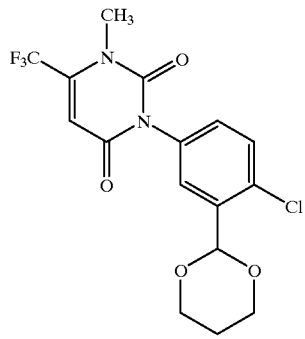

A solution of 3.5 g of 3-[4-chloro-3-formylphenyl]-2,4-dioxo-1-methyl-6-trifluoromethyl-1,2,3,4-tetrahydropyrimidine, 0.8 g of 1,3-propanediol and 0.2 g of p-toluenesulfonic acid in 100 ml of anhydrous dichloromethane was boiled for 5 hours under a water separator. The solution was washed with 10% strength sodium bicarbonate solution and water, dried over sodium sulfate and evaporated down. The residue was chromatographed over silica gel (7:3 cyclohexane/ethyl acetate).

mp.: 87–92° C.

Example 14

3-[4-Chloro-3-dimethoxymethylphenyl]-2,4-dioxo-1-methyl-6-trifluoromethyl-1,2,3,4-tetrahydropyrimidine (compound 2.22)

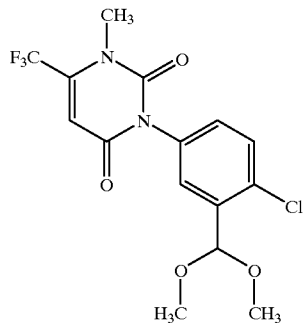

170 ml of trimethyl orthoformate were added to a thoroughly stirred suspension of 136 g of montmorillonite K10 in 700 ml of anhydrous toluene, and stirring was carried out for 30 minutes. Thereafter, 68.0 g of 3-(4-chloro-3-formylphenyl)-2,4-dioxo-1-methyl-6-trifluoromethyl-1,2,3,4-tetrahydropyrimidine were added dropwise while cooling with ice, and the batch was stirred overnight at 25° C. The montmorillonite K10 was filtered off and washed thoroughly with toluene. The solvent, excess ortho-ester and methyl formate were distilled off under reduced pressure from the combined filtrates. The remaining oil was crystallized with petroleum ether.

mp.: 92–94° C.

Example 15

3-[4-Chloro-3-(4,5-dimethyl-1,3-dioxolan-2-yl)-phenyl]-2,4-dioxo-1-methyl-6-trifluoromethyl-1,2,3,4-tetrahydropyrimidine (compound 2.17)

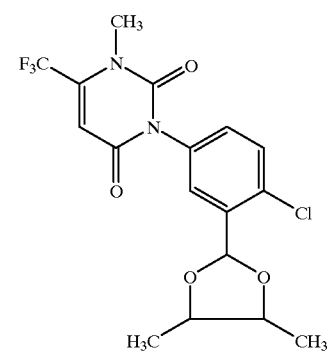

30 g of 3-(4-chloro-3-dimethoxymethylphenyl)-2,4-dioxo-1-methyl-6-trifluoromethyl-1,2,3,4-tetrahydropyrimidine, 2.1 g of 2,3-dihydroxybutane and 0.3 g of p-toluenesulfonic acid were dissolved in 100 ml of anhydrous toluene, and the stirred solution was refluxed for 7 hours in the absence of water. For working up, the solution was washed in succession with water and 10% strength $NaHCO_3$ solution, dried over $Na_2SO_4$ and evaporated down.

mp.: 149–151° C.

Example 16

3-[4-Chloro-3-(1,3-oxothiolan-2-yl)-phenyl]-2,4-dioxo-1-methyl-6-trifluoromethyl-1,2,3,4-tetrahydropyrimidine (compound 2.32)

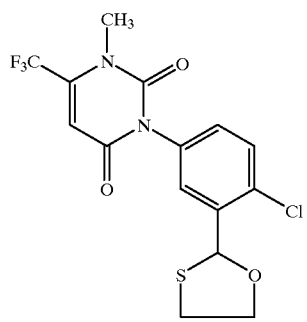

A mixture of 3.0 g of 3-(4-chloro-3-formylphenyl)-2,4-dioxo-1-methyl-6-trifluoromethyl-1,2,3,4-tetrahydropyrimidine, 0.8 g of 2-mercaptoethanol and 0.12 g of tellurium tetrachloride in 100 ml of 1,2-dichloroethane was stirred for 16 hours at room temperature. 0.2 g of sodium bicarbonate was added, the mixture was thoroughly stirred and the precipitate was filtered off and washed with dichloromethane. The combined organic filtrates were dried over sodium sulfate and evaporated down. The residue was chromatographed (diethyl ether) and was stirred in toluene/petroleum ether. The crystalline precipitate obtained was washed with petroleum ether and dried.

mp.: 168–170° C.

Example 17

3-[4-Chloro-3-(2-carboxy-2-chloroethenyl)-phenyl]-
2,4-dioxo-6-trifluoromethyl-1,2,3,4-
tetrahydropyrimidine (compound 1.41)

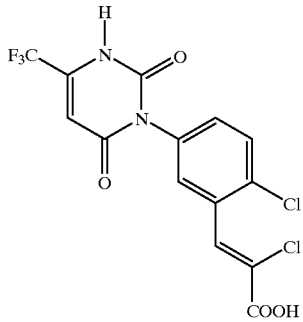

4.4 g of 3-[4-chloro-3-(2-chloro-2-ethoxycarbonylethenyl)-phenyl]-2,4-dioxo-6-trifluoromethyl-1,2,3,4-tetrahydropyrimidine were added to a suspension of 0.8 g of sodium hydroxide in 100 ml of ethanol and stirring was carried out for 20 hours at room temperature. The reaction mixture was evaporated down, the residue was taken up in water and the solution was brought to pH 3 with 10% strength HCl. The precipitate which had separated out was isolated, washed with water and petroleum ether and dried under reduced pressure.

mp.: >250° C.

Example 18

3-[4-Chloro-3-cyanomethoximinomethylphenyl]-2,
4-dioxo-1-methyl-6-trifluoromethyl-1,2,3,4-
tetrahydropyrimidine (compound 1.53)

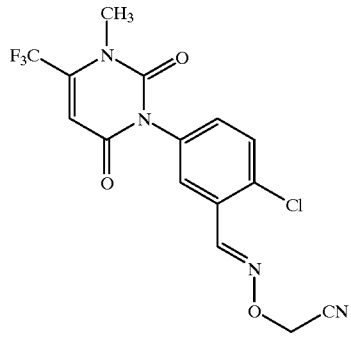

1.3 g of O-cyanomethylhydroxylamine hydrochloride were added to a suspension of 3.3 g of 3-(4-chloro-3-formylphenyl)-2,4-dioxo-1-methyl-6-trifluoromethyl-1,2,3,4-tetrahydropyrimidine and 1.3 g of sodium carbonate in 150 ml of toluene and stirring was carried out for 20 hours. The reaction mixture was washed with three times 50 ml of water, dried over sodium sulfate and evaporated down. The solid residue was stirred with petroleum ether, isolated, washed with petroleum ether and dried.

mp.: 171–174° C.

Example 19

3-[4-Chloro-3-(2-chloro-2-
methoxycarbonylethenyl)-phenyl]-2-methoxy-4-oxo-
6-trifluoromethyl-3,4-dihydropyrimidine (compound
3.1)

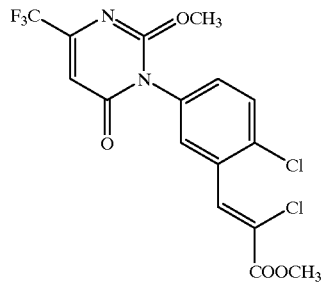

0.9 g of sodium methylate solution (30% strength in methanol) in 10 ml of methanol was added dropwise to a solution of 2.2 g of 2-chloro-3-[4-chloro-3-(2-chloroethoxycarbonylethenyl)-phenyl]-4-oxo-6-trifluoromethyl-3,4-dihydropyrimidine in 40 ml of methanol, and stirring was carried out for 2 hours at room temperature. The precipitate was isolated, washed with water and petroleum ether and dried.

mp.: 151–152° C.

Example 20

3-[4-Chloro-3-(2-chloro-2-ethoxycarbonylethenyl)-
phenyl]-4-oxo-2-thioxo-1,2,3,4-tetrahydrothieno[3,
4-d]pyrimidine (compound 1.90)

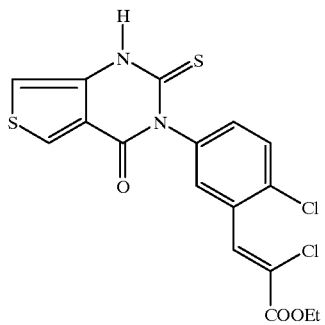

1.8 g of N-[4-chloro-3-(2-chloro-2-ethoxycarbonylethenyl)-phenyl]-N'-(4-methoxycarbonylthien-3-yl)-urea in 10 ml of dimethylformamide were added to a suspension of 0.11 g of sodium hydride (80% strength) in 50 ml of dimethylformamide at room temperature, and stirring was carried out for 3 hours at room temperature and for 8 hours at 50° C. The reaction mixture was cooled to 10–15° C., 100 ml of water were added, neutralization was effected with 10% strength hydrochloric acid and stirring was carried out for 1 hour. The precipitate obtained was isolated and was dissolved in dichloromethane. The solution obtained was washed twice with water, dried over sodium sulfate and evaporated down.

The residue was stirred with diisopropyl ether, isolated and dried.

mp.: 278–280° C.

Example 21

3-(4-Chloro-3-ethoxycarbonylhydrazonomethylphenyl)-2,4-dioxo-1-methyl-6-trifluoromethyl-1,2,3,4-tetrahydropyrimidine (compound 1.91)

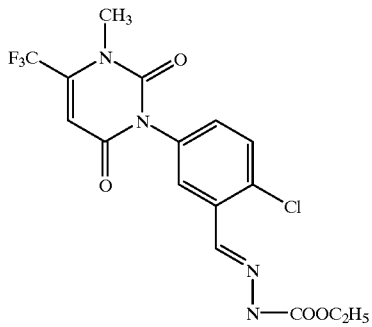

1.0 g of ethyl hydrazinecarboxylate was added to a solution of 3.3 g of 3-[4-chloro-3-formylphenyl]-2,4-dioxo-1-methyl-6-trifluoromethyl-1,2,3,4-tetrahydropyrimidine and 0.1 g of p-toluenesulfonic acid in 150 ml of toluene. After 2 hours, the solution was washed once with water, the organic phase was dried over sodium sulfate and evaporated down and the residue was stirred with petroleum ether. The precipitate was isolated, washed with petroleum ether and dried.

mp.: 111–116° C.

Example 22

3-[4-Chloro-3-(2-carboxy-2-chloroethenyl)-phenyl]-2,4-dioxo-1-methyl-6-trifluoromethyl-1,2,3,4-tetrahydropyrimidine (compound 1.92)

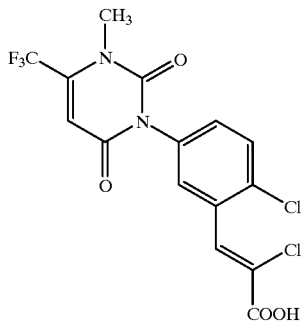

25 ml of trifluoroacetic acid were added to a solution of 4.7 g of 3-[4-chloro-3-(2-tert-butoxycarbonyl-2-chloroethenylphenyl]-2,4-dioxo-1-methyl-6-trifluoromethyl-1,2,3,4-tetrahydropyrimidine in 25 ml of dichloromethane at 25° C., and stirring was carried out for 2 hours. The reaction mixture was evaporated down, the oily residue was stirred with water and the precipitate was isolated, washed with water and petroleum ether and dried.

mp.: 216–217° C.

Example 23

3-[4-Chloro-3-ethoximinomethylphenyl]-1-methyl-2-oxo-4-thioxo-6-trifluoromethyl-1,2,3,4-tetrahydropyrimidine (compound 4.1)

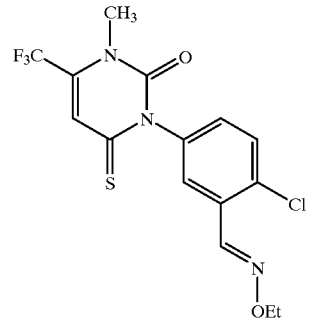

2.4 g of 2,4-bis-(4-methoxyphenyl)-1,3-dithia-2,4-diphosphetane 2,4-disulfide (Lawesson's reagent) were added to a solution of 3.8 g of 3-[4-chloro-3-ethoximinomethylphenyl]-2,4-dioxo-1-methyl-6-trifluoromethyl-1,2,3,4-tetrahydropyrimidine in 100 ml of toluene, and the stirred mixture was refluxed for 10 hours. After cooling and flash chromatography (silica gel, toluene), the solid residue obtained was stirred with petroleum ether, isolated, washed with petroleum ether and dried.

mp.: 129–130° C.

Example 24

3-[3-(2-Bromo-2-methoxyethoxycarbonylethenyl)-4-chlorophenyl]-2,4-dioxo-1-methyl-6-trifluoromethyl-1,2,3,4-tetrahydropyrimidine (compound 1.104)

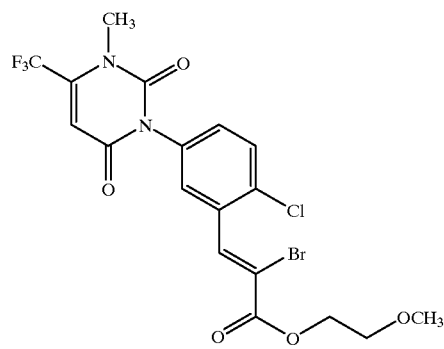

0.52 ml of methoxyethyl bromide was added to a solution of 2.27 g of 3-[3-(2-bromo-2-carboxyethenyl)-4-chlorophenyl]-2,4-dioxo-1-methyl-6-trifluoromethyl-1,2,3,4-tetrahydropyrimidine and 0.76 g of potassium carbonate in dimethylformamide, and the resulting solution was stirred for 17 hours. Thereafter, 100 ml of water were added and the aqueous phase was extracted with twice 100 ml of dichloromethane. The combined organic phases were washed with three times 50 ml of water, dried over sodium sulfate and evaporated down. After flash chromatography (dichloromethane→9:1 dichloromethane/ethyl acetate), the title compound was obtained as an oil.

Example 25

3-[3-(2-Bromo-2-ethylthioethoxycarbonylethenyl)-4-chlorophenyl]-2,4-dioxo-1-methyl-6-trifluoromethyl-1,2,3,4-tetrahydropyrimidine (compound 1.105)

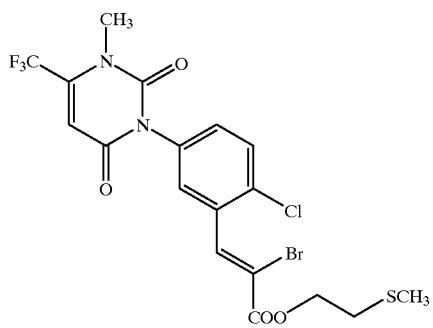

2.36 g of 3-[3-(2-bromo-2-chlorocarbonylethenyl)-4-chlorophenyl]-2,4-dioxo-1-methyl-6-trifluoromethyl-1,2,3,4-tetrahydropyrimidine in 20 ml of tetrahydrofuran were added dropwise to a solution of 0.58 g of 2-ethylmercaptoethanol and 0.56 g of triethylamine in 30 ml of tetrahydrofuran, and stirring was carried out for 5 hours. 100 ml of water were added and the aqueous phase was extracted with twice 100 ml of dichloromethane. The combined organic phases were washed three times with water, dried with sodium sulfate and evaporated down. The solid residue was stirred with diisopropyl ether, removed, washed with diisopropyl ether and petroleum ether and dried.

mp.: 118–120° C.

Example 26

3-(4-Chloro-3-ethoximinomethylphenyl)-2,4-dioxo-5-ethoxycarbonyl- 6-methyl-1,2,3,4-tetrahydropyrimidine

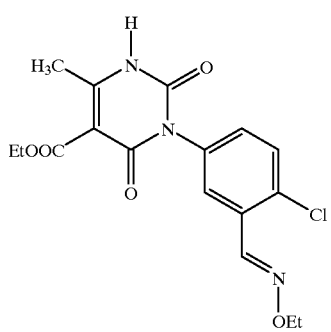

1.8 ml of trichloromethyl chloroformate in 10 ml of dichloromethane were added dropwise to a solution of 7 g of N-(4-chloro-3-ethoximinomethylphenyl)-3-amino-2-ethoxycarbonylcrotonamide and 4.8 g of pyridine in 250 ml of dichloromethane. Stirring was carried out for 15 hours, after which a further 0.8 ml of trichloromethyl chloroformate was added. After stirring had been carried out for 2 days at 25° C. and for 3 hours under reflux, the reaction mixture was washed three times with 150 ml of water, dried over sodium sulfate and evaporated down. After chromatography (dichloromethane/ethyl acetate), the title compound was obtained.

mp.: 232–234° C.

Example 27

3-[4-Chloro-3-(2-chloro-2-ethoxycarbonylethenyl)-phenyl]-2-methylthio-4-oxo-3,4-dihydrothieno[3,4-d]pyrimidine (compound 3.2)

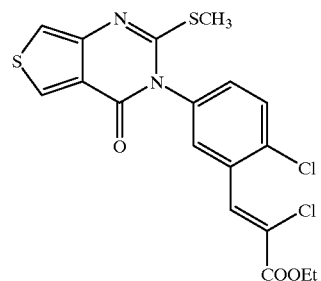

0.28 g of methyl iodide in 5 ml of dimethylformamide was added to a solution of 0.8 g of 3-[4-chloro-3-(2-chloro-2-ethoxycarbonylethenyl)-phenyl]-4-oxo-2-thioxo-1,2,3,4-tetrahydrothieno[3,4-d]pyrimidine and 0.27 g of potassium carbonate in 40 ml of dimethylformamide. Stirring was carried out for 2 days, after which the mixture was cooled to 10° C., 80 ml of water were added and stirring was effected for a further 2 hours. The resulting precipitate was removed, washed with water and dried.

mp.: 142–145° C.

Further compounds were prepared by methods similar to those described in the Examples. These are shown, together with their melting point, in the Tables below, alongside the compounds described in the Examples.

TABLE 1

Active Substance

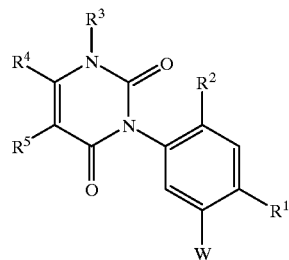

| No. | R¹ | R² | R³ | R⁴ | R⁵ | W | m.p. [° C.] |
|---|---|---|---|---|---|---|---|
| 1.1 | Cl | H | CH$_3$ | CF$_3$ | H | CHO | 151–153 |
| 1.2 | Cl | H | H | CF$_3$ | H | CH=N—OCH$_3$ | 207–208 |
| 1.3 | Cl | H | CH$_3$ | CF$_3$ | H | CH=N—OCH$_3$ | 140–141 |
| 1.4 | Cl | H | H | CF$_3$ | H | CH=N—OC$_2$H$_5$ | 221–223 |
| 1.5 | Cl | H | CH$_3$ | CF$_3$ | H | CH=N—OC$_2$H$_5$ | 132–134 |
| 1.6 | Cl | H | C$_2$H$_5$ | CF$_3$ | H | CH=N—OC$_2$H$_5$ | 121–122 |
| 1.7 | Cl | H | CH$_2$CH=CH$_2$ | CF$_3$ | H | CH=N—OC$_2$H$_5$ | 113–114 |
| 1.8 | Cl | H | CH$_2$C≡CH | CF$_3$ | H | CH=N—OC$_2$H$_5$ | 151–152 |
| 1.9 | Cl | H | CH$_2$C$_6$H$_5$ | CF$_3$ | H | CH=N—OC$_2$H$_5$ | 164–165 |
| 1.10 | Cl | H | H | CF$_3$ | H | CH=CCl—COOC$_2$H$_5$ | 202–206 |
| 1.11 | Cl | H | CH$_3$ | CF$_3$ | H | CH=CCl—COOC$_2$H$_5$ | 159–160 |
| 1.12 | Cl | H | CH$_3$ | CF$_3$ | H | CH=CCl—COOCH$_3$ | 160–161 |
| 1.13 | Cl | H | CH$_3$ | CF$_3$ | H | CH=CCl—COOiC$_3$H$_7$ | 159–160 |
| 1.14 | Cl | H | CH$_3$ | CF$_3$ | H | CH=CCl—COOnC$_3$H$_7$ | 130–131 |
| 1.15 | Cl | H | CH$_3$ | CF$_3$ | H | CH=CCl—COOnC$_4$H$_9$ | 109–110 |
| 1.16 | Cl | H | CH$_3$ | CF$_3$ | H | CH=CCl—COOtC$_4$H$_9$ | 154–155 |
| 1.17 | Cl | H | CH$_3$ | CF$_3$ | H | CH=CBr—COOCH$_3$ | 162–163 |
| 1.18 | Cl | H | CH$_3$ | CF$_3$ | H | CH=CBr—COOC$_2$H$_5$ | 147–148 |
| 1.19 | Cl | H | CH$_3$ | CF$_3$ | H | CH=CBr—COOiC$_3$H$_7$ | 153–154 |
| 1.20 | Cl | H | CH$_3$ | CF$_3$ | H | CH=CBr—COOtC$_4$H$_9$ | 150–151 |
| 1.21 | Cl | H | CH$_3$ | CF$_3$ | H | CH=Cl—COOCH$_3$ | 178–179 |
| 1.22 | Cl | H | CH$_3$ | CF$_3$ | H | CH=C(CN)—COOCH$_3$ | 187–188 |
| 1.23 | Cl | H | CH$_3$ | CF$_3$ | H | CH=C(CH$_3$)—COOCH$_3$ | 159–160 |
| 1.24 | Cl | H | CH$_3$ | CF$_3$ | H | CH=C(CH$_3$)—COOC$_2$H$_5$ | Oil |
| 1.25 | Cl | H | CH$_3$ | CF$_3$ | H | CH=C(CH$_3$)—CHO | 154–155 |
| 1.26 | Cl | H | CH$_3$ | CF$_3$ | H | CH=CH—CO—CH$_3$ | 227–228 |
| 1.27 | Cl | H | CH$_3$ | CF$_3$ | H | CH=CH—CO—iC$_3$H$_7$ | 135–136 |
| 1.28 | Cl | H | CH$_3$ | CF$_3$ | H | CH=CH—CO—4Cl—C$_6$H$_4$ | 246–247 |
| 1.29 | Cl | H | CH$_3$ | CF$_3$ | H | CH=CH—CO—CH$_2$Cl | 188–189 |
| 1.30 | Cl | H | CH$_3$ | CF$_3$ | H | CH=CH—CO—CH$_2$OCH$_3$ | 189–190 |
| 1.31 | Cl | H | CH$_3$ | CF$_3$ | H | CH=CH—CO—CH$_2$OC$_2$H$_5$ | 184–185 |
| 1.32 | Cl | H | CH$_3$ | CF$_3$ | H | CH=CH—CO—CHCl$_2$ | 181–182 |
| 1.33 | Cl | H | CH$_3$ | CF$_3$ | H | CH=CH—CO—CH(OC$_2$H$_5$)$_2$ | 118–119 |
| 1.34 | Cl | H | CH$_3$ | CF$_3$ | H | CH=CH—CN | 263–265 (9:1)[b] |
| 1.35 | Cl | H | CH$_3$ | CF$_3$ | H | CH=CH—CH=C(CH$_3$)—COOC$_2$H$_5$ | 229–231 (1:2)[b] |
| 1.36 | Cl | H | C$_2$H$_5$ | CF$_3$ | H | CH=CCl—COOC$_2$H$_5$ | 137–138 |
| 1.37 | Cl | H | CH$_2$CH=CH$_2$ | CF$_3$ | H | CH=CCl—COOC$_2$H$_3$ | 134–135 |
| 1.38 | Cl | H | CH$_2$C≡CH | CF$_3$ | H | CH=CCl—COOC$_2$H$_3$ | 158–159 |
| 1.39 | Cl | H | CH$_2$CN | CF$_3$ | H | CH=CCl—COOC$_2$H$_3$ | 150–151 |
| 1.40 | Cl | H | CH$_2$COOC$_2$H$_5$ | CF$_3$ | H | CH=CCl—COOC$_2$H$_3$ | 179–180 |
| 1.41 | Cl | H | H | CF$_3$ | H | CH=CCl—COOH | >250 |
| 1.42 | Cl | H | CH$_3$ | CF$_3$ | Cl | CH=CCl—COOC$_2$H$_5$ | 160–164 |
| 1.43 | Cl | H | CH$_3$ | CF$_3$ | H | CH=N—OH | 94–98 |
| 1.44 | Cl | H | CH$_3$ | CF$_3$ | H | CH=N—O-n-C$_3$H$_7$ | 87–88 |
| 1.45 | Cl | H | CH$_3$ | CF$_3$ | H | CH=N—OCH$_2$CH=CH$_2$ | 82–83 |
| 1.46 | Cl | H | CH$_3$ | CF$_3$ | H | CH=N—O-n-C$_4$H$_9$ | 83–84 |
| 1.47 | Cl | H | CH$_3$ | CF$_3$ | H | CH=N—O-i-C$_4$H$_9$ | 96–97 |
| 1.48 | Cl | H | CH$_3$ | CF$_3$ | H | CH=N—O(CH$_2$)$_2$CH(CH$_3$)$_2$ | 77–79 |
| 1.49 | Cl | H | CH$_3$ | CF$_3$ | H | CH=N—O-n-C$_6$H$_{13}$ | 75–76 |
| 1.50 | Cl | H | CH$_3$ | CF$_3$ | H | CH=N—OCH$_2$—CCl=CH$_2$ | 108–110 |
| 1.51 | Cl | H | CH$_3$ | CF$_3$ | H | CH=N—O(CH$_2$)$_2$—CCl=CH$_2$ | 127–129 |
| 1.52 | Cl | H | CH$_3$ | CF$_3$ | H | CH=N=OCH$_2$CH=CH—CH$_2$OtC$_4$H$_9$ | 86–88 |
| 1.53 | Cl | H | CH$_3$ | CF$_3$ | H | CH=N—O—CH$_2$CN | 171–174 |
| 1.54 | Cl | H | CH$_3$ | OC$_2$H$_5$ | H | CH=N—OC$_2$H$_5$ | 115–118 |
| 1.55 | Cl | H | CH$_3$ | CF$_3$ | H | CH=N—OCH(CH$_3$)COOC$_2$H$_5$ | Oil |
| 1.56 | Cl | H | CH$_3$ | CF$_3$ | H | CH=N—OCH$_2$-cyclo-C$_6$H$_{11}$ | 111–113 |

TABLE 1-continued

Active Substance

| No. | $R^1$ | $R^2$ | $R^3$ | $R^4$ | $R^5$ | W | m.p. [° C.] |
|---|---|---|---|---|---|---|---|
| 1.57 | Cl | H | CH$_3$ | CF$_3$ | H | CH=N—O—CH$_2$—CH(dioxolanyl-CH$_3$) | 96–98 |
| 1.58 | Cl | H | CH$_3$ | CF$_3$ | H | CH=N—O—CH$_2$—(4-bromothien-2-yl) | 105–107 |
| 1.59 | Cl | H | CH$_3$ | CF$_3$ | H | CH=N—O—CH$_2$—4Cl—C$_6$H$_4$ | 117–121 |
| 1.60 | Cl | H | CH$_3$ | CF$_3$ | H | CH=N—O—(CH$_2$)$_2$—2F—C$_6$H$_4$ | 95–98 |
| 1.61 | Cl | H | CH$_3$ | CF$_3$ | H | CH=N—O(CH$_2$)$_2$—CH=CH—4Cl—C$_6$H$_4$ | 139–140 (8:2)[b] |
| 1.62 | Cl | H | CH$_3$ | CF$_3$ | H | CH=N—O—(CH$_2$)$_3$—C≡C—4F—C$_6$H$_4$ | 130–131 |
| 1.63 | Cl | H | H | CF$_2$Cl | H | CH=CCl—CO$_2$C$_2$H$_5$ | 182–183 |
| 1.64 | Cl | H | CH$_3$ | CF$_2$Cl | H | CH=CCl—COOC$_2$H$_5$ | 111–113 |
| 1.65 | Cl | H | H | CH$_3$ | CH$_3$ | CH=CCl—COOC$_2$H$_5$ | 236–238 |
| 1.66 | Cl | H | CH$_3$ | CH$_3$ | CH$_3$ | CH=CCl—COOC$_2$H$_5$ | 193–194 |
| 1.67 | Cl | F | CH$_3$ | CF$_3$ | H | CHO | 172–174 |
| 1.68 | Cl | F | CH$_3$ | CF$_3$ | H | CH=N—OCH$_3$ | 135–137 (85:15)[b] |
| 1.69 | Cl | F | H | CF$_3$ | H | CH=N—OC$_2$H$_5$ | 175–178 |
| 1.70 | Cl | F | CH$_3$ | CF$_3$ | H | CH=N—OC$_2$H$_5$ | 103–105 |
| 1.71 | Cl | F | CH$_3$ | CF$_3$ | H | CH=CBr—COOCH$_3$ | 125–126 |
| 1.72 | Cl | F | CH$_3$ | CF$_3$ | H | CH=CBr—COOC$_2$H$_5$ | 115–117 |
| 1.73 | Cl | F | CH$_3$ | CF$_3$ | H | CH=CCl—COOCH$_3$ | 116–117 |
| 1.74 | Cl | F | CH$_3$ | CF$_3$ | H | CH=CCl—COOC$_2$H$_5$ | 133–134 |
| 1.75 | Cl | H | H | CH$_3$ | H | CH=N—OC$_2$H$_5$ | >280 |
| 1.76 | Cl | H | H | CF$_2$Cl | H | CH=N—OC$_2$H$_5$ | 65–67 |
| 1.77 | Cl | H | CH$_3$ | CH$_3$ | H | CH=N—OC$_2$H$_5$ | 111–112 |
| 1.78 | Cl | H | CH$_3$ | CF$_2$Cl | H | CH=N—OC$_2$H$_5$ | 108–109 |
| 1.79 | Cl | H | H | —(CH$_2$)$_4$— | | CH=CCl—COOC$_2$H$_5$ | 218–220 |
| 1.80 | Cl | H | H | —(CH$_2$)$_4$— | | CH=CH—COOCH$_3$ | 261–276 |
| 1.81 | Cl | H | CH$_3$ | —(CH$_2$)$_4$— | | CH=CCl—COOC$_2$H$_5$ | 169–170 |
| 1.82 | Cl | H | H | —(CH=CH)$_2$— | | CH=CCl—COOC$_2$H$_5$ | 245–246 |
| 1.83 | Cl | H | CH$_3$ | —(CH=CH)$_2$— | | CH=CCl—COOC$_2$H$_5$ | 204–205 |
| 1.84 | Cl | H | H | CF$_3$ | H | 1,3-dioxolan-2-yl | 180–182 |
| 1.85 | Cl | H | CH$_3$ | CF$_3$ | H | CH=CH—COOCH$_2$CF$_3$ | 170–172 |
| 1.86 | Cl | H | CH$_3$ | CF$_3$ | H | CH$_2$—CH(Cl)—COOCH$_3$ | Oil |
| 1.87 | Cl | H | H | C$_6$H$_5$ | H | CH=N—OEt | 198–200 |
| 1.88 | Cl | H | CH$_3$ | C$_6$H$_5$ | H | CH=N—OEt | 173–175 |
| 1.89 | Cl | H | H | =CHSCH= | | CH=CCl—COOEt | 278–280 |
| 1.90 | Cl | H | CH$_3$ | CF$_3$ | H | CH=N—NH—COOEt | 111–116 |
| 1.91 | Cl | H | CH$_3$ | CF$_3$ | H | CH=N—NH—CH=C(CN)—COOCH$_3$ | 219–221 |
| 1.92 | Cl | H | CH$_3$ | CF$_3$ | H | CH=CCl—COOH | 216–217 |
| 1.93 | Cl | H | CH$_3$ | CF$_3$ | H | CH=CBr—COOH | 193–195 |
| 1.94 | Cl | H | H | 4OCH$_3$—C$_6$H$_4$ | H | CH=N—OC$_2$H$_5$ | 246–247 |
| 1.95 | Cl | H | H | 4Cl—C$_6$H$_4$ | H | CH=N—OC$_2$H$_5$ | 270–272 |
| 1.96 | Cl | H | CH$_3$ | 4OCH$_3$—C$_6$H$_4$ | H | CH=N—OC$_2$H$_5$ | 157–159 |
| 1.97 | Cl | H | CH$_3$ | 4Cl—C$_6$H$_4$ | H | CH=N—OC$_2$H$_5$ | 193–195 |
| 1.98 | Cl | H | H | C$_6$H$_5$ | COOCH$_3$ | CH=N—OC$_2$H$_5$ | 225–232 |
| 1.99 | Cl | H | CH$_3$ | C$_6$H$_5$ | COOCH$_3$ | CH=N—OC$_2$H$_5$ | 166–168 |
| 1.100 | Cl | H | H | CH$_3$ | COOC$_2$H$_5$ | CH=N—OC$_2$H$_5$ | 232–234 |
| 1.101 | Cl | H | CH$_3$ | CH$_3$ | COOC$_2$H$_5$ | CH=N—OC$_2$H$_5$ | 105 |
| 1.102 | Cl | H | CH$_3$ | CF$_3$ | H | CH=CBr—COOCH$_2$C≡CH | 128–130 |
| 1.103 | Cl | H | CH$_3$ | CF$_3$ | H | CH=CBr—COOCH$_2$COOCH$_3$ | 152–154 |
| 1.104 | Cl | H | CH$_3$ | CF$_3$ | H | CH=CBr—COO(CH$_2$)$_2$OCH$_3$ | Oil |
| 1.105 | Cl | H | CH$_3$ | CF$_3$ | H | CH=CBr—COO(CH$_2$)$_2$SC$_2$H$_5$ | 118–120 |

TABLE 1-continued

Active Substance

| No. | R$^1$ | R$^2$ | R$^3$ | R$^4$ | R$^5$ | W | m.p. [° C.] |
|---|---|---|---|---|---|---|---|
| 1.106 | Cl | H | CH$_3$ | CF$_3$ | H | CH=CBr—COOCH$_2$C$_6$H$_5$ | 178–179 |
| 1.107 | Cl | H | CH$_3$ | CF$_3$ | H | CH=CBr—COO—N=C(CH$_3$)$_2$ | 155–156 |
| 1.108 | Cl | H | CH$_3$ | CF$_3$ | H | CH=CBr—CO—N-morpholino | 159–160 |
| 1.109 | Cl | H | CH$_3$ | CF$_3$ | H | CH=CCl—CO—CH$_3$ | 157–158 |
| 1.110 | Cl | F | CH$_3$ | CF$_3$ | H | CH=C(CH$_3$)—CHO | 52–55 |
| 1.111 | Cl | H | H | OC$_2$H$_5$ | H | CH=N—OC$_2$H$_5$ | >260 |
| 1.112 | Cl | H | H | CH$_3$ | H | CH=CHCOOC$_2$H$_5$ | 213–215 |
| 1.113 | Cl | H | H | CF$_3$ | H | C(CH$_3$)=N—OC$_2$H$_5$ | 157–159 |
| 1.114 | Cl | H | CH$_3$ | CF$_3$ | H | C(CH$_3$)=N—OC$_2$H$_5$ | 96–98 |
| 1.115 | Cl | H | H | SC$_2$H$_5$ | H | CH=N—OC$_2$H$_5$ | 212–215 |
| 1.116 | Cl | H | CH$_3$ | CF$_3$ | H | CH=N—OCH$_2$—CH(CH$_3$)—OH | 89–96 |

TABLE 2

Active Substance

| No. | R$^2$ | W | m.p. |
|---|---|---|---|
| 2.1 | H | 1,3-dioxan-2-yl | 87–92 |
| 2.2 | H | 5,5-dimethyl-1,3-dioxan-2-yl | 120–123 |
| 2.3 | H | 5-methoxy-5-methyl-1,3-dioxan-2-yl | 192–196 |
| 2.4 | H | 5-cyclohexyloxy-5-methyl-1,3-dioxan-2-yl | 64–68$^{b)}$ |
| 2.5 | H | 5,5-(diethoxycarbonyl)-1,3-dioxan-2-yl | 65–68 |
| 2.6 | H | (spiro bis-dioxane with CH$_2$Cl) | 201–204 |
| 2.7 | H | 5-cyclohexyl-5-methyl-1,3-dioxan-2-yl | 87–91 (2:1)$^{b)}$ |
| 2.8 | H | 5-butyl-5-ethyl-1,3-dioxan-2-yl | 55–58 (1:1)$^{b)}$ |
| 2.9 | H | 5-methyl-5-phenyl-1,3-dioxan-2-yl | 95–98 (2:1)$^{b)}$ |
| 2.10 | H | 4-methoxycarbonyl-5-methyl-1,3-dioxolan-2-yl | Oil (1:1)$^{b)}$ |
| 2.11 | H | 4-methoxycarbonyl-4-methyl-1,3-dioxolan-2-yl | Oil (1:1)$^{b)}$ |
| 2.12 | H | 4-ethoxycarbonyl-4-methyl-1,3-dioxolan-2-yl | Oil (1:1)$^{b)}$ |
| 2.13 | H | 4-methyl-1,3-dioxolan-2-yl | Oil (1:1)$^{b)}$ |
| 2.14 | H | 4-n-propyl-1,3-dioxolan-2-yl | Oil (1:1)$^{b)}$ |
| 2.15 | H | 4-vinyl-1,3-dioxolan-2-yl | Oil (1:1)$^{b)}$ |
| 2.16 | H | 2-ethyl-1,3-dioxolan-2-yl | Oil (1:1)$^{b)}$ |
| 2.17 | H | 4,5-dimethyl-1,3-dioxolan-2-yl | 149–151$^{c)}$ |
| 2.18 | H | (hexahydrobenzo-1,3-dioxol-2-yl, methyl) | Oil (1:1)$^{b)}$ |
| 2.19 | H | 4-tert.-butyl-1,3-dioxolan-2-yl | Oil (1:1)$^{b)}$ |
| 2.20 | H | 4,4,5-trimethyl-1,3-dioxolan-2-yl | Oil (1:1)$^{b)}$ |
| 2.21 | H | 4-trichlormethyl-1,3-dioxolan-2-yl | 114–116 (6:4)$^{b)}$ |
| 2.22 | H | dimethoxymethyl | 92–94 |
| 2.23 | H | 4-i-butoxycarbonyl-4-methyl-1,3-dioxolan-2-yl | Oil (1:1)$^{b)}$ |
| 2.24 | H | 4-n-butoxycarbonyl-4-methyl-1,3-dioxolan-2-yl | Oil (1:1)$^{b)}$ |
| 2.25 | F | 4-n-butoxycarbonyl-4-methyl-1,3-dioxolan-2-yl | Oil (1:1)$^{b)}$ |
| 2.26 | F | 4-methyl-1,3-dithiolan-2-yl | 67–69 (1:1)$^{b)}$ |
| 2.27 | H | 1,3-dioxolan-2-yl | 58–60 |
| 2.28 | H | di-(2-chlor-ethoxy)-methyl | Oil |
| 2.29 | H | 1,3-dithian-2-yl | 176–177 |
| 2.30 | H | 1,3-dithiolan-2-yl | 177–178 |
| 2.31 | H | 4-methyl-1,3-dithiolan-2-yl | 115–118 (1:1)$^{b)}$ |

TABLE 2-continued

Active Substance

[Structure: pyrimidine-2,4-dione with N-CH3, F3C, and N-aryl (R2, Cl, W) substituents]

| No. | R² | W | m.p. |
|---|---|---|---|
| 2.32 | H | 1,3-oxathiolan-2-yl | 168–170 |
| 2.33 | H | diethoxymethyl | Oil |
| 2.34 | H | 1,3-oxathian-2-yl | Oil |
| 2.35 | H | 4-methyl-1,3-dithian | Oil (9:1)[b] |
| 2.36 | H | di-n-propoxy-methyl | Oil |
| 2.37 | H | 4-methyl-1,3-oxathiolan-2-yl | Oil (7:3)[b] |

Remark:
[a] Still contains 15% of isomeric allyloxime
[b] Isomer mixture
[c] trans-isomer

TABLE 3

Active Substance

[Structure: pyrimidinone with R⁴, R⁵, X¹R³¹, R², N-aryl (R¹, W) substituents]

| No. | R¹ | R² | R³¹ | X¹ | R⁴ | R⁵ | W | m.p. |
|---|---|---|---|---|---|---|---|---|
| 3.1 | Cl | H | CH₃ | O | CF₃ | H | CH=CCl—COOCH₃ | 151–152 |
| 3.2 | Cl | H | CH₃ | S | =CH—S—CH= | | CH=CCl—COOC₂H₅ | 142–145 |

TABLE 4

Active Substance

[Structure: pyrimidine with F3C, N-CH3, X¹, X², R², and N-aryl (Cl, W) substituents]

| No. | X¹ | X² | R² | W | m.p. |
|---|---|---|---|---|---|
| 4.1 | O | S | H | CH=N—OC₂H₅ | 129–130 |
| 4.2 | O | S | H | CH=CCl—COOC₂H₅ | 129–132 |

Those compounds which were obtained as oils could be characterized unambiguously with the aid of their IR data, which are shown in the Table below.

| Compound No. | Characteristic IR Data/cm⁻¹ (Film) |
|---|---|
| 1.24 | $\upsilon$ = 1731, 1685, 1474, 1372, 1272, 1231, 1185, 1152, 1069, 1050 |
| 1.55 | $\upsilon$ = 1750, 1732, 1685, 1469, 1372, 1272, 1232, 1185, 1148, 1049 |
| 1.70 | $\upsilon$ = 1736, 1691, 1492, 1408, 1369, 1271, 1185, 1151, 1069, 1050 |
| 1.86 | $\upsilon$ = 1747, 1730, 1685, 1479, 1373, 1274, 1258, 1237, 1185, 1150 |
| 2.10 | $\upsilon$ = 1758, 1732, 1684, 1480, 1373, 1273, 1233, 1186, 1150, 1104 |
| 2.11 | $\upsilon$ = 1731, 1685, 1476, 1373, 1272, 1233, 1185, 1150, 1070, 1047 |
| 2.12 | $\upsilon$ = 1731, 1686, 1476, 1373, 1272, 1233, 1185, 1151, 1070, 1047 |
| 2.13 | $\upsilon$ = 1730, 1685, 1476, 1373, 1272, 1232, 1186, 1151, 1070, 1044 |
| 2.14 | $\upsilon$ = 1731, 1683, 1475, 1372, 1271, 1232, 1185, 1150, 1070, 1044 |
| 2.15 | $\upsilon$ = 1730, 1685, 1475, 1372, 1271, 1232, 1185, 1150, 1070, 1046 |
| 2.16 | $\upsilon$ = 1730, 1685, 1476, 1372, 1272, 1232, 1186, 1151, 1070, 1045 |
| 2.18 | $\upsilon$ = 1731, 1686, 1474, 1371, 1271, 1231, 1185, 1151, 1091, 1046 |
| 2.19 | $\upsilon$ = 1731, 1686, 1478, 1372, 1271, 1232, 1185, 1151, 1070, 1044 |
| 2.20 | $\upsilon$ = 1731, 1686, 1474, 1371, 1271, 1231, 1185, 1151, 1102, 1045 |
| 2.23 | $\upsilon$ = 1732, 1687, 1474, 1373, 1272, 1185, 1151, 1047 |
| 2.24 | $\upsilon$ = 1731, 1686, 1476, 1373, 1272, 1233, 1185, 1151, 1047 |
| 2.25 | $\upsilon$ = 1736, 1691, 1497, 1370, 1273, 1213, 1185, 1151, 1084, 1069 |
| 2.28 | $\upsilon$ = 1730, 1684, 1475, 1373, 1272, 1233, 1185, 1152, 1072, 1046 |
| 2.33 | $\upsilon$ = 1731, 1686, 1474, 1372, 1272, 1231, 1185, 1151, 1070, 1049 |
| 2.34 | $\upsilon$ = 1731, 1686, 1477, 1372, 1272, 1241, 1184, 1148, 1072, 1047 |
| 2.35 | $\upsilon$ = 1731, 1685, 1478, 1372, 1271, 1257, 1184, 1149, 1045 |

-continued

| Compound No. | Characteristic IR Data/cm$^{-1}$ (Film) |
|---|---|
| 2.36 | $\upsilon$ = 1732, 1688, 1474, 1371, 1279, 1231, 1185, 1151, 1070, 1045 |
| 2.37 | $\upsilon$ = 1732, 1685, 1476, 1372, 1271, 1234, 1184, 1148, 1070, 1043 |

Intermediates:

Intermediate Example 1

2-Chloro-3-[4-chloro-3-(2-chloro-2-ethoxycarbonylethenyl)-phenyl]-4-oxo-6-trifluoromethyl-3,4-dihydropyrimidine

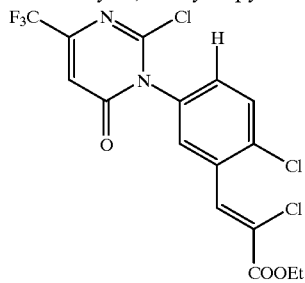

13.8 ml of phosphoryl chloride were added dropwise to 12.6 g of 3-[4-chloro-3-(2-chloro-2-ethoxycarbonylethenyl)-phenyl]-2,4-dioxo-6-trifluoromethyl-1,2,3,4-tetrahydropyrimidine, and stirring was carried out for 2 hours at room temperature. Thereafter, 2.1 ml of dimethylformamide were added and stirring was continued for 15 hours at 110–115° C. The reaction mixture was evaporated down under reduced pressure, the residue was added to 150 ml of ice water and the mixture was extracted with twice 100 ml of dichloromethane. The combined organic phases were washed with water, 10% strength sodium bicarbonate and again with water, dried over sodium sulfate and evaporated down. The oil obtained was subjected to flash chromatography (dichloromethane), and the crystalline solid obtained therefrom was stirred with petroleum ether, removed, washed with a little petroleum ether and dried.

mp.: 114–115° C.

Intermediate Example 2

Reaction of 4-chloro-3-ethoximinophenyl isocyanate with ethyl 3-aminocrotonate 22.5 g of 4-chloro-3-ethoximinophenyl isocyanate in 100 ml of toluene were added dropwise to a solution of 14.2 g of ethyl 3-aminocrotonate in 450 ml of toluene under reflux, and the reaction mixture was stirred under reflux for 4 hours and at room temperature for 2 days. Removing and drying the resulting precipitate gave N-(4-chloro-3-ethoximinomethylphenyl)-3-amino-2-ethoxycarbonylcrotonamide

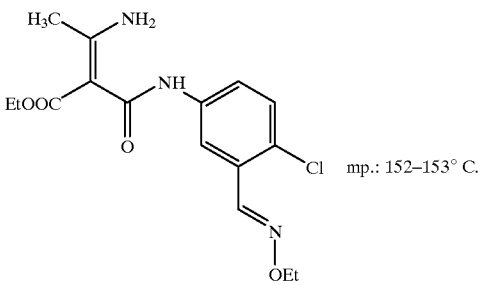

mp.: 152–153° C.

The filtrate was evaporated down and the residue chromatographed (dichloromethane). Trituration with cold petroleum ether, removal and drying gave N-(4-chloro-3-ethoximinomethylphenyl)-N'-(1-ethoxycarbonylpropen-2-yl)-urea.

mp.: 126–127° C.

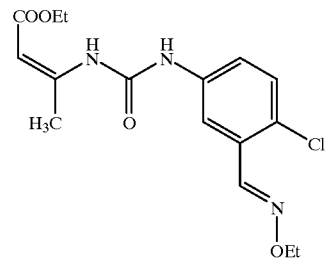

The following intermediates were prepared in a similar manner:

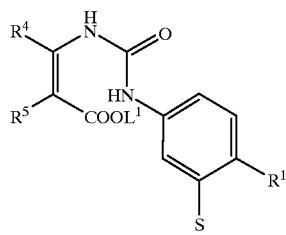

| No. | L$^1$ | R$^1$ | R$^4$ | R$^5$ | W | m.p. |
|---|---|---|---|---|---|---|
| II.1 | C$_2$H$_5$ | Cl | CH$_3$ | H | CH=N—OC$_2$H$_5$ | 126–127 |
| II.2 | C$_2$H$_5$ | Cl | CH$_3$ | H | CH=CCl—COOC$_2$H$_5$ | 136–137 |

-continued

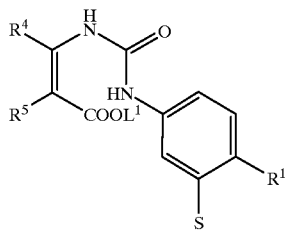

| No. | L¹ | R¹ | R⁴ | R⁵ | W | m.p. |
|---|---|---|---|---|---|---|
| II.3 | $CH_3$ | Cl | H | $COOCH_3$ | $CH=CCl-COOC_2H_5$ | 198–200 |
| II.4 | $C_2H_5$ | Cl | —(CH₂)₄— | | $CH=CCl-COOC_2H_5$ | 129–131 |
| II.5 | $C_2H_5$ | Cl | —(CH=CH)₂— | | $CH=CCl-COOC_2H_5$ | 141–142 |
| II.6 | $C_2H_5$ | Cl | $CH_3$ | $CH_3$ | $CH=CCl-COOC_2H_5$ | 127–130 |
| II.7 | $C_2H_5$ | Cl | $OC_2H_5$ | H | $CH=N-OC_2H_5$ | Oil |
| II.8 | $C_2H_5$ | Cl | $SC_2H_5$ | H | $CH=N-OC_2H_5$ | 103–105 |

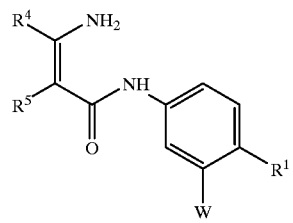

| No. | R¹ | R⁴ | R⁵ | W | m.p. |
|---|---|---|---|---|---|
| VIII.1 | Cl | $CH_3$ | $COOC_2H_5$ | $CH=CCl-COOC_2H_5$ | 160–161 |
| VIII.2 | Cl | $CH_3$ | $COOC_2H_5$ | $CH=N-OC_2H_5$ | 153–154 |
| VIII.3 | Cl | Ph | $COOCH_3$ | $CH=N-OC_2H_5$ | Oil |
| VIII.4 | Cl | $SC_2H_5$ | $COOC_2H_5$ | $CH=N-OC_2H_5$ | 151–153 |

Intermediates Example 3

3-Amino-4-chloro-4,4-difluorocrotonates

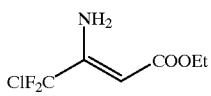

Ammonia was passed into ethyl 4-chloro-4,4-difluoroacetoacetate at 60° C. until saturation had been reached and stirring was carried out for 5 hours at 70° C., after which gaseous ammonia was passed in again for one hour and stirring was again carried out for 2 hours at 70° C. The product was obtained after distillation over a 10 cm Vigreux column under reduced pressure from a water pump. bp.: 129–130° C./140 hPa.

Ethyl 3-amino-4,4,4-trifluorocrotonate was prepared in the same manner.

Intermediate Example 4

4-Chloro-3-(1,3-dioxolan-2-yl)-phenyl isocyanate

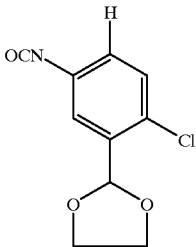

2.0 g of 4-chloro-3-(1,3-dioxolan-2-yl)-aniline in 25 ml of ethyl acetate were added to a solution of 3.0 g of trichloromethyl chloroformate in 50 ml of toluene at about 20–25° C. This mixture was stirred for 2 hours at 20–25° C. and then for a further 5 hours at the reflux temperature. Thereafter, the reaction mixture was evaporated down and the residue was dried under greatly reduced pressure.

Yield: 2.0 g (oil).

Intermediate Example 5

4-Chloro-3-(α-chloroethoxycarbonylethenyl)-phenyl isocyanate

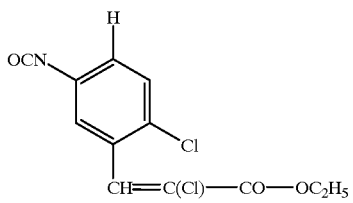

108.8 g of trichloromethyl chloroformate were added to a suspension of 130 g of 4-chloro-3-(α-chloroethoxycarbonylethenyl)-aniline in 1200 ml of toluene. The stirred mixture was refluxed for 16 hours. After the resulting precipitate had been separated off, the solvent was removed under reduced pressure, the residue was stirred with petroleum ether and the precipitate was removed and dried.

mp.: 48–50° C.

By 4-Chloro-3-(ethoximinomethyl)-phenyl isocyanate, an oil,
4-chloro-3-(ethoximinomethyl)-6-fluorophenyl isocyanate, an oil, and
4-chloro-3-(methoximinomethyl)-phenyl isocyanate, an oil, were prepared in the same manner.

Intermediate Example 6

N-[4-Chloro-3-(2-chloro-2-ethoxycarbonylethenyl)-phenyl]-urea

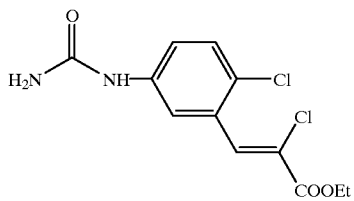

Gaseous ammonia was passed into a solution of 14.3 g of 4-chloro-3-(2-chloro-2-ethoxycarbonylethenyl)-phenyl isocyanate in 200 ml of tetrahydrofuran at 20° C. in the course of 1.5 hours until saturation had been reached, and stirring was carried out for 1 hour. The precipitate was removed and washed with ether. The filtrate was evaporated down, the residue was stirred with ether and the product was removed. The solids were combined.

mp.: 209–210° C.

Intermediate Example 7

4-Chloro-3-(2-chloro-2-ethoxycarbonylethenyl)-N-ethoxy-carbonylaniline

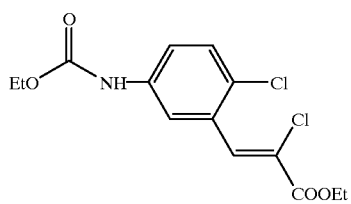

6.0 g of ethyl chloroformate were added dropwise to a solution of 13 g of 4-chloro-3-(2-chloro-2-ethoxycarbonylethenyl)-aniline in 150 g of toluene and 5.6 g of triethylamine at 20–40° C., and stirring was carried out for 5 hours at room temperature. The reaction mixture was washed three times with water, dried over sodium sulfate and evaporated down and the residue was stirred with petroleum ether, removed, washed with petroleum ether and dried.

mp.: 102–104° C.

Intermediate Example 8

Methyl β-aminocinnamate

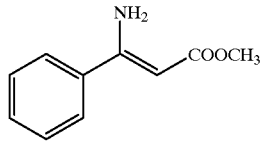

47 g of bromobenzene in 90 ml of ether were added dropwise to 7.2 g of magnesium in 20 ml of ether under reflux, and the stirred mixture was refluxed for 1 hour. Thereafter, 9.9 g of methyl cyanoacetate were added dropwise while cooling with ice, and stirring was carried out for 1 hour at room temperature, for 5 hours under reflux and again for 15 hours at room temperature. 300 ml of ammonium chloride were carefully added to the reaction mixture and the aqueous phase was extracted twice with ether and the combined organic phases were washed three times with water, dried over sodium sulfate and evaporated down. The residue was distilled under greatly reduced pressure. 13 g of methyl β-amino-cinnamate were obtained (110–112° C., 10.15 mbar).

Methyl β-amino-4-chlorocinnamate (from 1-bromo-4-chlorobenzene, amorphous solid) and methyl β-amino-4-methoxycinnamate (bp.: 165–167° C., 0.15 hPa) were obtained in the same manner.

Intermediate Example 9

Methyl 4-isothiocyanatothiophen-3-carboxylate

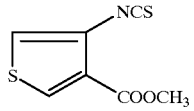

19.4 g of methyl 4-aminothiophen-3-carboxylate hydrochloride were added to a suspension of 7.7 ml of thiophosgene and 18.5 g of sodium bicarbonate in 70 ml of water and 200 ml of dichloromethane at room temperature in the course of 30 minutes, and stirring was carried out for 1 hour at room temperature. After separation of the phases, the aqueous phase was extracted once with dichloromethane and the combined organic phases were washed once with water, dried over sodium sulfate and evaporated down.

mp.: 93–95° C.

Intermediate Example 10

N-[4-Chloro-3-(2-chloro-2-ethoxycarbonylethenyl)-phenyl]-N'-(4-methoxycarbonylthien-3-yl)-thiourea

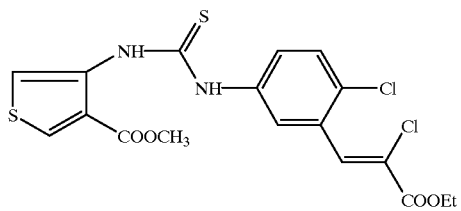

4 g of methyl 4-isothiocyanatothiophen-3-carboxylate in 50 ml of toluene were added dropwise to a solution of 5.2 g of 4-chloro-(2-chloro-2-ethoxycarbonylethenyl)-aniline in 50 ml of toluene. The reaction mixture was stirred for a total of 78 hours at room temperature and 9 hours at 90° C. The precipitate obtained was removed, washed with toluene and then recrystallized from ethanol.

mp.: 158–160° C.

Intermediate Example 11

3-[3-(2-Bromo-2-chlorocarbonylethenyl)-4-chlorophenyl]-2,4-dioxo-1-methyl-6-trifluoromethyl-1,2,3,4-tetrahydropyrimidine

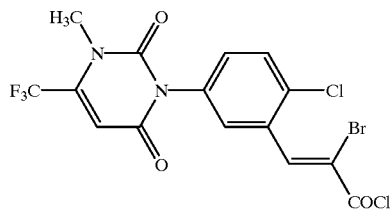

1.6 g of thionyl chloride were added to a solution of 4.5 g of 3-[3-(2-bromo-2-carboxyethenyl)-4-chlorophenyl]-2,4-dioxo-1-methyl-6-trifluoromethyl-1,2,3,4-tetrahydropyrimidine and 0.1 ml of dimethylformamide in 100 ml of toluene. The reaction mixture was heated slowly to the reflux temperature, stirred under reflux for 5 hours and evaporated down, and the residue was dried under greatly reduced pressure.

mp.: 125–127° C.

Use Examples (Herbicidal Activity)

The herbicidal activity of the substituted phenyluracils I, Ia and Ib could be demonstrated by greenhouse experiments:

The culture vessels used were plastic flower pots containing loamy sand with about 3.0% of humus as the substrate. The seeds of the test plants were sown separately according to species.

In the preemergence treatment, the active ingredients suspended or emulsified in water were applied, directly after sowing, by means of finely distributing nozzles. The vessels were lightly watered in order to promote germination and growth and were then covered with transparent plastic covers until the plants had begun to grow. This covering ensures uniform germination of the test plants, unless this has been adversely affected by the active ingredients.

For the purpose of the postemergence treatment, the test plants were grown in the test vessels themselves or were planted in the test vessels a few days beforehand. The active ingredients suspended or emulsified in water were not applied until a height of growth of from 3 to 15 cm, depending on the form of growth.

The plants were kept at 10–25° C. or 20–35° C., according to species. The test periods extended over from 2 to 4 weeks. During this time, the plants were tended and their reaction to the individual treatments was evaluated.

Rating was based on a scale from 0 to 100. 100 means no emergence of the plants or complete destruction of at least the above-ground parts and 0 means no damage on normal growth.

The plants used in the greenhouse experiments consisted of the following species:

| Botanical name | Common name |
| --- | --- |
| Abutilon theophrasti | velvet leaf |
| Amaranthus retroflexus | redroot pigweed |
| Centaurea cyanus | cornflower |
| Echinochloa crus-galli | barnyard grass |
| Ipomoea spp. | morning glory |
| Solanum nigrum | black nightshade |

At application rates of 0.06 and 0.03 kg/ha, undesirable broad-leaved plants can be very readily controlled with compound No. 3.1 by the postemergence method.

Furthermore, undesirable broad-leaved plants and grasses can be very readily controlled by the post-emergence use of 0.5 kg/ha of compounds 1.1, 1.3, 1.5, 1.11, 1.12, 1.13, 1.14, 1.15, 1.21, 1.22, 1.23, 1.24, 1.25, 1.26, 1.27, 1.36, 1.44, 2.1, 2.2, 2.3, 2.4, 2.7 and 2.27 in the greenhouse.

Use Examples (Defoliation Activity)

The comparative agent used was

A 6,7-dihydrodipyrido[1,2-alpha:2',1'-c]pyridilium as the dibromide monohydrate salt (common name: Diquat®).

The comparative agent was used in the form of the preformulated commercial product.

The test plants used were young, 4-leaved cotton plants (without cotyledons) of the Stoneville 825 variety, which were grown under greenhouse conditions (relative humidity from 50 to 70%; day/night temperature 27/20° C.).

Use Example 1

The leaves of the young cotton plants were treated to run-off with aqueous formulations of the stated active ingredients (with the addition of 0.15% by weight, based on the spray liquor, of fatty alcohol alkoxylate Plurafac LF 700). The amount of water applied was equivalent to 1000 l/h. After 13 days, the number of dropped leaves and the degree of defoliation in % were determined. In the case of the untreated control plants, no dropping of leaves occurred.

| Agent containing active ingredient No. | Converted application rate [kg/ha] | Defoliation |
| --- | --- | --- |
| 3.1 | 0.05 | 53 |
|  | 0.10 | 73 |
| A | 0.10 | 0 |

The result shows that the novel substituted 3-phenyluracils I have a very good defoliant effect and are superior to the commercial product A in this respect.

Use Examples (Insecticidal Activity)

The insecticidal activity of the compounds of the general formulae I, Ia and Ib could be demonstrated by the following experiments:

The active ingredients were formulated
a) as a 0.1% strength solution in acetone or
b) as a 10% strength emulsion in a mixture of 70% by weight of cyclohexanol, 20% by weight of Nekanil® LN (Lutensol® AP6, wetting agent having an emulsifying and dispersing effect and based on ethoxylated alkylphenols) and 10% by weight of Emulphor® EL (Emulan® EL, emulsifier based on ethoxylated fatty alcohols)

and were diluted to the desired concentration with acetone in the case of a) and with water in the case of b).

After completion of the experiments, the lowest concentration in each case at which the compounds still caused 80–100% inhibition or mortality (activity threshold or minimum concentration) in comparison with untreated control experiments was determined.

We claim:

1. A 3-phenyluracil of formula I $$(I)$$

wherein $X^1$ and $X^2$ are each oxygen or sulfur,

W is $C(R^8)=X^5$, wherein $X^5$ is oxygen, sulfur, or a radical $NR^{14}$, $R^{14}$ being hydroxyl, $C_1$–$C_6$-alkoxy, $C_3$–$C_6$-alkenyloxy, $C_3$–$C_6$-alkynyloxy, $C_5$–$C_7$-cycloalkoxy, $C_5$–$C_7$-cycloalkenyloxy, $C_1$–$C_6$-haloalkoxy, $C_3$–$C_6$-haloalkenyloxy, hydroxy-$C_1$–$C_6$-alkoxy, cyano-$C_1$–$C_6$-alkoxy, $C_3$–$C_7$-cycloalkyl-$C_1$–$C_6$-alkoxy, $C_1$–$C_6$-alkoxy-$C_1$–$C_6$-alkoxy, $C_1$–$C_6$-alkoxy-$C_3$–$C_6$-alkenyloxy, $C_1$–$C_6$-alkylcarbonyloxy, $C_1$–$C_6$-haloalkylcarbonyloxy, $C_1$–$C_6$-alkylcarbamoyloxy, $C_1$–$C_6$-haloalkylcarbamoyloxy, $C_1$–$C_6$-alkoxycarbonyl-$C_2$–$C_6$-alkoxy, $C_1$–$C_6$-alkylthio-$C_1$–$C_6$-alkoxy or di-$C_1$–$C_6$-alkylamino-$C_1$–$C_6$-alkoxy, and $R^8$ is hydrogen, cyano or $C_1$–$C_6$-alkyl, $R^1$ is halogen or cyano, $R^2$ is hydrogen or halogen, $R^3$ is hydrogen or $C_1$–$C_6$-alkyl, $R^4$ is cyano, $C_1$–$C_6$-alkyl or $C_1$–$C_6$-haloalkyl, $R^5$ is hydrogen, halogen or $C_1$–$C_6$-alkyl, or a salt of a compound I wherein $R^3$ is hydrogen.

2. The compound defined in claim 1, wherein $R^1$ is chlorine or bromine.

3. The compound defined in claim 1, wherein $R^2$ is hydrogen or fluorine.

4. The compound defined in claim 1, wherein $R^3$ is $C_1$–$C_6$-alkyl.

5. The compound defined in claim 1, wherein $R^4$ is $C_1$–$C_6$-haloalkyl.

6. The compound defined in claim 1, wherein $R^5$ is hydrogen.

7. The compound defined in claim 1, wherein $X^1$ is oxygen, $X^2$ is oxygen or sulfur, $R^4$ is $C_1$–$C_6$-haloalkyl, $R^5$ is hydrogen, and $X^5$ is oxygen or a radical $NR^{14}$.

8. The compound defined in claim 1, wherein $X^1$ is oxygen, $X^2$ is oxygen, $R^1$ is chlorine, $R^2$ is hydrogen or fluorine, $R^3$ is methyl, $R^4$ is trifluoromethyl, $R^5$ is hydrogen, and $X^5$ is oxygen or a radical $NR^{14}$.

9. A herbicidal composition containing an inert liquid or solid carrier and a herbicidal amount of at least one 3-phenyluracil of formula I defined in claim 1 or a salt of at least one 3-phenyluracil I wherein $R^3$ is hydrogen.

10. A method for controlling undesirable plant growth, wherein a herbicidal amount of the 3-phenyluracil of formula I defined in claim 1 or a salt of at least one 3-phenyluracil I wherein $R^3$ is hydrogen is allowed to act on plants, on their habitat or on seed.

11. A composition for the desiccation and defoliation of plants, containing, in addition to conventional additives, an amount, having a defoliant or desiccant effect, of at least one 3-phenyluracil of formula I defined in claim 1 or a salt of at least one 3-phenyluracil I wherein $R^3$ is hydrogen.

12. A method for the desiccation and defoliation of plants, wherein an amount, having a defoliant or desiccant effect, of the 3-phenyluracil I defined in claim 1 is allowed to act on the plants.

13. A method for the desiccation and defoliation of cotton, wherein an amount, having a defoliant and/or desiccant effect, of the 3-phenyluracil I defined in claim 1 is allowed to act on the cotton.

14. A 3-phenyluracil of formula I $$(I)$$

wherein $X^1$ and $X^2$ are each oxygen or sulfur,

W is $C(R^8)=NR^{14}$, wherein $R^{14}$ is hydroxyl, $C_1$–$C_6$-alkoxy, $C_3$–$C_6$-alkenyloxy, $C_3$–$C_6$-alkynyloxy, $C_5$–$C_7$-cycloalkoxy, $C_5$–$C_7$-cycloalkenyloxy, $C_1$–$C_6$-haloalkoxy, $C_3$–$C_6$-haloalkenyloxy, hydroxy-$C_1$–$C_6$-alkoxy, cyano-$C_1$–$C_6$-alkoxy, $C_3$–$C_7$-cycloalkyl-$C_1$–$C_6$-alkoxy, $C_1$–$C_6$-alkoxy-$C_1$–$C_6$-alkoxy, $C_1$–$C_6$-alkoxy-$C_3$–$C_6$-alkenyloxy, $C_1$–$C_6$-alkylcarbonyloxy, $C_1$–$C_6$-haloalkylcarbonyloxy, $C_1$–$C_6$-alkylcarbamoyloxy, $C_1$–$C_6$-haloalkylcarbamoyloxy, $C_1$–$C_6$-alkoxycarbonyl-$C_2$–$C_6$-alkoxy or $C_1$–$C_6$-alkylthio-$C_1$–$C_6$-alkoxy, di-$C_1$–$C_6$-alkylamino-$C_1$–$C_6$-alkoxy, and $R^8$ is hydrogen, cyano or $C_1$–$C_6$-alkyl, $R^1$ is halogen or cyano, $R^2$ is hydrogen or halogen, $R^3$ is hydrogen or $C_1$–$C_6$-alkyl, $R^4$ is cyano, $C_1$–$C_6$-alkyl or $C_1$–$C_6$-haloalkyl, $R^5$ is hydrogen, halogen or $C_1$–$C_6$-alkyl, or a salt of a compound I wherein $R^3$ is hydrogen.

15. The compound defined in claim 14, wherein $R^1$ is chlorine or bromine.

16. The compound defined in claim 14, wherein $R^2$ is hydrogen or fluorine.

17. The compound defined in claim 14, wherein $R^3$ is $C_1$–$C_6$-alkyl.

18. The compound defined in claim 14, wherein $R^4$ is $C_1$–$C_6$-haloalkyl.

19. The compound defined in claim 14, wherein $R^5$ is hydrogen.

20. The compound defined in claim 14, wherein $X^1$ is oxygen, $X^2$ is oxygen or sulfur, $R^4$ is $C_1$–$C_6$-haloalkyl and $R^5$ is hydrogen.

21. The compound defined in claim 14, wherein $X^1$ is oxygen, $X^2$ is oxygen, $R^1$ is chlorine, $R^2$ is hydrogen or fluorine, $R^3$ is methyl, $R^4$ is trifluoromethyl, and $R^5$ is hydrogen.

22. The compound defined in claim 14, wherein $X^1$ is oxygen, $X^2$ is oxygen, $R^1$ is chlorine, $R^2$ is hydrogen or fluorine, $R^3$ is methyl, $R^4$ is trifluoromethyl, $R^5$ is hydrogen, $R^8$ is hydrogen, and $R^{14}$ is methoxy or 1-(ethoxycarbonyl)ethoxy.

23. A herbicidal composition containing an inert liquid or solid carrier and a herbicidal amount of at least one 3-phenyluracil of formula I defined in claim 14 or a salt of at least one 3-phenyluracil I wherein $R^3$ is hydrogen.

24. A method for controlling undesirable plant growth, wherein a herbicidal amount of the 3-phenyluracil of formula I defined in claim 14 or a salt of at least one 3-phenyluracil I wherein $R^3$ is hydrogen is allowed to act on plants, on their habitat or on seed.

25. A composition for the desiccation and defoliation of plants, containing, in addition to conventional additives, an amount, having a defoliant or desiccant effect, of at least one 3-phenyluracil of formula I defined in claim 14 of a salt of at least one 3-phenyluracil I wherein $R^3$ is hydrogen.

26. A method for the desiccation and defoliation of plants, wherein an amount, having a defoliant or desiccant effect, of the 3-phenyluracil I defined in claim 14 is allowed to act on the plants.

27. A method for the desiccation and defoliation of cotton, wherein an amount, having a defoliant and/or desiccant effect, of the 3-phenyluracil I defined in claim 14 is allowed to act on the cotton.

* * * * *

UNITED STATES PATENT AND TRADEMARK OFFICE
CERTIFICATE OF CORRECTION

PATENT NO. : 6,239,074 B1
DATED : May 29, 2001
INVENTOR(S) : Klintz et al.

It is certified that error appears in the above-identified patent and that said Letters Patent is hereby corrected as shown below:

<u>Column 112, claim 25,</u>
Line 10, "of a salt of" should be -- or a salt of --.

Signed and Sealed this

Sixteenth Day of October, 2001

Attest:

NICHOLAS P. GODICI
Attesting Officer
Acting Director of the United States Patent and Trademark Office